US009678061B2

(12) United States Patent
Dornmair et al.

(10) Patent No.: US 9,678,061 B2
(45) Date of Patent: Jun. 13, 2017

(54) IDENTIFICATION OF T CELL TARGET ANTIGENS

(75) Inventors: Klaus Dornmair, Olching (DE); Reinhard Hohlfeld, Martinsried (DE); Jorg Prinz, Munich (DE); Katherina Siewert, Munich (DE); Song-Min Kim, Munich (DE)

(73) Assignee: Ludwig-Maximilians-Universität München, München (DE)

( * ) Notice: Subject to any disclaimer, the term of this patent is extended or adjusted under 35 U.S.C. 154(b) by 1025 days.

(21) Appl. No.: 13/814,263

(22) PCT Filed: Aug. 5, 2011

(86) PCT No.: PCT/EP2011/063538

§ 371 (c)(1), (2), (4) Date: Apr. 19, 2013

(87) PCT Pub. No.: WO2012/017081

PCT Pub. Date: Feb. 9, 2012

(65) Prior Publication Data

US 2013/0195900 A1 Aug. 1, 2013

(30) Foreign Application Priority Data

Aug. 6, 2010 (EP) .................................... 10008233

(51) Int. Cl.

| | |
|---|---|
| ***G01N 33/53*** | (2006.01) |
| ***G01N 33/50*** | (2006.01) |
| ***C12Q 1/68*** | (2006.01) |
| ***G01N 33/569*** | (2006.01) |
| *A61K 39/00* | (2006.01) |

(52) U.S. Cl.

CPC ......... *G01N 33/505* (2013.01); *C12Q 1/6883* (2013.01); *G01N 33/56977* (2013.01); *A61K 39/00* (2013.01); *C12Q 2600/16* (2013.01); *G01N 2333/7051* (2013.01); *G01N 2333/70539* (2013.01)

(58) Field of Classification Search

None

See application file for complete search history.

(56) References Cited

U.S. PATENT DOCUMENTS

| | | | | |
|---|---|---|---|---|
| 6,429,286 | B1 | 8/2002 | Sugimura | |
| 2002/0192705 | A1 | 12/2002 | Matsushita et al. | |
| 2003/0003485 | A1* | 1/2003 | Uenaka ................ | G01N 33/505 435/6.16 |
| 2004/0106159 | A1 | 6/2004 | Kern et al. | |

FOREIGN PATENT DOCUMENTS

| | | |
|---|---|---|
| JP | 2008-263950 | 6/2008 |
| JP | 2009-515534 | 4/2009 |
| WO | 2009004315 | 1/1999 |
| WO | 02084567 | 10/2002 |
| WO | 2009137225 | 11/2009 |
| WO | 2010053587 | 5/2010 |

OTHER PUBLICATIONS

Siewert et al. (Nat Med. May 2012;18(5):824-8 and 15 pages of Supplementary Information).*

Cecconi et al., Cytometry A. Nov. 2008;73(11):1010-8.*

Vollers et al., Immunology. Mar. 2008;123(3):305-13.*

Blanchard et al., J Immunol 2004; 173:3062-3072.*

Michael Dustin, Curr Top Microbiol Immunol. 2009;334:47-70.*

Dornmair, et al. "T-cell-mediated autoimmunity: novel techniques to characterize autoreactive T-cell receptors." The American Journal of Pathology, vol. 163, No. 4, Oct. 2003, pp. 1215-1226.

Dornmair, et al. "Novel approaches for identifying target antigens of autoreactive human B and T cells" Seminars in Immunopathology, Springer, Berlin, DE. vol. 31, No. 4, Sep. 11, 2009. pp. 467-477.

Hemmer B, et al. "Identification of high potency microbial and self ligands for human autoreactive class II-restricted T cell clone." The Journal of Experimental Medicine, May 5, 1997, vol. 185, No. 9, pp. 1651-1659.

Dornmair, et al. "OR. 62. A Protocol for Characterizing T-Cell Receptors from Human Histological Specimens and for Identifying Their Antigens." Clinical Immunology, Academic Press, US, vol. 119, Jan. 1, 2006.

Markovic-Plese et al. "High level of cross-reactivity in influenza virus hemagglutinin-specific CD4+ T-cell response: Implications for the initiation of autoimmune response in multiple sclerosis", Journal of Neuroimmunology, Dec. 1, 2005, vol. 169, No. 1-2.

Sospedra M, et al. "Combining positional scanning peptide libraries, HLA-DR transectants and bioinformatics to dissect the epitope spectrum of HLA class II cross-restricted CD+ T Cell clones." Journal of Immunological Methods, vol. 353, No. 1-2, Feb. 28, 2010.

(Continued)

*Primary Examiner* — Zachary Skelding

(74) *Attorney, Agent, or Firm* — DT Ward, PC; Donna T. Ward; Lingyun Jia

(57) ABSTRACT

The present invention relates to a method of identifying a target antigen of T cells comprising (a) contacting (aa) cells expressing (i) a functional T cell receptor complex comprising predefined matching T cell receptor α and β chains; and (ii) a read-out system for T cell activation; with (ab) antigen-presenting cells carrying (iii) peptide libraries encoded by randomised nucleic acid sequences; and (iv) MHC molecules recognised by the T cell receptor of (i); (b) assessing T cell activation using said read-out system; (c) isolating antigen-presenting cells that are in contact with the cells in which the read-out system indicates T cell activation; (d) identifying the target antigen or the nucleic acid molecule encoding said target antigen.

6 Claims, 10 Drawing Sheets

(56) References Cited

OTHER PUBLICATIONS

Figure 1:
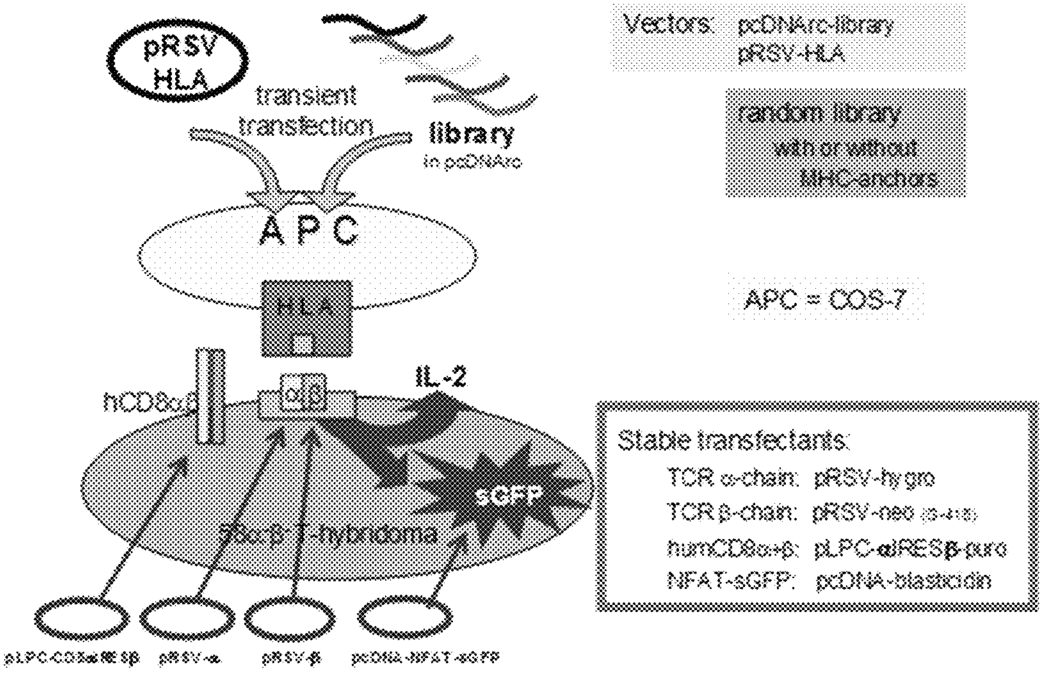

Sietz et al. "Reconstitution of paired T cell receptor—and beta-chains from microdissected single cells of human inflammatory tissues." Proceedings of the National Academy of Sciences, vol. 103, No. 32, Jul. 31, 2006, pp. 12057-12062.
International Search Report for International Application No. PCT/EP2011/063538 dated Dec. 13, 2011.
Boen, E. A.R. Crownover, M. McIlhaney, A.J. Korman, and J. Bill, "Identification of T Cell Ligands in a Library of Peptides Covalently Attached to HLA-DR4" (2000) Journal of Immunology 165:2040-2047.
Dogan, I. et al., "Phage-displayed libraries of peptide/major histocompatibility complexes" (2004) Eur. J. Immunology 34:598-607.
Morgan, R.A. et al., "High Efficiency TCR Gene Transfer into Primary Human Lymphocytes Affords Avid Recognition of Melanoma Tumor Antigen Glycoprotein 100 and Does Not Alter the Recognition of Autologous Melanoma Antigens" (2003) Journal of Immunology 171:3287-3295.
Siewert, K. et al., "Unbiased identification of target antigens of CD8+T cells with combinatorial libraries coding for short peptides" (2012) Nature Medicine 18(5):824-829.
Uemura, Y. et al., "Systematic Analysis of the Combinatorial Nature of Epitopes Recognized by TCR Leads to Identification of Mimicry Epitopes for Glutamic Acid Decarboxylase 65-Specific TCRs" (2003) Journal of Immunology 170:947-960.
Uemura, Y. et al., "Construction of diversity analysis system . . . " (2003) Molecular mimicry 206(11):836-840.
Wang, Y. et al., "Using a baculovirus display library to identify MHC class I mimotopes" (2005) PNAS 102 (7):2476-2481.
Aarnoudse, C.A., et al. "TCR Reconstitution in Jurkat Reporter Cells Facilitates the Identficiation of Novel Tumor Antigens by CDNA Expression Cloning", (2002) Int. J. Cancer 99:7-13.
Jenson, J.S., et al., "The cellular immune recognition of proteins expressed by an African swine fever virus random genomic library", (2000) Journal of Immunological Methods 242:33-42.
Karttunen, J. and Nilabh Shastri, "Measurement of ligand-induced activation in single viable T cells using the lacZ reporter gene", (1991) Proc. Natl. Acad. Sci. 88:3972-3976.
Karttunen, J. Sarah Sanderson, and Nilabh Shastri, "Detection of rare antigen-presenting cells by the lacZ T-cell activation assay suggests an expression cloning strategy for T-cell antigens" (1992) Proc. Natl. Acad. Sci. 89:6020-6024.
Japanese Office Action (with translation), Dated Jun. 7, 2016, from Japanese Patent Application No. 2013-522265.
Tolstrup, A.B. et al., "Functional screening of a retroviral peptide library for MHC class I presentation" (2001) Gene 263:77-81.
Invitrogen Life Sciences, "pFliTrx Peptide Display Vector A Cloning Vector for Studying Protein-Protein Interactions" Catalog No. V1126-01 Version D. http://tools.thermofisher.com/content/sfs/manuals/pflitrxvector_man.pdf.
Müller, O.J., "Random peptide libraries displayed on adeno-associated virus to select for targeted gene therapy vectors" (Sep. 2003) Nature Biotechnology 21(9):1040-1046.
Consultation with the Examining Division, Dated Nov. 4, 2016, from European Patent Application No. EP 11 73 9098.9.

* cited by examiner

Fig 2a: COS-7-A2$^{stable}$ + flu(58-66)-peptide

Fig 2b: COS-7$^{empty}$ + flu(58-66)-peptide

Fig 2c: COS-7-A2$^{stable}$ + pcDNA-flu(58-66)

Fig 2d: COS-7$^{empty}$ + pcDNA-flu(58-66)

Fig 2e: COS-7-A2$^{trans}$ + pcDNA-flu(58-66)

Fig 2f: COS-7-A2$^{trans}$ + pcDNA empty

Fig 2g: COS-7-A2$^{trans}$ + pcDNA-flu(1-252)

Fig 2h: COS-7-A2$^{stable}$ + hCMV-peptide

Figure 5:
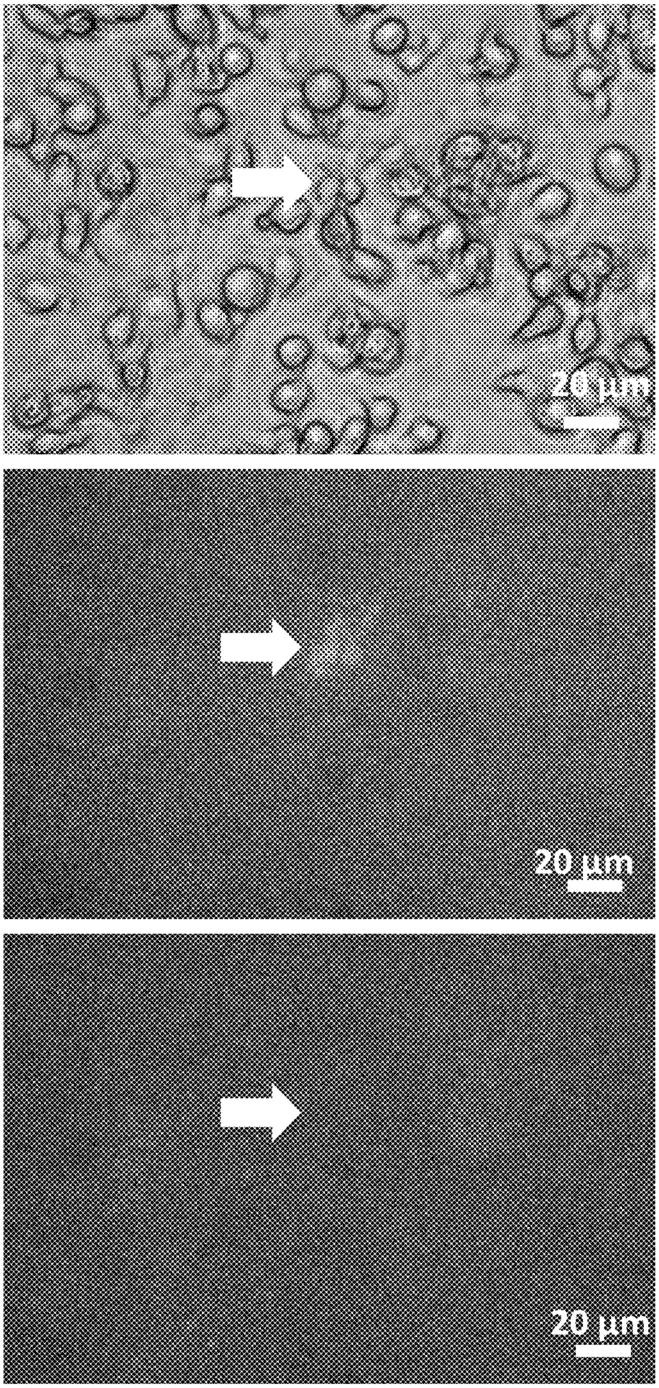

Fig 5: COS-7-A2$^{trans}$ + pcDNA-A2-269 lib

Figure 7

| | | | | | | | | | |
|---|---|---|---|---|---|---|---|---|---|
| flu(58-66) | G | I | L | G | F | V | F | T | L |
| mimo-1 | T | I | L | G | F | V | F | T | L |
| mimo-2(x2) | A | I | L | G | W | V | F | T | L |
| mimo-3 | Q | I | M | G | F | V | F | T | L |
| mimo-4 | A | I | A | G | F | V | F | T | L |

IDENTIFICATION OF T CELL TARGET ANTIGENS

CROSS REFERENCE TO RELATED APPLICATIONS

This application is a 35 U.S.C. §371 U.S. National Stage Entry of International Application No. PCT/EP2011/063538 filed Aug. 5, 2011, which claims the benefit of priority of European Application No. 10008233.8 filed Aug. 6, 2010, the contents of which are each incorporated herein by reference in its entirety.

REFERENCE TO SEQUENCE LISTING

The present application is being filed along with a Sequence Listing in electronic format. The Sequence Listing is provided as a file entitled SEQLST20011003.txt created on Feb. 5, 2013 which is 33,240 bytes in size. The information in electronic format of the sequence listing is incorporated herein by reference in its entirety.

The present invention relates to a method of identifying a target antigen of T cells comprising (a) contacting (aa) cells expressing (i) a functional T cell receptor complex comprising predefined matching T cell receptor α and β chains; and (ii) a read-out system for T cell activation; with (ab) antigen-presenting cells carrying (iii) peptide libraries encoded by randomised nucleic acid sequences; and (iv) MHC molecules recognised by the T cell receptor of (i); (b) assessing T cell activation using said read-out system; (c) isolating antigen-presenting cells that are in contact with the cells in which the read-out system indicates T cell activation; (d) identifying the target antigen or the nucleic acid molecule encoding said target antigen. The present invention further relates to a method of identifying nucleic acid molecules encoding variable, hypervariable and/or joining regions of T cell receptor β chains as well as to this method of the invention further comprising identifying the nucleic acid molecules encoding variable, hypervariable and/or joining regions of the matching T cell receptor α chains. The present invention also relates to a method of identifying patient-specific T cell antigens comprising (A) isolating T cells from a sample obtained from said patient; (B) identifying matching T cell receptor α and β chains from the T cells isolated in (A); and (C) identifying T cell antigens in accordance with the method of the invention, wherein the cell comprising a functional T cell receptor and a read-out system for T cell activation expresses matching T cell receptor α and β chains from the T cells identified in (B). The present invention further relates to a composition comprising a T cell antigen identified by a method of the invention, a peptide library as well as a method of preparing antigen-presenting cells and a primer or a set of primers.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

T cells play crucial roles in many infectious, tumor, and autoimmune diseases, but apart from very few exceptions, the target antigens of pathogenic human T cells have remained unknown. The specificity of T cells towards their target antigens is determined by their heterodimeric, hypervariable T cell receptor (TCR) molecules, which recognize antigenic peptides that are presented by MHC molecules. In immune defense situations, the MHC molecules are of "self"-origin, whereas the antigenic peptides are "non-self", i.e. they are derived from viral or microbial peptides. Typically, class-I MHC molecules present peptides of intracellular (viral) origin to CD8+ T cells, whereas class-II MHC molecules present phagocytosed (microbial) peptides to CD4+ T cells. In addition, "self" MHC molecules also present "self" peptides, but these are normally ignored because of T cell tolerance. It is assumed that in autoimmune diseases the tolerance is broken and recognition of "self" peptides results in chronic inflammation, disturbed organ function or tissue destruction. Another important role of T cells is during tumor defense where T cells may mount anti-tumor responses. In this case, however, they recognize tumor-associated antigens.

Despite tremendous efforts by many groups of investigators who applied very different techniques, there is so far no simple, reliable, and unbiased method to determine T cell antigens. One reasons is that straightforward biochemical techniques such as immunoprecipitation or affinity chromatography can not be used, because the affinities of TCRs to MHC/peptide complexes are several orders of magnitude too low. Such techniques work well if the dissociation constant is in the nanomolar range or below, as it is typical for antibodies or conventional receptor-ligand interactions, but for TCR-MHC/peptide interactions, the dissociation constants are usually greater than $10^{-6}$ M (Rudolph et al., 2006; J. D. Stone et al (2009).

In the past, some antigens were identified by generating T cell lines in vitro against known or bona fide candidate autoimmune or tumor antigens, and the precise epitopes were mapped later using synthetic peptides.

In other approaches, antigenic peptides were eluted from MHC molecules of tumor or autoimmune tissue and analyzed by mass spectrometry (Cox et al., 1994; Fissolo et al., 2009).

A third method uses randomized synthetic peptide libraries (Nino-Vasquez et al., 2005). With this approach the idea is that TCR molecules recognize patterns rather than defined sequences or structures. In other words, the recognition of target structures is poly-specific (also termed "promiscuous" or "degenerate") (Wucherpfennig et al., 2007). Such libraries contain random amino acids in all but one position and may allow identification of "recognition patterns", i.e. of mimotopes of the natural peptides, which then may be identified by database searches. These approaches are limited to some TCRs which show an appropriate balance between specificity and poly-specificity. If the specificity is too high, the few activating peptides are too dilute in the library, if the specificity is too low, the pattern can not be recognized any more. These approaches are well suited to determine the degree of polyspecificity of TCR, but have so far in most cases failed to identify new, yet unknown antigens.

Fourth, cDNA libraries have been used in particular to investigate tumor T cell antigens. They were either transfected into COS cells via plasmids bearing the SV40 origin (Van der Bruggen et al., 1991; Wong et al., 1999; Boon et al., 2006), or via retroviral constructs into appropriate recipient cells (Smith et al., 2001). In both cases the plasmids or viral particles may be recovered from the transfected cells and amplified in bacteria. Usually many pools of plasmids are used, and positive pools are subjected to further rounds of transfections until a single antigen-bearing plasmid may be isolated and characterized. Such amplification strategies are of course advantageous as compared to biochemical or combinatorial synthetic peptide libraries. Although several tumor antigens were detected, these methods have not reached general applicability. The reasons are diverse: the libraries usually come from diseased tissue (which is often not available) and a tremendous number of clones must be screened by laborious and expensive cytotoxicity or cytokine assays, which—another limitation—require large numbers of T cells. Most importantly, however, the proteins expressed from cDNA libraries require extensive and correct processing. Hence, the processing pattern of the APCs used in vitro must be identical to the processing pattern of the original APCs. This may often not be the case.

A fifth strategy is reminiscent of phage display libraries. Here baculovirus infected insect cells display randomized peptide libraries in the binding groove of recombinant MHC molecules (Crawford et al., 2004; Wang et al., 2005; Crawford et al., 2006). These libraries are screened with fluorescent oligomerized soluble TCR molecules. Although this technology could reveal mimotopes of peptides known to activate class-I and class-II restricted TCRs, it has several intricacies. The most important drawback is, as discussed above, that TCRs have notoriously low affinities to their MHC/peptide ligands. This impedes detection of positive insect cell clones. TCR-oligomerization facilitates recognition by increasing avidity, but may presumably not completely overcome this limitation. Further, library cloning is possible only by homologous recombination which yields libraries of limited size, or by cloning directly into baculovirus DNA which is difficult, owing to its large size.

WO2003068800 describes isolated peptides that bind to HLA molecules and stimulate cytolytic T cells specific for complexes of the peptide and the HLA molecule. A transfection of antigen presenting cells with recombinant combinatorial peptide libraries is not envisaged in WO2003068800.

U.S. Pat. No. 6,037,135 discloses methods of making HLA binding peptides, but does not disclose the loading of MHC molecules with and presentation of antigens by antigen presenting cells via a peptide library encoding such peptides.

In summary, even though some of the different techniques used in the past occasionally allowed the detection of mimotopes of previously known antigens, an a priori unknown antigen could only in rare cases be discovered. Thus, despite the above described advances in the field of T cell antigen identification, there remains a need to provide improved methods for an unbiased identification of novel T cell antigens.

This need is addressed by the provision of the embodiments characterised in the claims.

Accordingly, the present invention relates to a method of identifying a target antigen of T cells comprising (a) contacting (aa) cells expressing (i) a functional T cell receptor complex comprising predefined matching T cell receptor α and β chains; and (ii) a read-out system for T cell activation; with (ab) antigen-presenting cells carrying (iii) peptide libraries encoded by randomised nucleic acid sequences; and (iv) MHC molecules recognised by the T cell receptor of (i); (b) assessing T cell activation using said read-out system; (c) isolating antigen-presenting cells that are in contact with the cells in which the read-out system indicates T cell activation; (d) identifying the target antigen or the nucleic acid molecule encoding said target antigen.

The term "target antigen of T cells", as used in accordance with the present invention, relates to an antigen that is recognised and bound by T cells. The binding of the antigen to T cells subsequently results in the activation of said T cells. T cell target antigens are recognised by T cells via a functional T cell receptor complex consisting of T cell receptors (TCR) and the CD3 complex. T cell target antigens are presented by major histocompatibility complex (MHC) molecules on the surface of antigen-presenting cells (APCs). In accordance with the present invention, the term "target antigen of T cells" refers to the peptide epitope. When the peptide epitope is complexed with an MHC molecule, reference is made to the "antigen-MHC complex" herein. Target antigens presented by MHC class I molecules are recognized by CD8+ T cells and are typically of intracellular origin, such as for example viral target antigens. Target antigens presented by MHC class II molecules are recognized by CD4+ T cells. Typically they are peptides, which originate from extracellular sources that were phagocytosed, such as for example peptides derived from microbes. Target antigens of T cells can be of an origin that is foreign to the host organism, such as for example viral or microbial peptides. Target antigens may also be of self-origin, such as for example tumor-associated antigens or self-antigens that trigger an autoimmune response in the host organism.

In a preferred embodiment, the target antigen of T cells is a target antigen of CD8+ T cells.

As used herein, the term "functional T cell receptor complex" refers to a complex capable of eliciting activation of the T cell in which the complex is expressed. The T cell receptor complex is composed of six subunits. The T cell receptor is made up of two subunits (also referred to herein as chains), TCR α and β, which form a disulfide-linked heterodimer, which comprises the variable, hypervariable and joining region of the TCR receptor complex that interacts with the antigen/MHC-complex, thus forming one single antigen-binding site. In a subgroup of T cells the T cell receptor is made up of TCR γ and δ subunits. In addition, TCR α and β-chains comprise conserved (constant) regions which interact with the proteins of the CD3-complex and fix the TCR in the membrane. The T-cell receptor complex further contains four CD3 subunits. Each CD3 complex contains one CD3γ subunit, one CD3δ subunit, and two CD3ε subunit. One of the CD3ε subunits forms a heterodimer with the CD3γ subunit, while the other CD3ε subunit forms a heterodimer with the CD3δ subunit. Antigen binding leads to the cross-linking and activation of the TCR hexamers. The signal is then conducted by the ζ-chains to further downstream intracellular compounds. Functionality of a T cell receptor complex can be analysed using methods well known in the art, such as for example measurements of phosphorylation and de-phosphorylation of proteins and other intracellular molecules (such as for example IP3), $Ca^{2+}$-influx into T-cells, production of cytokines (such as for example Interferon-γ, interleukins (such as IL-2, -4, -6, -17), TNF-α), secretion of cytotoxic granules containing perforin and granzymes or killing of target cells (Smith-Garvin et al. (2009); Murphy et al. "Janeway's Immunobiology" 2008, 7th Edition).

The term "predefined matching T cell receptor α and β chains", according to the invention, relates to α and β chains derived from one molecular type of T cell receptor, i.e. paired α and β chains. In other words, the chains are matched to represent functional T cell receptor heterodimers. The term "predefined" as used in this context refers to the purposive selection of the T cell receptor chains to represent a T cell receptor of interest, for which corresponding antigens are to be identified by the method of the invention. Preferably, the T cell receptor is a vertebrate T cell receptor, more preferably it is a mammalian T cell receptor. Even more preferably, the T cell receptor is a T cell receptor from horse, bovine, swine, canine, feline or primate. Most preferably, the T cell receptor is a human T cell receptor.

T cell receptor chains may be obtained by any method known in the art, such as for example the method described in Seitz et al. 2006, where TCR chains are cloned from morphologically characterised single cells. Such cells may be obtained from a sample obtained from a patient, for example, by laser micro-dissection of biopsy tissue. Furthermore, T cell receptors of known sequence may be employed, in which case the chains may be obtained by transfecting the cell of (aa) with a nucleic acid molecule encoding said T cell receptor chains.

In accordance with the present invention, the term "read-out system for T cell activation" relates to a system that provides a measurable signal upon activation of the T cell receptor. T cell receptor activation normally results in the activation of the respective T cell expressing said T cell receptor. Thus, the signal provided by the read-out system is representative of a successful T cell activation via T cell receptor binding of the antigen presented by the antigen-presenting cell. Said activation of the T cell receptor expressed in the cells of (aa) results in a signal such as for example the expression of a reporter protein. Non-limiting examples of reporter genes suitable to provide a measurable signal upon T cell activation include enzymes such as for example β-galactosidase, CAT, β-glucuronidase, peroxidase, β-xylosidase, catechol dioxygenase (XylE), trehalase (TreA), alkaline phosphatase or secreted alkaline phosphatase as well as fluorescent compounds, bioluminescent compounds and chemiluminescent compounds. Such read-out systems are well known in the art and are described, for example, in Suter-Crazzolara et al. (1995) or Shaner, et al. (2005).

Thus, the cells of (aa) are characterised by the expression of a functional T cell receptor complex and a read-out system, which indicates T cell activation. Such cells may be any cells comprising a T cell receptor complex, such as for example cells naturally expressing a T cell receptor complex or cells transformed or transfected with a T cell receptor or a T cell receptor complex. Such cells are also referred to as T cell receptor transfectants. Non-limiting examples of such cells are T cells, T cell hybridomas, lymphomas and artificially immortalized T cells (Katakura et al. (1998)). Preferably, the cells of (aa) are T cell hybridomas. T cell hybridomas are well known in the art and may be obtained as described in Ozaki et al. (1988); Shirahata et al. (1998); Chen et al. (2007) or as described in the examples below.

It is preferred that the cells of (aa) express only one molecular type of T cell receptor. Such cells may be, for example, naturally occurring T cells or T cell hybridomas devoid of an endogenous T cell receptor and being transfected or transformed with a T cell receptor of interest.

In an alternative embodiment, cells already expressing an endogenous T cell receptor may be transfected or transformed with a further T cell receptor of interest. In that case, the T cell receptor of interest is modified such as to prevent hetero-dimerisation between chains of the endogenous T cell receptor and chains of the T cell receptor of interest. Such modifications are well known in the art and include, without being limiting, the introduction of mutated amino acids at the interface of the constant regions of the T cell receptor chains of interest, or choosing T cells of very limited heterogeneity, such as oligo- or monoclonal T cell populations, as recipients (Voss et al. (2008); Cohen et al. (2007); Kuball et al. (2007); Weinhold et al. (2007); van Loenen et al. (2010); Bendle et al. (2010)). It is preferable that if cells expressing different molecular types of T cell receptor are employed in the method of the invention, further rounds of screening are carried out using different cells, such as for example cells expressing the T cell receptor of interest with only one endogenous T cell receptor, wherein said endogenous T cell receptor differs from the T cell receptor(s) present in the cells of the first or previous rounds of screening. Preferably, the cells employed in such further rounds of screening only express the T cell receptor of interest, in order to confirm that the antigen identified is an antigen of the T cell receptor of interest and not an antigen of the endogenous T cell receptor.

The term "antigen-presenting cells", as used herein, relates to cells that display antigen in complex with the major histocompatibility complex (MHC) on its surface. Any cell is suitable as an antigen-presenting cell in accordance with the present invention, as long as it expresses an MHC and presents an antigen. Cells that have in vivo the potential to act as antigen presenting cells include for example dendritic cells, macrophages, B-cells or activated epithelial cells but also fibroblasts, glial cells, pancreatic beta cells or vascular endothelial cells. Such cells may be employed in accordance with the present invention after transfection or transformation with a peptide library as defined below. Also cells not endogenously expressing MHC may be employed, in which case suitable MHC are to be transformed or transfected into said cells.

The term "peptide libraries encoded by randomised nucleic acid sequences", according to the present invention, relates to a collection of peptides, i.e. a library, wherein the peptides are encoded by nucleic acid sequences of arbitrary sequences. In other words, the nucleic acid sequences represent a variety of possible sequence variations randomly chosen. That is, if the peptide library represents peptides having, for example, a length of 9 amino acids, then the encoding nucleic acid sequences would have to be 27 nucleotides long, which means a total of $4^{27}=1.8\times10^{16}$ different nucleic acid sequences would represent each possible nucleotide combination. Preferably, the peptide library is encoded by a set of nucleic acid sequences representing at least $10^3$ different nucleic acid sequences, such as at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$ or at least $10^{16}$ different nucleic acid sequences. Most preferably, the peptide library is encoded by a set of nucleic acid sequences representing all possible permutations for a given peptide length. Furthermore, peptide libraries encompassing peptides of different lengths are also envisaged herein and the above defined amounts of nucleic acid sequence representation within said library apply mutatis mutandis.

In addition, for a number of target antigens of MHC complexes so-called anchor positions are known to be required for binding between the antigen and the MHC. Where these anchor positions are known, the randomised nucleic acid sequences may also be generated by introducing in these positions fixed amino acids and randomising solely the remaining positions. Anchor positions for various MHCs are known, such as for example in HLA-A2, as discussed in the examples, where anchor positions are isoleucine in position 2, valine in position 6 and leucine in position 9 (Rammensee et al., 1999). Further anchors are known in the art and are described, for example in (Rammensee et al., 1999).

The term "peptide" as used herein describes a group of molecules consisting of up to 50 amino acids. Peptides may further form dimers, trimers and higher oligomers, i.e. consisting of more than one molecule which may be identical or non-identical. The corresponding higher order structures are, consequently, termed homo- or heterodimers, homo- or heterotrimers etc. The term "peptide" (wherein "polypeptide" is interchangeably used with "protein") also refers to naturally modified peptides wherein the modification is effected e.g. by glycosylation, acetylation, phosphorylation and the like. Such modifications are well-known in the art. Preferably, the peptides have a minimum length of at least 4 amino acids, such as for example at least 5, at least 6, at least 7, at least 8, at least 9 or at least 10 amino acids. Also preferred is that the peptides have a length of at the most 50 amino acids, such as for example at most 45, such as at most 40, at most 35, at most 30, at most 25, at most 20 amino acids. Any of the intermediate numbers not explicitly mentioned are also envisaged herein. More preferably, peptides represented by MHC class I molecules have a length of between 4 and 20 amino acids. Thus, said peptides may be 4, 5, 6, 7, 8, 9, 10, 11, 12, 13, 14, 15, 16, 17, 18, 19 or 20 amino acids in length. Also preferred is that peptides represented by MHC class II molecules have a length of between 4 and 50 amino acids. The class II peptides may in principle be infinitely long, because they may reach out from the MHC binding groove at both sides. The epitope itself is normally 8 to 10 amino acids long. Thus, said peptides may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids in length. Even more preferably, the peptides of the present invention have a length of between 8 to 10 amino acids. Most preferably, the peptides have a length of 9 amino acids.

"Nucleic acid sequences", in accordance with the present invention, include DNA, such as cDNA or genomic DNA, and RNA. It is understood that the term "RNA" as used herein comprises all forms of RNA and preferably refers to mRNA. Further included are nucleic acid mimicking sequences known in the art such as synthetic or semisynthetic derivatives of DNA or RNA and mixed polymers, both sense and antisense strands. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see Braasch and Corey (2001) Chem. Biol. 8, 1). LNA is an RNA derivative in which the ribose ring is constrained by a methylene linkage between the 2'-oxygen and the 4'-carbon. They may contain additional non-natural or derivatized nucleotide bases, as will be readily appreciated by those skilled in the art.

Due to the randomised nature of the nucleic acid sequences, considerations based on a known target sequence are not required. Thus, the peptide libraries employed in the present invention differ from the prior art in that in the prior art, one would have to design the nucleic acid sequences according to a known sequence of the gene, whereas from the present library one can screen through a fully random panel of different peptides (without the need of prior knowledge of their sequences) to look for a target antigen of T cells. In a preferred embodiment, the randomised nucleic acid sequences encoding the peptide library/libraries do not encode a naturally occurring gene. In other words, the term "randomised nucleic acid sequences" does not include full length genes encoding a particular protein nor cDNAs, such as for example cDNAs derived from mRNA.

Preferably, the nucleic acid sequences encoding the peptides of the peptide library are incorporated into a vector.

Preferably, the vector is a plasmid, cosmid, virus, bacteriophage or another vector used e.g. conventionally in genetic engineering. The nucleic acid sequences of the present invention may be inserted into several commercially available vectors. Non-limiting examples include vectors compatible with an expression in mammalian cells like pREP (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega).

For vector modification techniques, see Sambrook and Russel (2001), loc. cit. Generally, vectors can contain one or more origin of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The coding nucleic acid sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the nucleic acid sequences of the invention are operatively linked to such expression control sequences allowing expression in eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Possible examples for regulatory elements ensuring the initiation of transcription comprise the cytomegalovirus (CMV) promoter, SV40-promoter, RSV-promoter (Rous sarcome virus), the lacZ promoter, the gai10 promoter, human elongation factor 1α-promoter, CMV enhancer, CaM-kinase promoter, the *Autographa californica* multiple nuclear polyhedrosis virus (AcMNPV) polyhedral promoter or the SV40-enhancer. Examples for further regulatory elements in eukaryotic cells comprise transcription termination signals, such as SV40-poly-A site or the tk-poly-A site or the SV40, lacZ and AcMNPV polyhedral polyadenylation signals, downstream of the nucleic acid sequences.

Furthermore, it is preferred that the vector of the invention comprises a selectable marker. Examples of selectable markers include neomycin, ampicillin, and hygromycin resistance and the like. Specifically-designed vectors allow the shuttling of DNA between different hosts, such as bacteria-fungal cells or bacteria-animal cells.

An expression vector according to this invention is capable of directing the replication, and the expression, of the nucleic acid sequences and encoded peptides of this invention. Suitable expression vectors which comprise the described regulatory elements are known in the art such as Okayama-Berg cDNA expression vector pcDV1 (Pharmacia), pRc/CMV, pcDNA1, pcDNA3 (Invitrogene, as used, inter alia in the appended examples), pSPORT1 (GIBCO BRL), Gateway plasmids (Invitrogen) or pGEMHE (Promega).

The nucleic acid sequences of the invention as described herein above may be designed for direct introduction or for introduction via electroporation (using for example Multiporator (Eppendorf) or Genepulser (BioRad)), PEI (Polysciences Inc. Warrington, Eppelheim), $Ca^{2+}$-mediated transfection or via liposomes (example: "Lipofectamine" (Invitrogen)), non-liposomal compounds (example: "Fugene" (Roche)), liposomes, phage vectors or viral vectors (e.g. adenoviral, retroviral, lentiviral) into the cell. Additionally, baculoviral systems or systems based on Vaccinia Virus or Semliki Forest Virus can be used as eukaryotic expression system for the nucleic acid sequences of the invention.

The term "MHC" is used interchangeably with HLA herein. In accordance with the present invention it is a prerequisite that "MHC molecules recognised by the T cell receptor" are employed. Thus, when screening for a CD8+ T cell target antigen, the MHC expressed by the cell of (ab) has to be a class I MHC while when screening for CD4+ T cell target antigen, the MHC has to be a class II MHC. Furthermore, the specific MHC recognised by the T cell receptor expressed by the cell of (aa) needs to be employed. When the specific HLA gene encoding the MHC recognised by the T cell receptor under investigation is not know, then a preceding experiment may be performed to screen the complete set of all MHC (HLA) molecules expressed from all alleles of the subject, e.g. of a patient, using methods well established in the art, such as for example as discussed in Robinson J, et al. (2003) (see: http://www.ebi.ac.uk/imgt/hla/citations.html); Bettinotti et al. (2003); Marsh et al (2010).

Accordingly, the cells of (aa) that express the T cell receptor of interest will be activated when in contact with those cells (ab) that present an antigen of said T cell receptor. T cell activation is observable due to the read-out system and allows for convenient isolation of the cell complex of (ab) with (aa) or of the activating cells of (ab) only. Methods of isolation of cells are well known in the art and include, without being limiting, manual picking of cells or automated picking by use of a robot, laser-capture microdissection or FACS (fluorescence activated cell sorting). Such methods are described for example in Murray (2007) or Tung et al. (2007) as well as in the examples below.

After isolation of the antigen presenting cell of (ab), the nucleic acid molecule encoding the peptide(s) of the peptide library present in said individual cell are isolated. Methods of isolation of a nucleic acid molecule are well known in the art and exemplary methods are also described in the examples below. Prior to identification of the target antigen or the nucleic acid molecule encoding it, said nucleic acid molecule may be amplified. Amplification can include, for example, amplification of the nucleic acid molecule via PCR technology as further detailed below and/or transfection of the nucleic acid molecule into bacterial cells and subsequent culture of the bacteria.

The amplified nucleic acid molecules or the peptides encoded by these nucleic acid molecules are then identified. The term "identifying", as used in accordance with the present invention, refers to determining the amino acid or nucleic acid sequence of the target antigen(s). Methods of identification of nucleic acid molecules include, without being limiting, nucleic acid sequencing.

Subsequently, the target antigen or the nucleic acid molecule encoding said target antigen is identified.

In accordance with the present invention, an unbiased and straightforward technique for determining the target antigens of T cells is provided. As is shown in the examples below, the intricacies of protein processing are circumvented by co-transfecting a recombinant combinatorial library encoding short peptides and the appropriate MHC-I molecules into cells, such as for example COS cells. The library contains plasmids comprising random nucleotide sequences encoding short peptides. These plasmids can be easily recovered. Transfected COS cells are, as for example shown in the examples below, screened with cells which carry functional CD3 and downstream signalling molecules and are co-transfected with TCR α- and β-chains (T-cell receptor transfectants), human CD8 α- and β-chains, and sGFP under the control of the response element of the nuclear factor of activated T cells (NFAT) in cells that carry NFAT (Fiering et al., 1990; Karttunen and Shastri, 1991). Preferably, these cells are TCR-transfected T-hybridoma cells, as this provides unlimited numbers of "revived" T cells and avoids establishing "real" T cell clones, which is often more problematic.

A confluent layer of library-presenting COS cells is overlaid with the TCR-transfectants. Whenever a particular single TCR-transfectant is activated by a peptide from the library, it lights up green, and the underlying COS cell can be picked with a micromanipulator under a fluorescent microscope. By this high-throughput approach, several millions of library-peptides can be examined within a few hours. This approach is more efficient than previously described methods, which measured cytotoxicity or secreted cytokines in pools of plasmid transfected APCs or by several rounds of FACSort (Van der Bruggen et al., 1991; Smith et al., 2001; Nino-Vasquez et al., 2005; Crawford et al., 2006).

The library-plasmids from the recovered COS-cell may then be isolated, subjected to a new round of screening, and are finally sequenced. Then the T cell receptor activating motif can be analyzed and compared to existing proteins in the database. The feasibility of this technique is demonstrated in the appended examples using the well investigated TCR JM22 (Gotch et al., 1987; Stewart-Jones et al., 2003; Ishizuka et al., 2008) that is specific for HLA-A2 and the influenza matrix protein peptide flu(58-66).

A major advantage of the inventive technology is that it does not depend on the antigen processing machinery of the antigen-presenting cells by providing plasmid vectors encoding short peptides. As is shown in the examples, a high number of antigen-presenting cells efficiently present the encoded peptides (e.g. flu(58-66)) after transfection with plasmid pcDNA (FIG. 2*c,e*). The examples also provide evidence that the peptides, such as flu(58-66), are efficiently transported after expression into the lumen of the endoplasmic reticulum where they are loaded onto HLA-A*0201. Strikingly, the full-length protein flu(1-252) was not recognized (FIG. 2*g*). This suggests that the full length protein is not correctly processed by COS-7 cells and illustrates a general problem of cDNA libraries, namely that they rely on the processing machinery of the chosen APC. A situation that exactly resembles antigen presentation in a lesion of a patient will presumably never be available in vitro, for several reasons: First, in many cases it is not even known which cells present the (auto)antigen in situ. Second, even if this were known, it would be almost impossible or at least very difficult to obtain and propagate the original APCs. Third, antigen processing in inflamed tissue may be altered as compared to healthy tissue (Martinon et al., 2009). This may lead to a very different peptide spectrum from identical parent proteins. Fourth, the antigens, i.e. the cDNA libraries, must be introduced into primary cells, and it is known that the transfection and transformation efficacies are very low. The method presented herein circumvents all these problems since it does not depend on antigen processing at all. Further, COS cells can be transfected with high efficacy and they amplify the plasmid vector in their cytosol, which allows for it to be recovered and analyzed.

The results provided herein demonstrate that it is possible to identify mimotopes that allow unequivocal identification of the parent, naturally occurring peptide by a simple database search. The list of identified mimotopes generated by the present technology may not be complete, because some peptides may be digested further by endo- or exopeptidases in the cytosol of the COS cells, or some may be lost due to their chemical properties, i.e. they may be hydrophobic and insert into membranes, or they may bind to proteins or other cellular components. There are indeed technologies which are based on chemically synthesized peptide libraries, that provide a comprehensive overview on the polyspecificity of a particular TCR (Nino-Vasquez et al., 2005). However, reports on identification of a priori unknown antigens are scarce. This is presumably due to the fact that chemically synthesized peptides may only be analyzed in pools of a tremendous multitude of other peptides: The "correct" peptide may therefore be present in the library, but only at a dilution that is too low to be detected. In contrast, the high-throughout technology of the present invention allows to pick a single activating cell from millions of negative cells, and then to amplify the positive plasmid. Thus, the present approach is oriented pragmatically: even if the list of mimotopes may be incomplete, it is still sufficient to find enough mimotopes for detecting the parent peptide in a database.

Although the present technology may be reminiscent of methods for screening phage libraries or approaches that use oligomerised soluble T cell receptors as detection tools (Crawford et al., 2006), there is a fundamental difference, because the present method does not dependent on high affinities of TCR-MHC/peptide interactions. Screening of phage libraries involves several panning steps, where reasonable affinities are a prerequisite. For usual applications of phage libraries, i.e. for investigating interactions of ligands with antibodies or receptors, the affinities are surely high enough. T cell receptors, by contrast, have notoriously low affinities: They are typically several orders of magnitude lower than those observed for antibodies. Even TCR-oligomerisation may not be able to overcome this disadvantage, because the readout of such an assay is still a binding assay with moderate sensitivity. This is presumably the reason why, as discussed above, a priori unknown T cell antigens have not yet been discovered by this technique. By contrast, the present invention makes use of an extremely sensitive bioassay: the activation of a cell, such as a T hybridoma cell, that just needs to be loosely attached to its antigen-presenting cell, is measured. The tremendous sensitivity of this assay compensates for the low binding affinity of the T cell receptor to its MHC/peptide complex.

The technology of the present invention may have several implications not only for scientific purposes, but also for medical applications. First, it is a generally applicable method, i.e., it may be applied to any T cell of interest. It is not restricted to human T cells, but the antigen recognition properties of any TCR from any species may be investigated. This is of course highly interesting for many scientific questions, where T cells are involved. Technically, the only proviso is that the specific class-I MHC molecule is known, or that the specific class-II MHC molecule is known. If this is not the case, then the complete set of all candidate alleles has to be identified in a preceding experiment, using methods well established in the art (Robinson J, et al. (2003); http://www.ebi.ac.uk/imgt/hla/citations.html; Bettinotti et al. (2003); Marsh et al (2010)). Then all candidate HLA alleles can be tested by the method provided here. Further, there is no need to generate primary cells, neither T cells, nor antigen presenting cells, which may often be highly problematic, in particular if human samples are investigated.

The most important perspective, however, is in the medical field: T cells are involved in many diseases. They defeat infections and tumours, and they attack "self" tissue in autoimmunity. In most cases their precise antigens are not known. Knowing these epitopes will enable scientists to utilise this knowledge in diagnostics and therapy. Thus, the antigens may serve as biomarkers to detect infections and tumours and to improve diagnosis of many autoimmune diseases. Further, such biomarkers may be of great prognostic value for the progression of diseases. Knowing the antigens may also be helpful in therapeutic approaches: They could be used in vaccinations against infections or tumours (Boon et al., 2006), and they may allow to selectively delete or modulate auto-aggressive T cell clones in many autoimmune diseases, where e.g. CD8+ T cells are known to play prominent roles, i.e. in multiple sclerosis, psoriasis, inflammatory myopathies and many others more (Friese and Fugger, 2009; Dalakas, 2006; Walter and Santamaria, 2005).

Further, knowledge of the antigens may allow the rational design and development of new, improved T cell receptors that are engineered for higher affinities to their target antigens. Such improved T cell receptors may be produced by replacement or introduction of amino acids in the complementarity determining regions by site-specific mutagenesis. The improved T cell receptors may be used for detection of their antigens in vitro and in vivo for scientific, diagnostic and therapeutic purposes. They may be used to detect, block, or delete (by coupling toxic substances) cells that present certain antigens. If required, T cell receptors may be oligomerized to increase avidity. Thus, in an alternative embodiment, the present invention also refers to engineered T cell receptors, wherein amino acids are altered as compared to a natural T cell receptor and wherein said alteration results in an increased affinity to the target antigen as compared to the unaltered T cell receptor.

In addition, the knowledge of specific antigens may also allow the design of altered peptide ligands for a particular T cell receptor of interest. Such altered antigens may be of importance for inducing T cell tolerance or improving the immunogenicity of a particular antigen vaccine. Methods for the rational design of altered and/or improved T cell antigens are well known in the art (Fontoura et al. (2005); Bielekova and Martin (2001)).

In a preferred embodiment, the method of the invention comprises repeating steps (a) to (c) of the above defined method until a single molecular type of nucleic acid molecule encoding a single type of antigen is isolated. Thus, steps (a) to (c) may be repeated at least one more time, such as for example two more times, three more times, four more times, five more times, six more times, seven more times, eight more time, nine more times or ten more times. A higher number of repeats of steps (a) to (c) is also envisaged herein.

Employing standard methods of introducing the peptide library into the antigen-presenting cells of (ab) may result in the presence of more than one copy of the encoding nucleic acid molecule within said cell. Furthermore, nucleic acid molecules present in the culture medium may be transferred together with the antigen-presenting cell when isolating said cell in step (c). Thus, performing the method of the invention with only one round of steps (a) to (c) may result in the isolation of an antigen-presenting cell that carries multiple diverse copies of nucleic acid molecules encoding different antigen peptides or to which multiple diverse copies of nucleic acid molecules encoding different antigen peptides are attached. By repeating steps (a) to (c), the correct target antigen may be identified in the subsequent step (d). It is understood that when repeating step (a), the antigen-presenting cell is a cell carrying the nucleic acid molecules isolated from the antigen-presenting cell isolated in step (c) in the previous round of screening.

Figure 6:
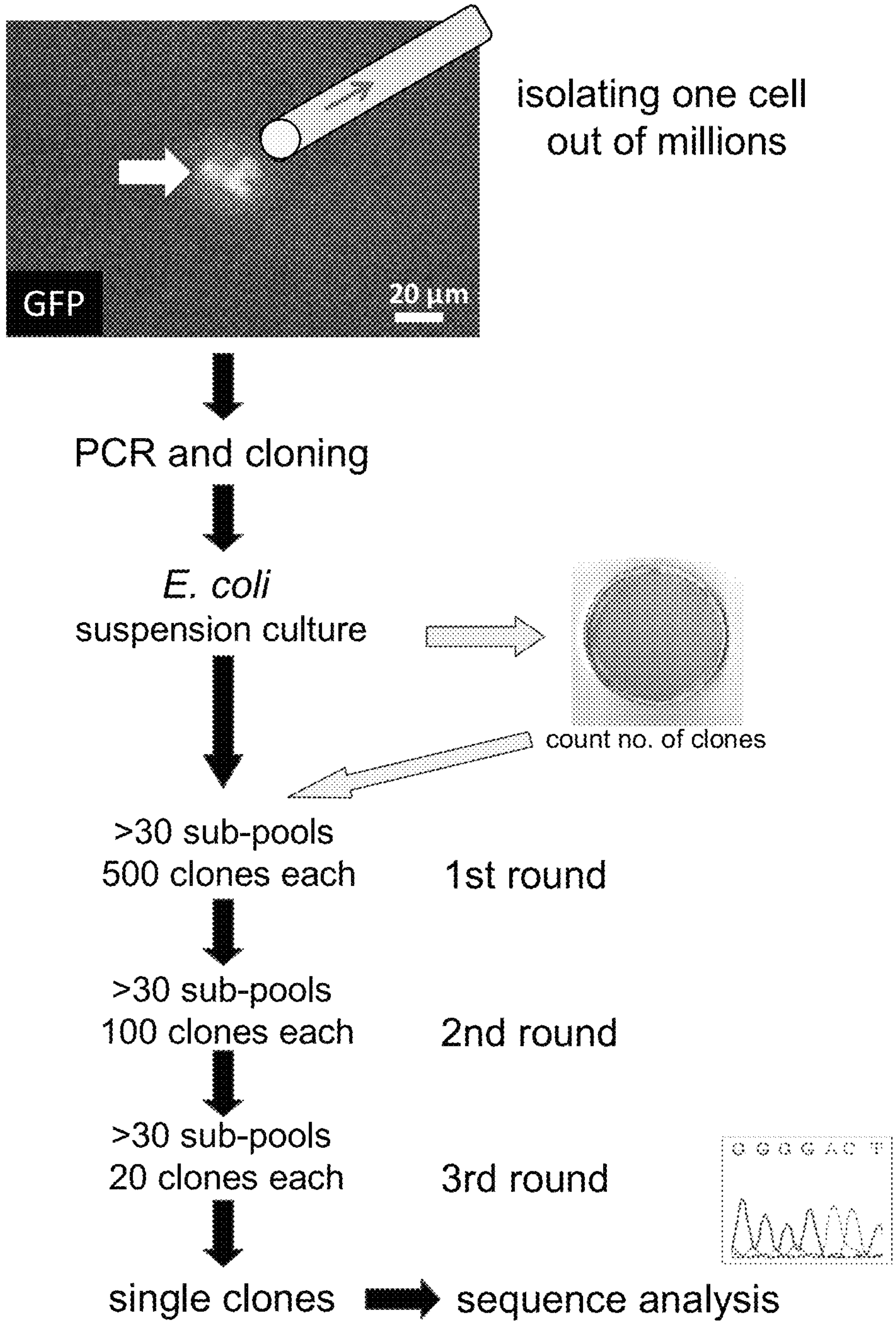

FIG. 6 below provides an overview over a preferred way of carrying out these repeated method steps in order to obtain a single molecular type of nucleic acid molecule encoding a single type of antigen. In brief, in a first step an activated, green fluorescent TCR-transfectant is picked together with the subjacent antigen presenting cell that carries the activating plasmid. The inserts of the plasmids are cloned, and transfected into bacteria. To count the numbers of bacterial clones, a fraction of the bacterial clones is plated onto agar plates. Then 30 or more sub-pools of bacteria are created that contain 500 independent bacterial clones, each. They are transfected into COS-7 cells and tested again. From a positive sub-pool, further sub-pools are generated, which contain less clones per sub-pool. Finally, single bacterial clones are analyzed. Positive clones are sequenced and reveal the antigenic mimotope.

In another preferred embodiment, the cells of (aa) further express CD8 chains, more preferably CD8 α and β chains.

The additional expression of CD8 on the cells of (aa) serves as a co-receptor for the T cell receptor (TCR). The extracellular IgV-like domain of CD8-α interacts with the $\alpha_3$ portion of Class I MHC molecules. This interaction keeps the cell expressing the T cell receptor closely together with the target cell bound during antigen-specific activation. Thus, additional expression of CD8 on the cells of (aa) further enhances the interaction between the two cells in accordance with the invention.

In another preferred embodiment of the method of the invention, the identification of the target antigen in (d) comprises sequencing of the nucleic acid molecule encoding said target antigen.

Methods for sequencing comprise, without being limiting, approaches of sequence analysis by direct sequencing, fluorescent SSCP in an automated DNA sequencer and pyrosequencing. These methods are well known in the art, see e.g. Adams et al. (Ed.), "Automated DNA Sequencing and Analysis", Academic Press, 1994; Alphey, "DNA Sequencing: From Experimental Methods to Bioinformatics", Springer Verlag Publishing, 1997; Ramon et al., J. Transl. Med. 1 $(2003)_9$; Meng et al., J. Clin. Endocrinol. Metab. 90 (2005) 3419-3422.

In a more preferred embodiment, the nucleic acid molecule encoding said target antigen is amplified prior to sequencing.

Techniques for amplifying nucleic acid molecules include, but are not limited to, PCR and its various modifications such as RT-PCR (also referred to as reverse transcriptase-PCR). PCR is well known in the art and is employed to make large numbers of copies of a target sequence. This is done on an automated cycler device, which can heat and cool containers with the reaction mixture in a very short time. The PCR, generally, consists of many repetitions of a cycle which consists of: (a) a denaturing step, which melts both strands of a DNA molecule and terminates all previous enzymatic reactions; (b) an annealing step, which is aimed at allowing the primers to anneal specifically to the melted strands of the DNA molecule; and (c) an extension step, which elongates the annealed primers by using the information provided by the template strand. Generally, PCR can be performed for example in a 50 μl reaction mixture containing 5 μl of 10×PCR buffer with 1.5 mM MgCl2, 200 μM of each deoxynucleoside triphosphate, 0.5 μl of each primer (10 μM), about 10 to 100 ng of template DNA and 1 to 2.5 units of Taq Polymerase. The primers for the amplification may be labelled or be unlabelled. DNA amplification can be performed, e.g., with a model 2400 thermal cycler (Applied Biosystems, Foster City, Calif.): 2 min at 94° C., followed by 30 to 40 cycles consisting of annealing (e.g. 30 s at 50° C.), extension (e.g. 1 min at 72° C., depending on the length of DNA template and the enzyme used), denaturing (e.g. 10 s at 94° C.) and a final annealing step at 55° C. for 1 min as well as a final extension step at 72° C. for 5 min. Suitable polymerases for use with a DNA template include, for example, *E. coli* DNA polymerase I or its Klenow fragment, T4 DNA polymerase, Tth polymerase, Taq polymerase, a heat-stable DNA polymerase isolated from *Thermus aquaticus* Vent, Amplitaq, iProof, Pfu and KOD, some of which may exhibit proof-reading function and/or different temperature optima. However, the person skilled in the art knows how to optimize PCR conditions for the amplification of specific nucleic acid molecules with primers of different length and/or composition or to scale down or increase the volume of the reaction mix. The "reverse transcriptase polymerase chain reaction" (RT-PCR) is used when the nucleic acid to be amplified consists of RNA. The term "reverse transcriptase" refers to an enzyme that catalyzes the polymerization of deoxyribonucleoside triphosphates to form primer extension products that are complementary to a ribonucleic acid template. RT-PCR is particularly suitable when RNA viruses are employed in order to encode the library plasmids for use in the method of the invention. The enzyme initiates synthesis at the 3'-end of the primer and proceeds toward the 5'-end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. High-temperature RT provides greater primer specificity and improved efficiency. U.S. patent application Ser. No. 07/746, 121, filed Aug. 15, 1991, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, can be used for all primer extension steps, regardless of template. Both processes can be done without having to open the tube to change or add reagents; only the temperature profile is adjusted between the first cycle (RNA template) and the rest of the amplification cycles (DNA template). The RT Reaction can be performed, for example, in a 20 μl reaction mix containing: 4 μl of 5× AMV-RT buffer, 2 μl of Oligo dT (100 μg/ml), 2 μl of 10 mM dNTPs, 1 μl total RNA, 10 Units of AMV reverse transcriptase, and $H_2O$ to 20 μl final volume. The reaction may be, for example, performed by using the following conditions: The reaction is held at 70 C.° for 15 minutes to allow for reverse transcription. The reaction temperature is then raised to 95 C.° for 1 minute to denature the RNA-cDNA duplex. Next, the reaction temperature undergoes two cycles of 95° C. for 15 seconds and 60 C.° for 20 seconds followed by 38 cycles of 90 C.° for 15 seconds and 60 C.° for 20 seconds. Finally, the reaction temperature is held at 60 C.° for 4 minutes for the final extension step, cooled to 15 C.°, and held at that temperature until further processing of the amplified sample. Any of the above mentioned reaction conditions may be scaled up according to the needs of the particular case.

Suitable primers for both the sequencing as well as the amplification of nucleic acid molecules can be derived by the skilled person using well-established methods. For example, primer sequences may be derived based on the knowledge of up-stream and down-stream flanking regions surrounding the randomised nucleic acid sequences encoding the peptide libraries, such as for example the plasmid backbone into which said nucleic acid sequences are inserted to, the promoter sequence employed to express the peptides or other regulatory sequences, such as enhancer sequences.

In a further preferred embodiment of the method of the invention, the identification of the target antigen in (d) comprises the identification of at least one mimotope of the antigen.

The term "mimotope", in accordance with the present invention, relates to a molecule, which mimics the structure of an antigen epitope. Said molecule may, for example, be a peptide. Due to the mimicking property the mimotope causes a T cell receptor response identical to the one elicited by the naturally occurring antigen epitope. A T cell receptor recognizing a particular antigen epitope will thus also recognize a mimotope which mimics that antigen epitope. Preferably, a mimotope differs from the natural target antigen epitope of a particular T cell receptor in its amino acid structure, e.g. the amino acid sequence and composition, such as for example by a difference of less than 40 amino acids in amino acids structure, such as for example less than 30 amino acids, less than 20 amino acids, less than 15 amino acids less than 10 amino acids, less than 5 amino acids, less than 4 amino acids, less than 3 amino acids and most preferably by one amino acid.

"At least one mimotope", as used herein, refers to any number of possible mimotopes for a given antigen. It includes, for example, at least two mimotopes, such as for example at least three, at least four, at least five, at least six, at least seven, at least eight, at least nine or at least 10 mimotopes. Also included is at least 15, such as at least 20, at least 30, at least 40, at least 50, at least 75, at least 100, at least 150, at least 200, at least 300, at least 400 or at least 500 mimotopes.

This embodiment is based on the finding that it is possible to identify mimotopes by the method of the present invention, which may then be employed in a database search to identify the naturally occurring antigen. Thus, even if the actual antigen is not directly identified by the method of the invention, it can indirectly be identified via said mimotopes, as described in the examples below.

In another preferred embodiment of the method of the invention, the antigen-presenting cells are cells capable of amplifying the peptide libraries.

The term "cells capable of amplifying the peptide libraries", as used herein, refers to cells capable to replicate the nucleic acid sequences or the vector. Such cells are well known in the art. Non-limiting examples include cells comprising the large T antigen when employing plasmids having a SV40 origin as described above; cells comprising the EBNA system as described in Durocher et al. (2002) or cells that are suited to be transformed by a virus, such as for example a retrovirus, adenovirus or lentivirus, which may host and amplify such retroviral vectors (Smith et al. (2001). Also cells not endogenously expressing said systems may be employed, in which case the cells may simply be transfected or transformed with the required components of the respective system, for example with the large T antigen.

A suitable degree of amplification, in accordance with the present invention, is achieved when more copies of the nucleic acid sequences are present in the cell than were originally transfected or transformed into said cell. Thus, amplification is achieved when the amount of nucleic acid sequence copies is at least duplicated, such as for example when at least 5% more copies of one molecular species of nucleic acid sequence is present in the cell, such as for example at least 10% more copies, such as at least 20% more copies, at least 30% more copies, at least 50% more copies, at least 100% more copies, at least 200% more copies, at least 500% more copies, at least 1.000% more copies, at least 2.000% more copies, at least 3.000% more copies, at least 4.000% more copies, at least 5.000% more copies, at least 10.000% more copies, at least 15.000% more copies, at least 50.000% more copies, at least 100.000% more copies, at least 250.000% more copies or at least 500.000% more copies.

In order to verify whether a particular cell is capable of amplifying the peptide libraries, some of said cells may be analysed immediately after transfection/transformation for the amount of copies of one molecular type of the nucleic acid sequence. In addition, the same analysis may be repeated with cells obtained at (a) later time point(s) and the copy numbers thus determined may be compared. Methods for the quantitative or semi-quantitative determination of copy numbers of any given nucleic acid sequence are well known in the art and include, without being limiting, PCR methods as described elsewhere herein.

In a more preferred embodiment, the antigen-presenting cells are selected from the group consisting of COS-7, HEK, Hela, H9, Jurkat, NIH3T3, C127, COS-1, CV1, QC1-3, mouse L cells, mouse C2C12 cells and Chinese hamster ovary (CHO), Wi-38, MRC-5, insect cells like Sf9, Hi-5 cells.

In another preferred embodiment, the read-out system comprises the activation of a reporter protein.

The term "reporter protein", as used herein, refers to a protein that is expressed in response to a certain stimulus to be investigated and that can easily be detected. Thus, in accordance with the present invention, it is preferred that the reporter protein is expressed upon T cell activation. A reporter protein preferably is a protein that is easy to detect and, more preferably, it is a protein that is not present normally in the cells investigated. Non-limiting examples of reporter proteins include: β-galactosidase (encoded by the bacterial gene lacZ), luciferase, such as for example bacterial luciferase (luxAB), *Photinus luciferase* and *Renilla luciferase*, chloramphenicol acetyltransferase (CAT; from bacteria), GUS (β-glucuronidase; commonly used in plants) as well as green fluorescent protein (GFP; from jelly fish) and variants thereof, such as CFP, YFP, EGFP, GFP+. Further non-limiting examples include alkaline phosphatase or secreted alkaline phosphatase, peroxidase, β-xylosidase, XyIE (catechol dioxygenase), TreA (trehalase) as well as coral-derived photoproteins including DSRed, HcRed, AmCyan, ZsGreen, ZsYellow, AsRed.

Furthermore, the reporter protein may be a protein that confers resistance to an antibiotic. In this case, it is preferred that the cells be cultivated in the presence of an antibiotic so that only clones expressing the reporter protein are capable of propagating. Generally, the protein can mediate resistance to an antibiotic such as hygromycin, geneticin (G418), puromycin, blasticidine, zeocin, histidinol, methotrexate, media with xanthine/hypoxynthin-aminopterin-mycophenolic (Gpt selection), HAT selection, indole media without tryptopha, or phleomycin. (R. Vile (1991) Meth Mol. Biol. 8:49-60)

In a more preferred embodiment, the reporter protein is selected from the group consisting of fluorescent compounds, bioluminescent compounds and chemiluminescent compounds.

More preferably, the reporter protein is selected from the group consisting of GFP and variants of GFP such as CFP, YFP, EGFP, GFP+, sGFP, bacterial luciferase (luxAB), *Photinus luciferase, Renilla luciferase* and coral-derived photoproteins including DSRed, HcRed, AmCyan, ZsGreen, ZsYellow, AsRed.

The present invention further relates to a method of identifying nucleic acid molecules encoding variable, hypervariable and/or joining regions of T cell receptor β chains, comprising amplifying said nucleic acid molecules obtained from T cells expressing αβ T cell receptors using a primer or a set of primers selected from the primers represented by SEQ ID NOs: 1 to 9.

The definitions as well as the preferred embodiments provided herein above with regard to the other methods of the invention apply mutatis mutandis also to this method of identifying nucleic acid molecules encoding T cell receptor β chains as well as to the preferred embodiments thereof described herein below.

Preferably, the T cells are single T cells, i.e. individual T cells or clonal expansions of individual T cells. In other words, the T cells represent one molecular type of cell only.

In accordance with this method of the invention, nucleic acid molecules are obtained from T cells using methods well known in the art, e.g. as described elsewhere herein.

The term "set", as used herein, relates to a combination of primers. The set of primers of the present invention requires that more than one molecular species of primer is present. Thus, at least two different primers, such as at least three, at least four, at least five, at least six, at least seven, at least eight or at least nine different primers selected from the primers represented by SEQ ID NOs: 1 to 9 are comprised in the set of primers.

Figure 8:
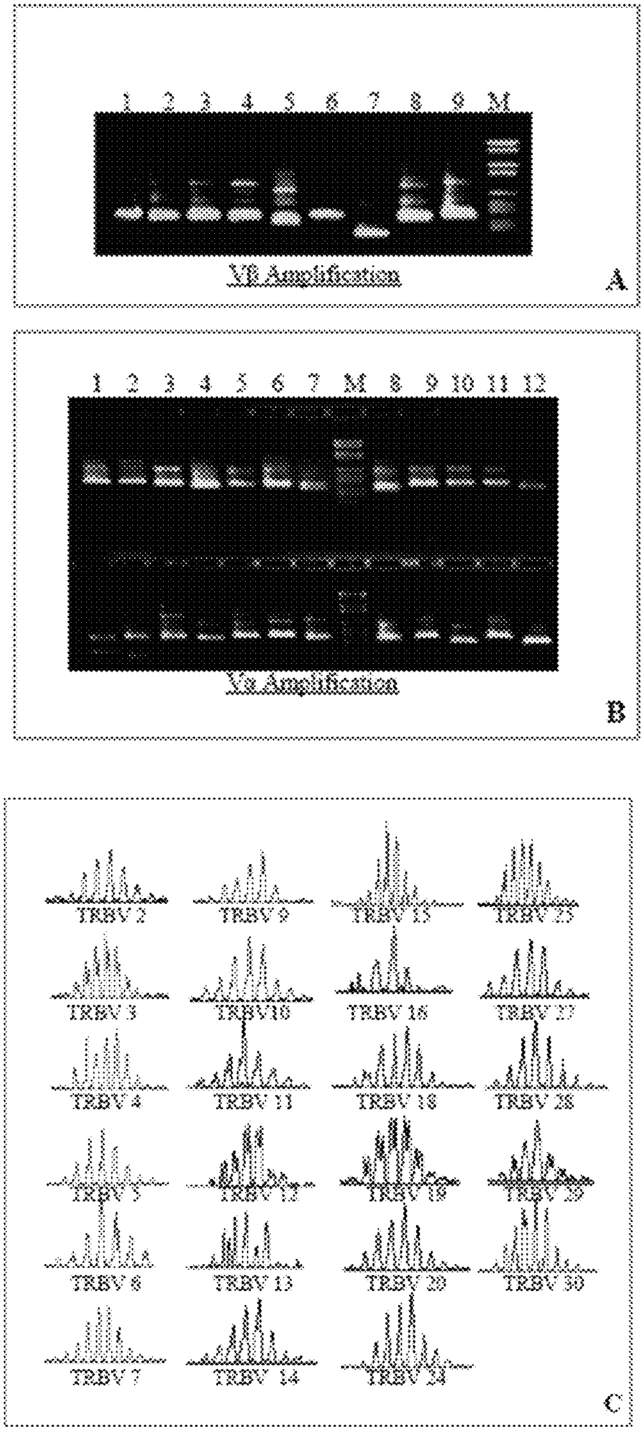

In accordance with the present invention, T cell receptor Vβ-primers were identified based on sequence homologies of the various functional Vβ-gene families. The primer positions are such that direct sequencing can identify the respective TCR Vβ-gene. In addition, these primers for the Vβ repertoire are adjusted to each other as well as to a set of 24 Vα-primers in order to minimize potential interactions during PCR amplification. The set of nine Vβ primers (Vp1-9, Table 1) covers all functional Vβ genes. Except Vp1, which is located in the leader segment, all primers are positioned in the Vβ-gene segment. In combination with a Cβ(out)-primer (SEQ ID NO: 11) each of these primers efficiently amplifies the corresponding Vβ-gene rearrangements, as shown by agarose gel-electrophoresis and ethidium-bromide staining (FIG. 8, A).

TABLE 1

Vβ Primers and TRBV subfamilies covered by Vp primers.

| Vp primer | Sequence | SEQ ID NO: | TRBV family | Basepairs |
|---|---|---|---|---|
| Vp1 | 5'-TSY TTT GTC TCC TGG GAG CA-3' | 1 | 5, 9, 13, 14, 19 | 29-48 |
| Vp2 | 5'-CCT GAA GTC GCC CAG ACT CC-3' | 2 | 2, 16 | 4-23 |
| Vp3 | 5'-GTC ATS CAG AAC CCA AGA YAC C-3' | 3 | 15, 18 | 10-31 |
| Vp4 | 5'-GGW TAT CTG TMA GMG TGG AAC CTC-3' | 4 | 20, 29 | 30-53 |
| Vp5 | 5'-ATG TAC TGG TAT CGA CAA GAY C-3' | 5 | 6, 10, 24, 25, 27, 28 | 94-115 |
| Vp6 | 5'-CAC TGT GGA AGG AAC ATC AAA CC-3' | 6 | 30 | 69-91 |
| Vp7 | 5'-TCT CCA CTC TSA AGA TCC AGC-3' | 7 | 7, 11, 12 | 221-241 |
| Vp8 | 5'-CAG RAT GTA RAT YTC AGG TGT GAT CC-3' | 8 | 7 | 50-75 |
| Vp9 | 5'-CCA GAC WCC AAR AYA CCT GGT CA-3' | 9 | 3, 4 | 15-37 |

The nomenclature of degenerate basepairs relates to the IUPAC nomenclature of mixed bases. Examples: S=C or G; Y=T or C; W=T or A; M=C or A; R=A or G; K=G or T; V=A or C or G; H=A or T or C; D=A or T or G; B=T or C or G; N=A or T or C or G (Cornish-Bowden A: IUPAC-IUB symbols for nucleotide nomenclature. *Nucleic Acids Res* 1985, 13:3021-3030.).

In a preferred embodiment of the method of identifying nucleic acid molecules encoding T cell receptor β chains, the amplification further comprises the use of a Cβ(out)-primer (SEQ ID NO: 11).

TABLE 2

| C primer and universal primer (UP). | | |
|---|---|---|
| C primer | Sequence | SEQ ID NO: |
| Cα out | 5'-GCA GAC AGA CTT GTC ACT GG-3' | 10 |
| Cβ out | 5'-TGG TCG GGG AAG AAG CCT GTG-3' | 11 |
| Cα in | 5'-AG TCT CTC AGC TGG TAC ACG-3' | 12 |
| UP | 5'-ACA GCA CGA CTT CCA AGA CTC A-3' | 13 |
| Cβ in | 5'-TCT GAT GGC TCA AAC ACA GC-3' | 14 |

In a further preferred embodiment of the method of identifying nucleic acid molecules encoding T cell receptor β chains, the method further comprises identifying the nucleic acid molecules encoding the variable, hypervariable and/or joining regions of matching T cell receptor α chains by amplifying said nucleic acid molecules using a primer or a set of primers selected from the primers represented by SEQ ID NOs: 15 to 38.

The 24 T cell receptor Vα-primers represented by SEQ ID NOs: 15 to 38 have been recently described for the amplification of the TCR Vα repertoire (Seitz, Schneider et al. 2006) and are shown in Table 3.

TABLE 3

| Vα primers. | | |
|---|---|---|
| Vp primer | Sequence | SEQ ID NO: |
| Vα-1$^{14}$-for-out | 5'-AGS AGC CTC ACT GGA GTT G-3' | 15 |
| Vα-1$^{235}$-for-out | 5'-CTG AGG TGC AAC TAC TCA TC-3' | 16 |
| Vα-2-for-out | 5'-CAR TGT TCC AGA GGG AGC C-3' | 17 |
| Vα-3,25-for-out | 5'-GAA RAT GYC WCC ATG AAC TGC-3' | 18 |
| Vα-4,20-for-out | 5'-WTG CTA AGA CCA CCC AGC C-3' | 19 |
| Vα-5-for-out | 5'-AGA TAG AAC AGA ATT CCG AGG-3' | 20 |
| Vα-6,14-for-out | 5'-RYT GCA CAT ATG ACA CCA GTG-3' | 21 |
| Vα-7-for-out | 5'-CAC GTA CCA GAC ATC TGG G-3' | 22 |
| Vα-8,21-for-out | 5'-CCT GAG YGT CCA GGA RGG -3' | 23 |
| Vα-9-for-out | 5'-GTG CAA CTA TTC CTA TTC TGG-3' | 24 |
| Vα-10,24-for-out | 5'-AST GGA GCA GAG YCC TCA G-3' | 25 |
| Vα-11-for-out | 5'-TCT TCA GAG GGA GCT GTG G-3' | 26 |
| Vα-12-for-out | 5'-GGT GGA GAA GGA GGA TGT G-3' | 27 |
| Vα-13,19,26-for-out | 5'-SAA STG GAG CAG AGT CCT C-3' | 28 |
| Vα-15-for-out | 5'-CCT GAG TGT CCG AGA GGG-3' | 29 |
| Vα-16-for-out | 5'-ATG CAC CTA TTC AGT CTC TGG-3' | 30 |
| Vα-17-for-out | 5'-TGA TAG TCC AGA AAG GAG GG-3' | 31 |
| Vα-18-for-out | 5'-GTC ACT GCA TGT TCA GGA GG-3' | 32 |
| Vα-22,31-for-out | 5'-CCC TWC CCT TTT CTG GTA TG-3' | 33 |
| Vα-23,30-for-out | 5'-GGC ARG AYC CTG GGA AAG G-3' | 34 |
| Vα-27-for-out | 5'-CTG TTC CTG AGC ATG CAG G-3' | 35 |
| Vα-28-for-out | 5'-AGA CAA GGT GGT ACA AAG CC-3' | 36 |
| Vα-29-for-out | 5'-CAA CCA GTG CAG AGT CCT C-3' | 37 |
| Vα-32-for-out | 5'-GCA TGT ACA AGA AGG AGA GG-3' | 38 |

The nomenclature of degenerate basepairs relates to the IUPAC nomenclature of mixed bases. Examples: S = C or G; Y = T or C; W = T or A; M = C or A; R = A or G; K = G or T; V = A or C or G; H = A or T or C; D = A or T or G; B = T or C or G; N = A or T or C or G (Cornish-Bowden A: IUPAC-IUB symbols for nucleotide nomenclature. *Nucleic Acids Res* 1985, 13: 3021-3030.).

In a preferred embodiment, the amplification further comprises the use of a Cα out-primer (SEQ ID NO: 10).

In a more preferred embodiment of the method of identifying nucleic acid molecules encoding T cell receptor β chains, the method comprises the steps: (i) amplifying nucleic acid molecules using a set of primers comprising (a) the primers represented by SEQ ID NOs: 1 to 9; and/or (b) the primers represented by SEQ ID NOs: 15 to 38; (ii) amplifying the reaction product of (i)(a) using a set of primers comprising the primers represented by SEQ ID NOs: 39 to 47; and/or (iii-a) amplifying the reaction product of (ii) using (a) the primer of SEQ ID NO: 13; and (b) the primer of SEQ ID NO: 14 and/or (iii-b) amplifying the reaction product of (i)(b) using (a) a set of primers represented by SEQ ID NOs: 48 to 83 and (b) the primer of SEQ ID NO: 12.

TABLE 4

Vp+ primers.

| Vp+ primer | Sequence | SEQ ID NO: |
|---|---|---|
| Vp1+ | 5'-ACAGCACGACTTCCAAGACTCA CYTTTGTCTCCTGGGAGCA-3' | 39 |
| Vp2+ | 5'-ACAGCACGACTTCCAAGACTCA CCTGATGTCGCCCAGACTCC-3' | 40 |
| Vp3+ | 5'-ACAGCACGACTTCCAAGACTCA GTCATSCAGAACCCAAGAYACC-3' | 41 |
| Vp4+ | 5'-ACAGCACGACTTCCAAGACTCA GGWTATCTGTMAGMGTGGAACCTC-3' | 42 |
| Vp5+ | 5'-ACAGCACGACTTCCAAGACTCA ATGTACTGGTATCGACAAGAYC-3' | 43 |
| Vp6+ | 5'-ACAGCACGACTTCCAAGACTCA CACTGTGGAAGGAACATCAAACC-3' | 44 |
| Vp7+ | 5'-ACAGCACGACTTCCAAGACTCA TCTCCACTCTSAAGATCCAGC-3' | 45 |
| Vp8+ | 5'-ACAGCACGACTTCCAAGACTCA CAGRATGTARATYTCAGGTGTGATCC-3' | 46 |
| Vp9+ | 5'-ACAGCACGACTTCCAAGACTCA TCAGACWCCAARAYACCTGGTCA-3' | 47 |

The nomenclature of degenerate basepairs relates to the IUPAC nomenclature of mixed bases. Examples: S = C or G; Y = T or C; W = T or A; M = C or A; R = A or G; K = G or T; V = A or C or G; H = A or T or C; D = A or T or G; B = T or C or G; N = A or T or C or G (Cornish-Bowden A: IUPAC-IUB symbols for nucleotide nomenclature. *Nucleic Acids Res* 1985, 13: 3021-3030.).

TABLE 5

Vα nested primers and preferred sets thereof.

| | Vp+ primer | Sequence | SEQ ID NO: |
|---|---|---|---|
| Set 1 | Vα-4/1-for-in | 5'-ACA GAA GAC AGA AAG TCC AGC-3' | 48 |
| | Vα-4/2-for-in | 5'-GTC CAG TAC CTT GAT CCT GC-3' | 49 |
| | Vα-6-for-in | 5'-GCA AAA TGC AAC AGA AGG TCG-3' | 50 |
| | Vα-8/1-for-in | 5'-CAG TGC CTC AAA CTA CTT CC-3' | 51 |
| | Vα-8/2-for-in | 5'-GCC TCA GAC TAC TTC ATT TGG-3' | 52 |
| | Vα-14-for-in | 5'-ACA GAA TGC AAC GGA GAA TCG-3' | 53 |
| | Vα-24-for-in | 5'-CCT TCA GCA ACT TAA GGT GG-3' | 54 |
| | Vα-28-for-in | 5'-TCT CTG GTT GTC CAC GAG G-3' | 55 |
| Set 2 | Vα-2/1-for-in | 5'-TGG AAG GTT TAC AGC ACA GC-3' | 56 |
| | Vα-2/2-for-in | 5'-TGG AAG GTT TAC AGC ACA GG-3' | 57 |
| | Vα-5-for-in | 5'-CAG CAT ACT TAC AGT GGT ACC-3' | 58 |
| | Vα-10-for-in | 5'-TCA CTG TGT ACT GCA ACT CC-3' | 59 |
| | Vα-12-for-in | 5'-TAC AAG CAA CCA CCA AGT GG-3' | 60 |
| | Vα-22-for-in | 5'-AGG CTG ATG ACA AGG GAA GC-3' | 61 |
| | Vα-31-for-in | 5'-GTG GAA TAC CCC AGC AAA CC-3' | 62 |
| Set 3 | Vα-7-for-in | 5'-CTC CAG ATG AAA GAC TCT GC-3' | 63 |
| | Vα-13-for-in | 5'-TTA AGC GCC ACG ACT GTC G-3' | 64 |
| | Vα-17-for-in | 5'-CTG TGC TTA TGA GAA CAC TGC-3' | 65 |
| | Vα-18-for-in | 5'-CC TTA CAC TGG TAC AGA TGG-3' | 66 |
| | Vα-21-for-in | 5'-TGC TGA AGG TCC TAC ATT CC-3' | 67 |
| | Vα-23-for-in | 5'-GTG GAA GAC TTA ATG CCT CG-3' | 68 |
| | Vα-32-for-in | 5'-TCA CCA CGT ACT GCA ATT CC-3' | 69 |
| Set 4 | Vα-3-for-in | 5'-TTC AGG TAG AGG CCT TGT CC-3' | 70 |
| | Vα-11-for-in | 5'-AGG GAC GAT ACA ACA TGA CC-3' | 71 |
| | Vα-15-for-in | 5'-CCT CCA CCT ACT TAT ACT GG-3' | 72 |
| | Vα-19-for-in | 5'-CCT GCA CAT CAC AGC CTC C-3' | 73 |
| | Vα-25-for-in | 5'-AGA CTG ACT GCT CAG TTT GG-3' | 74 |
| | Vα-26-for-in | 5'-CCT GCA TAT CAC AGC CTC C-3' | 75 |
| | Vα-29-for-in | 5'-ACT GCA GTT CCT CCA AGG C-3' | 76 |

TABLE 5-continued

| Vα nested primers and preferred sets thereof. | | | |
|---|---|---|---|
| | Vp+ primer | Sequence | SEQ ID NO: |
| Set 5 | Vα-1/235-for-in | 5'-AAG GCA TCA ACG GTT TTG AGG-3' | 77 |
| | Vα-1/14-for-in | 5'-CTG AGG AAA CCC TCT GTG C-3' | 78 |
| | Vα-9-for-in | 5'-ATC TTT CCA CCT GAA GAA ACC-3' | 79 |
| | Vα-16-for-in | 5'-TCC TTC CAC CTG AAG AAA CC-3' | 80 |
| | Vα-20-for-in | 5'-ACG TGG TAC CAA CAG TTT CC-3' | 81 |
| | Vα-27-for-in | 5'-ACT TCA GAC AGA CTG TAT TGG-3' | 82 |
| | Vα-30-for-in | 5'-CTC TTC ACC CTG TAT TCA GC-3' | 83 |

Figure 9:
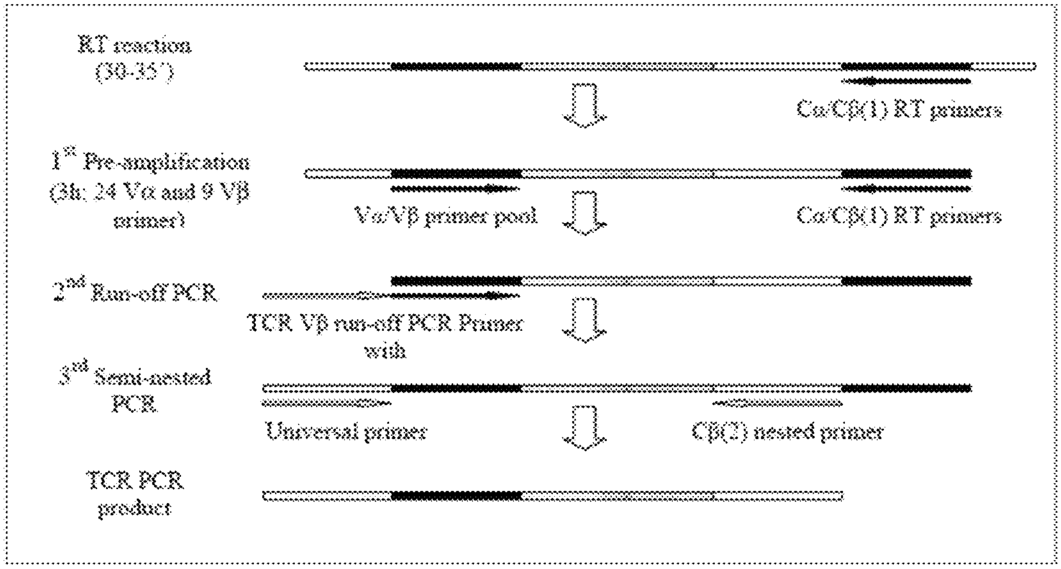

The above described method allows in a first step (step (i)) to simultaneously amplify all Vα- and/or β-chains from cDNA isolated from cells of interest by using a pool of primers comprising 24 Vα-specific and 9 Vβ-specific primers (Vp1-Vp9), which cover all functional α and β TCR variable region genes. In a second step, i.e. step (ii), the respective TCR Vβ-chain rearrangements are amplified from the pre-amplification product. Because the multitude of 23 different Vβ-gene subfamilies prohibits a Vβ-specific nested PCR in one sample, a universal primer sequence is introduced at the 5' end of the TCR β-chain PCR-products in step (ii). For this purpose a unique 21-nucleotide sequence was designed lacking primer interactions or homologies with human genes and appended to the 5' end of nine different Vp (Vp1-9) primers (referred to herein as Vp+ primers). Parts of the pre-amplification product is subjected to a run-off PCR using these elongated primers, followed by a third semi-nested PCR, which amplifies the respective single cell TCR-Vβ rearrangement independent from the TCR Vβ-gene family using the universal primer together with a nested Cβ (2)-primer (SEQ ID NO: 14) (step (iii-a)). This PCR strategy is shown in FIG. 9. In parallel or subsequently, the corresponding TCR Vα-rearrangements are amplified from the pre-amplification (i.e. step (i)) multiplex PCR in different nested PCRs (i.e. step (iii-b)). Preferably, only five different nested PCRs are carried out using five Vα-primer pools as shown in Table 5 instead of individual reactions, described by Seitz et al. The amplified TCR α- and β-chain rearrangements can then be characterized by direct sequencing.

In a preferred embodiment, the method described above is preceded by a step of reverse transcription of mRNA of cells, preferably a single cell or a clonally expanded single type of cell, into cDNA. Such methods of reverse transcription are well known and may be carried out, e.g. by using a one step RT-PCR kit (such as provided by QIAGEN) and gene specific Cα- and β-primers.

Molecular analysis of the paired αβ-TCR rearrangements of single T cells has to encompass the complete spectrum of approx. 70 TCR Vα- and approx. 50 TCR Vβ-region genes. In accordance with the present invention, a PCR strategy was established that can amplify all different Vβ-gene families of the TCR R-chain repertoire together with a set of 24 TCR Vα-primers recently described for the simultaneous amplification of the TCR Vα repertoire (Seitz, Schneider et al. 2006). The complexity of this approach results from potential interactions between the multitude of primers, which may interfere with specific amplification. In accordance with the present invention, a PCR protocol was established which starts with a multiplex RT-PCR capable of pre-amplifying all TCR Vα- and Vβ-genes in a single reaction. Subsequently, the TCR Vα- and Vβ-PCR products are handled separately.

The present invention further relates to a method of identifying patient-specific T cell antigens comprising (A) isolating T cells from a sample obtained from said patient; (B) identifying matching T cell receptor α and β chains from the T cells isolated in (A); and (C) identifying T cell antigens in accordance with the method of the invention, wherein the cell comprising a functional T cell receptor and a read-out system for T cell activation expresses the matching T cell receptor α and β chains identified in (B).

The definitions as well as the preferred embodiments provided herein above with regard to the method of the invention apply mutatis mutandis also to this patient-specific method of identifying T cell antigens.

In accordance with this patient-specific method of identifying T cell antigens, T cells are isolated from a patient. Methods for isolating T cells from patients are well known in the art and include, without being limiting the isolation of T cells by laser-micro-dissection from frozen tissue biopsy samples, by picking of living or dead cells from fresh biopsy specimens harbouring living cells by hand or by using a micromanipulator, by isolating cells using a FACSort apparatus, by ex vivo cloning by limiting dilution, with or without previous fusion of the cell with a suitable tumor cell line to generate immortalized hybridoma cells (Burgemeister R. (2005) J Histochem Cytochem. 53:409-12; Erickson H S et al. (2008) Methods Mol. Biol. 424:433-48; Dainiak M B et al. (2007) Adv Biochem Eng Biotechnol. 106:1-18; Tung J W et al. (2007) Clin Lab Med. 27:453-68).

In a subsequent step, the heterodimeric T cell receptors expressed in said cells are identified. Methods for identifying T cell receptors from T cells are known in the art and include, without being limiting, amplification of T cell receptor α- and β-chains by PCR using clone-specific primers, e.g. in cases where the sequence of one of the chains is known, for example by CDR3-spectratyping (Pannetier et al. (1995)) or by immunohistochemistry employing antibodies that recognize epitopes on the variable regions of the TCR, or amplification of T cell receptor α- and β-chains by PCR using one or more sets of PCR primers that allow the amplification of many different, e.g. unknown, TCR chains. Such methods include, without being limiting, the above described method of the invention for identifying nucleic acid molecules encoding variable, hypervariable and/or joining regions of T cell receptor α and β chains (for example employing the primers disclosed in Seitz et al. (2006) for α-chains, and the Vβ primers disclosed herein for the variable, hypervariable and/or joining regions of β-chains). Alternative sets of primers suitable for the identification of T cell receptors from T cells include, without being limiting, those disclosed in Genevee (1992); Monteiro et al. (1996); Roers et al. (2000); Gagne et al. (2000) or Zhou et al. (2006). The T cell receptor thus identified is then employed in the cell according to (aa) of the method of identifying a target antigen of T cells according to the invention and the inventive method is carried out as described above.

In a preferred embodiment, the T cells isolated from the patient represent one single molecular type of T cells. Furthermore, it is preferred that the T cell receptor isolated from these cells represents one single molecular type of T cell receptor. Furthermore, the embodiment may also relate to two different T-cell receptors expressed in a single cell, i.e. T-cell receptors with two different Vα-chains and one Vβ-chain and vice versa.

The main advantage of this inventive patient-specific antigen search technology is that it allows to transfer a highly complex in vivo situation to a straightforward in vitro condition. This is of outstanding interest, because many different cell types and many different T cells are present in an inflammatory lesion, but only few of them are relevant to disease pathogenesis or progression. A method to analyze individual T cells of particular interest in inflammatory autoimmune lesions has recently been described (Seitz et al., 2006). This allows to distinguish relevant T cells from irrelevant T cells in various in vivo settings: For example, relevant T cells may be auto-aggressive T cells in autoimmune diseases, tumor-infiltrating T cells in neoplastic diseases, or anti-viral T cells in infectious diseases. Irrelevant cells may be bystander cells that were non-specifically attracted into the inflammatory milieu, cells in blood vessels, or patrolling T cells during immune surveillance. Individual T cells of choice can, for example, be isolated by laser-micro-dissection from frozen tissue biopsy samples or other methods for single cell isolation such as described above, their matching TCR α- and β-chains are cloned and expressed in $58\alpha^-\beta^-$ T hybridoma cells. Using this detection method in combination with the antigen search technology described herein, it will be possible to characterise the antigens of putatively pathogenic or beneficial T cells in a straightforward, quick, and cheap high-throughput assay. Using such T cell receptor transfected hybridoma cells provides the advantage that unlike other strategies where "real" T cells or T cell lines are used, there are virtually no limitations in cell numbers, because the hybridoma cells grow fast and reliable.

In a preferred embodiment of the patient-specific method of identifying T cell antigens, the matching T cell receptor α and β chains are identified in step (B) by identifying the nucleic acid molecules encoding variable, hypervariable and/or joining regions of said T cell receptor α and β chains according to the method of the invention described herein above.

As detailed in example 4 below, the method of the present invention employing the primers or sets of primers disclosed herein enables the identification of variable, hypervariable and/or joining regions of T cell receptor β chains in combination with matching α chains.

The present invention also relates to a composition comprising a T cell antigen identified by the method of the invention and/or the identified by the method of identifying a patient-specific T cell antigen of the invention.

The term "composition", as used in accordance with the present invention, relates to a composition which comprises at least one T cell antigen identified in accordance with the present invention. It may, optionally, comprise further molecules capable of altering the characteristics of the T cell antigen of the invention thereby, for example, stabilizing the T cell antigen. The composition may be in solid, liquid or gaseous form and may be, inter alia, in the form of (a) powder(s), (a) tablet(s), (a) solution(s) or (an) aerosol(s).

As mentioned herein above, the T cell antigens identified by the methods of the present invention may serve as biomarkers to detect infections and tumours and to improve diagnosis of autoimmune diseases and are of great prognostic value for the progression of diseases. Furthermore, said T cell antigens can be helpful in therapeutic approaches: They can be used in vaccinations against infections or tumours, and they may allow to selectively delete or modulate auto-aggressive T cell clones in autoimmune diseases, such as for example in multiple sclerosis, psoriasis, inflammatory myopathies and many others more. Thus, the composition of the invention may have a T cell activating activity, e.g. for use in vaccines, or it may have a T cell neutralising activity, e.g. for use in deletion of T cell clones.

In a preferred embodiment, the composition is a pharmaceutical composition.

In accordance with the present invention, the term "pharmaceutical composition" relates to a composition for administration to a patient, preferably a human patient. The pharmaceutical composition of the invention comprises the compounds, i.e. T cell antigens, recited above. The pharmaceutical composition of the present invention may, optionally and additionally, comprise a pharmaceutically acceptable carrier and/or excipient. By "pharmaceutically acceptable carrier and/or excipient" is meant a non-toxic solid, semisolid or liquid filler, diluent, encapsulating material or formulation auxiliary of any type. Examples of suitable pharmaceutical carriers and/or excipients are well known in the art and include sodium chloride solutions, phosphate buffered sodium chloride solutions, water, emulsions, such as oil/water emulsions, various types of wetting agents, sterile solutions, organic solvents including DMSO etc. Preferably the carrier/excipient is a parenteral carrier/excipient, more preferably a solution that is isotonic with the blood of the recipient. The carrier/excipient suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG. Conventional excipients include binding agents, fillers, lubricants and wetting agents. Preservatives and other additives may also be present such as, for example, antimicrobials, anti oxidants, chelating agents, and inert gases and the like. Furthermore, the pharmaceutical composition may comprise further agents depending on the intended use of the pharmaceutical composition. It is particularly preferred that said pharmaceutical composition comprises further agents known in the art to affect T cell activity, i.e. by either activating T cell activity for use in vaccines or by neutralising T cell activity for use in T cell neutralisation/depletion. Since the pharmaceutical preparation of the present invention relies on the above T cell antigens, it is preferred that the mentioned further agents are only used as a supplement, e.g. at a reduced dose as compared to the recommended dose when used as the only drug or in order to reduce the amount of T cell antigen required, so as to reduce side effects conferred by either the further agents or the T cell antigens.

The term "parenteral" as used herein refers to modes of administration which include intravenous, intramuscular, intra-peritoneal, intra-sternal, subcutaneous and intra-articular injection and infusion.

Compositions comprising such carriers and/or excipients can be formulated by well known conventional methods. Generally, the formulations are prepared by contacting the components of the pharmaceutical composition uniformly and intimately with liquid carriers/excipients or finely divided solid carriers/excipients or both. Then, if necessary, the product is shaped into the desired formulation.

These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. Generally, the regimen as a regular administration of the pharmaceutical composition should be in the range of 1 μg to 20 g units per day. However, a more preferred dosage might be in the range of 0.01 mg to 100 mg, even more preferably 0.01 mg to 50 mg and most preferably 0.01 mg to 10 mg per day. Administration of pharmaceutical compositions of the invention may be effected by different ways, e.g., by intravenous, intraperitoneal, subcutaneous, intramuscular, topical, intradermal, intranasal or intrabronchial administration.

The components of the pharmaceutical composition to be used for therapeutic administration must be sterile. Sterility is readily accomplished for example by filtration through sterile filtration membranes (e.g., 0.2 micron membranes).

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic water-for-injection.

In a more preferred embodiment, the pharmaceutical composition of the invention is for use in treating a disease selected from the group consisting of cancer, infections and autoimmune diseases.

"Cancer", in accordance with the present invention, refers to a class of diseases or disorders characterized by uncontrolled division of cells and the ability of these to spread, either by direct growth into adjacent tissue through invasion, or by implantation into distant sites by metastasis, where cancer cells are transported through the bloodstream or lymphatic system. Non-limiting examples of cancer include lymphoma, melanoma, lung cancer, and other tumors with tumor infiltrating lymphocytes.

The term "infections", as used herein, relates to the detrimental colonization of a host organism by a foreign species. In an infection, the infecting organism seeks to utilize the host's resources in order to multiply, usually at the expense of the host. The host's response to infection is inflammation.

Bacterial infections, in accordance with the present invention, include but are not limited to bacterial meningitis, cholera, diphtheria, listeriosis, pertussis (whooping cough), pneumococcal pneumonia, salmonellosis, tetanus, typhus, tuberculosis, *Streptococcus pyogenes, Staphylococcus aureus* or urinary tract infections by various microbial pathogens.

Viral infections, in accordance with the present invention, include but are not limited to mononucleosis, human immunodeficiency virus infection (HIV), chickenpox, common cold, cytomegalovirus infection, dengue fever, ebola haemorrhagic fever, hand-foot and mouth disease, hepatitis, influenza, mumps, poliomyelitis, rabies, smallpox, viral encephalitis, viral gastroenteritis, viral meningitis, viral pneumonia or yellow fever.

Fungal infections, in accordance with the present invention, include but are not limited to aspergillosis, blastomycosis, candidiasis, coccidioidomycosis, cryptococcosis, histoplasmosis or tinea pedis.

The term "autoimmune disease", in accordance with the present invention, refers to diseases which arise from overactive T-cell mediated immune responses of the body against substances and tissues normally present in the body. Autoimmune diseases are well known to the person skilled in the art and include, but are not limited to rheumatoid arthritis, multiple sclerosis, inflammatory bowel disease, diabetes mellitus type 1, psoriasis, autoimmune uveitis, autoimmune (Hashimoto) thyroiditis and Behcet's syndrome.

In another preferred embodiment, the composition of the invention is a diagnostic composition.

In accordance with the present invention, the term "diagnostic composition" relates to a composition for diagnosing individual patients for their potential response to or curability by the pharmaceutical compositions of the invention. The diagnostic composition of the invention comprises the T cell antigens recited above. The diagnostic composition may further comprise an appropriate carrier and/or excipient, as defined above. The diagnostic compositions may be packaged in a container or a plurality of containers.

As discussed above, the T cell antigens may be useful in a diagnostic composition as biomarkers to detect infections and tumours and to improve the diagnosis of autoimmune diseases. Furthermore, they are of prognostic value for monitoring the progression of such diseases.

Thus, in a further preferred embodiment, the diagnostic composition of the invention is for use in diagnosing a disease selected from the group consisting of cancer, infections and autoimmune diseases.

The present invention further relates to a peptide library, wherein the peptide library comprises a plurality of vectors comprising nucleic acid sequences encoding peptides, wherein the peptides are potential target antigens of T cells and wherein the nucleic acid sequences are randomised nucleic acid sequence.

The definitions as well as the preferred embodiments provided herein above with regard to the methods of the invention apply mutatis mutandis also to this peptide library.

The term "a plurality of vectors" relates to any number of vectors greater than 1. Thus, a plurality of vectors may be, for example, at least two vectors, such as five vectors, at least 10 vectors, at least 15 vectors, at least 20 vectors, at least 30 vectors, at least 40 vectors, at least 50 vectors, at 100 vectors, at least 200 vectors, at least 300 vectors, at least 500 vectors, at least 1.000 vectors, at least 5.000 vectors, at least $10^4$ vectors, at least $10^5$ vectors, at least $10^6$ vectors, at least $10^7$ vectors, at least $10^8$ vectors, at least $10^9$ vectors, at least $10^{10}$ vectors or at least $10^{11}$ vectors.

The present invention also relates to a method of preparing antigen-presenting cells, comprising transfecting or transforming cells with a peptide library of the invention.

Again, all definitions as well as the preferred embodiments provided herein above with regard to the methods of the invention and the peptide library apply mutatis mutandis also to this method of preparing an antigen-presenting cell.

Methods of transfecting or transforming cells are well known in the art and include, without being limiting, electroporation (using for example Multiporator (Eppendorf), Genepulser (BioRad)), viral transfer (e.g. using adenoviral, retroviral or lentiviral vectors), calcium-mediated transfection such as e.g. calcium phosphate precipitation, cationic lipids, PEI (Polysciences Inc. Warrington, Eppelheim), liposomes such as for example "Fugene" (Roche) or "Lipofectamine" (Invitrogen) or phage vectors. Such methods have been described in the art as well as in the examples below.

This method of preparing antigen-presenting cells thus provides a library of such antigen-presenting cells. Such a library may be employed for example in the methods of the present invention.

The present invention further relates to antigen-presenting cells obtainable by this method of the invention.

Furthermore, the present invention also relates to a primer or a set of primers selected from the group consisting of SEQ ID NOs: 1 to 9 and/or SEQ ID NOs: 39 to 47 and/or SEQ ID NOs: 11 and 14.

In accordance with the present invention, a number of primers have been identified that are suitable for the amplification and identification of nucleic acid molecules encoding T cell receptor β chains from individual cells or cell clones. As described above in detail, these primers have been optimised to minimize potential interactions with each other or with primers for the α chains during PCR reaction.

The term "set", as defined herein above, relates to a combination of primers. The set of primers of the present invention requires that more than one molecular species of primer is present. Thus, at least two different primers, such as at least three, at least four, at least five, at least six, at least seven, at least eight, at least nine, at least ten, at least 11, at least 12, at least 13, at least 14, at least 15, at least 16, at least 17, at least 18, at least 19 or at least 20 different primers selected from the primers represented by SEQ ID NOs: 1 to 9 and/or SEQ ID NOs: 39 to 47 and/or SEQ ID NOs: 11 and 14 are comprised in the set of primers.

The present invention further relates to a kit comprising the peptide library of the invention and/or the primer or set of primers of the invention and/or an/the antigen-presenting cell(s) of the invention.

The various components of the kit may be packaged in one or more containers such as one or more vials. The containers or vials may, in addition to the components, comprise preservatives or buffers for storage.

Preferably, the kit of the invention comprises the peptide library of the invention and the primer or set of primers of the invention.

Unless otherwise defined, all technical and scientific terms used herein have the same meaning as commonly understood by one of ordinary skill in the art to which this invention belongs. In case of conflict, the patent specification, including definitions, will prevail.

The figures show:

FIG. 1: Schematic overview over the transfectants used.

$58\alpha^-\beta^-$ T hybridoma cells were successively transfected with the TCR α- and β-chains of TCR JM22 in plasmids pRSVneo and pRSVhygro, respectively (termed 58-JM22 cells), the human CD8α- and β-chains, which were connected by an IRES-2 sequence, in a retrovirus generated by plasmid pLPC-CD8αIRESβ (termed 58-JM22-CD8 cells), and the packaging line GP+E and sGFP under the control of NFAT in pcDNA6 (termed 58-JM22-CD8-sGFP cells).

As antigen-presenting cells (APC), COS-7 cells were used that were transiently co-transfected with plasmid pRSV-A2, which codes for HLA-A*0201 in plasmid pRSV, and pcDNArc-library, which codes for either the control peptide flu(58-66) (pcDNArc-flu(58-66)), or for a combinatorial random peptide library where the HLA-A2 anchor positions 2, 6, and 9 are fixed (pcDNArc-A2-269).

Figure 2:
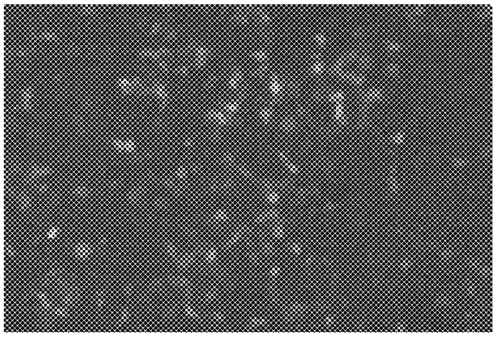
Figure 2:
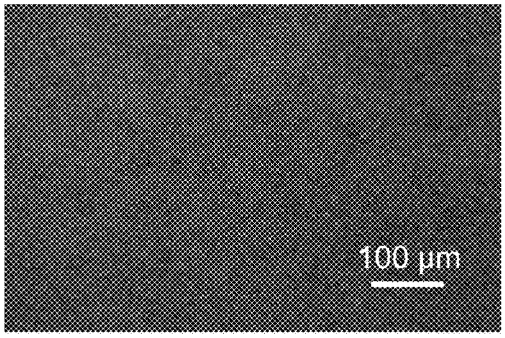
Figure 2:
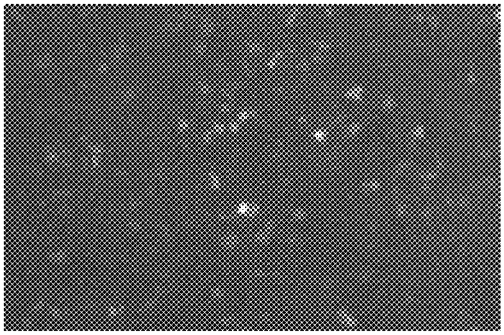
Figure 2:
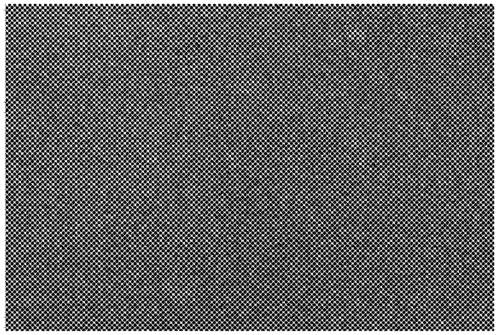
Figure 2:
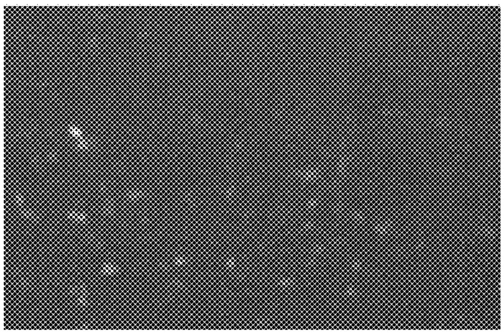
Figure 2:
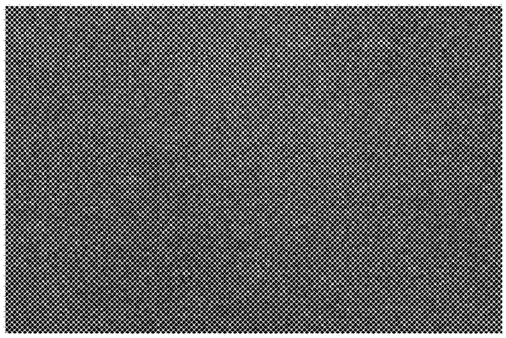
Figure 2:
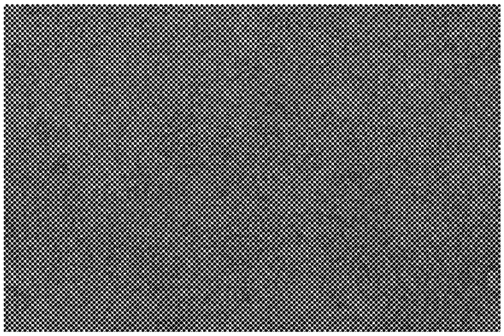
Figure 2:
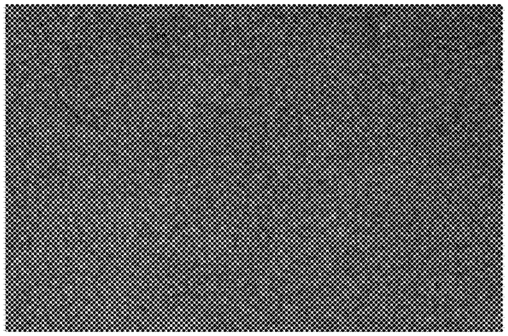

FIG. 2: Fluorescence microscopy of co-cultures of 58-JM22-CD8-sGFP cells with COS-7 cells that were transfected with HLA-A*0201.

Figure 3:
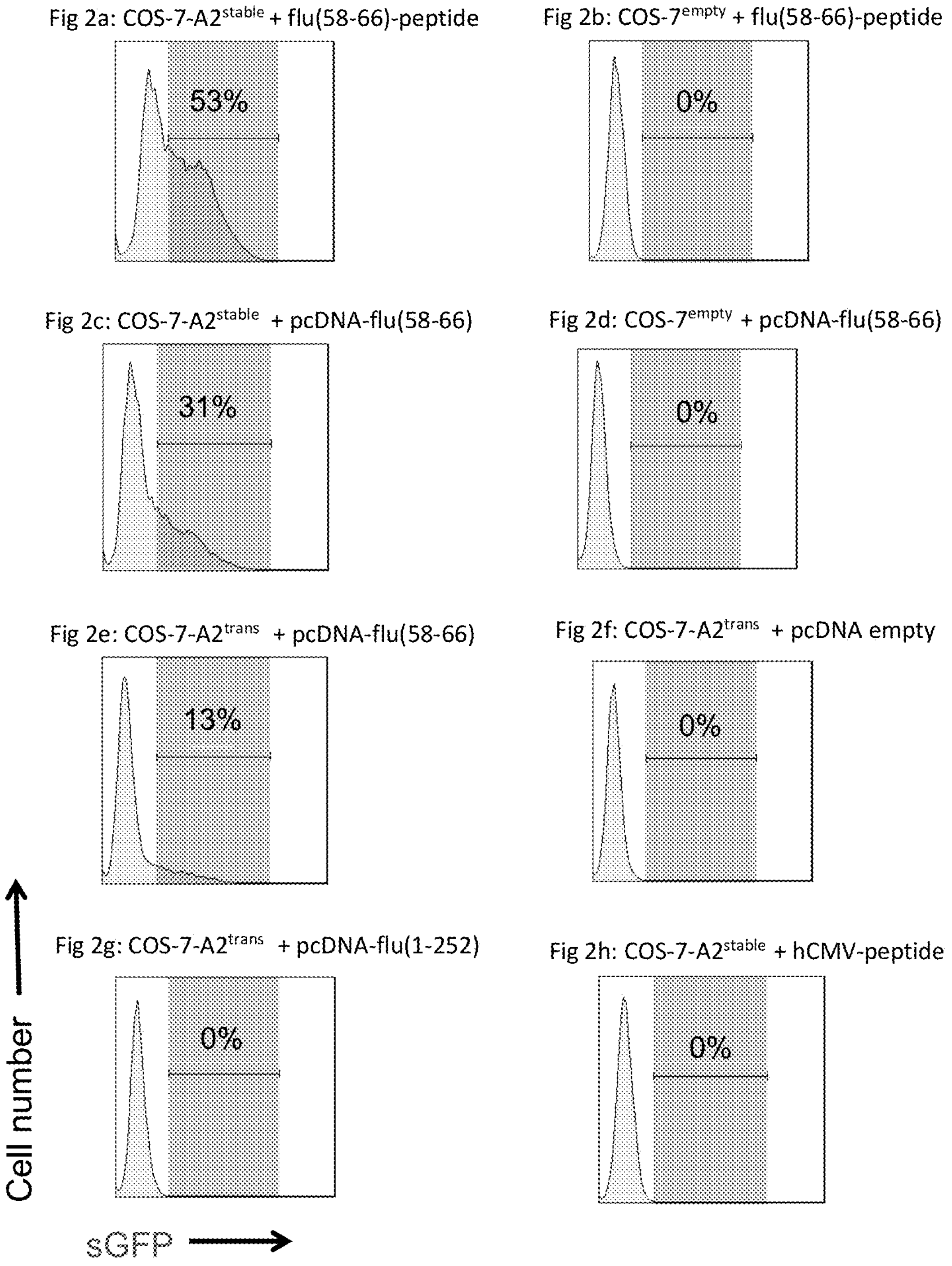

58-JM22-CD8-sGFP cells show green fluorescence upon activation. COS-7 cells were either used as untransfected cells (COS-7empty) or were transfected with HLA-A*0201, either stably (COS-7-A2stable) or transiently (COS-7-A2trans). The peptide flu(58-66) was added either as chemically synthesized peptide (flu(58-66)-peptide), or was transfected as a plasmid encoding the peptide (pcDNArc-flu(58-66)). The synthetic peptide hCMV (184-192), which binds to HLA-A*0201, but is not recognized by TCR JM22, and the empty plasmid pcDNA-empty served as negative controls. In addition, also the full length influenza matrix protein (pcDNA-flu(1-252)) was transfected. The following transfectants are shown: a: COS-7-A2stable+flu(58-66)-peptide; b: COS-7empty+flu(58-66)-peptide; c: COS-7-A2stable+pcDNA-flu(58-66); d: COS-7empty+pcDNA-flu(58-66); e: COS-7-A2trans+pcDNA-flu(58-66); f: COS-7-A2trans+pcDNA-empty; g: COS-7-A2trans+pcDNA-flu(1-252); h: COS-7-A2stable+hCMV-peptide FIG. 3: FACS scans of 58-JM22-CD8-sGFP cells after co-culture with COS-7 cells transfected with HLA and peptide. The same combinations as in FIG. 2 are shown.

Figure 4:
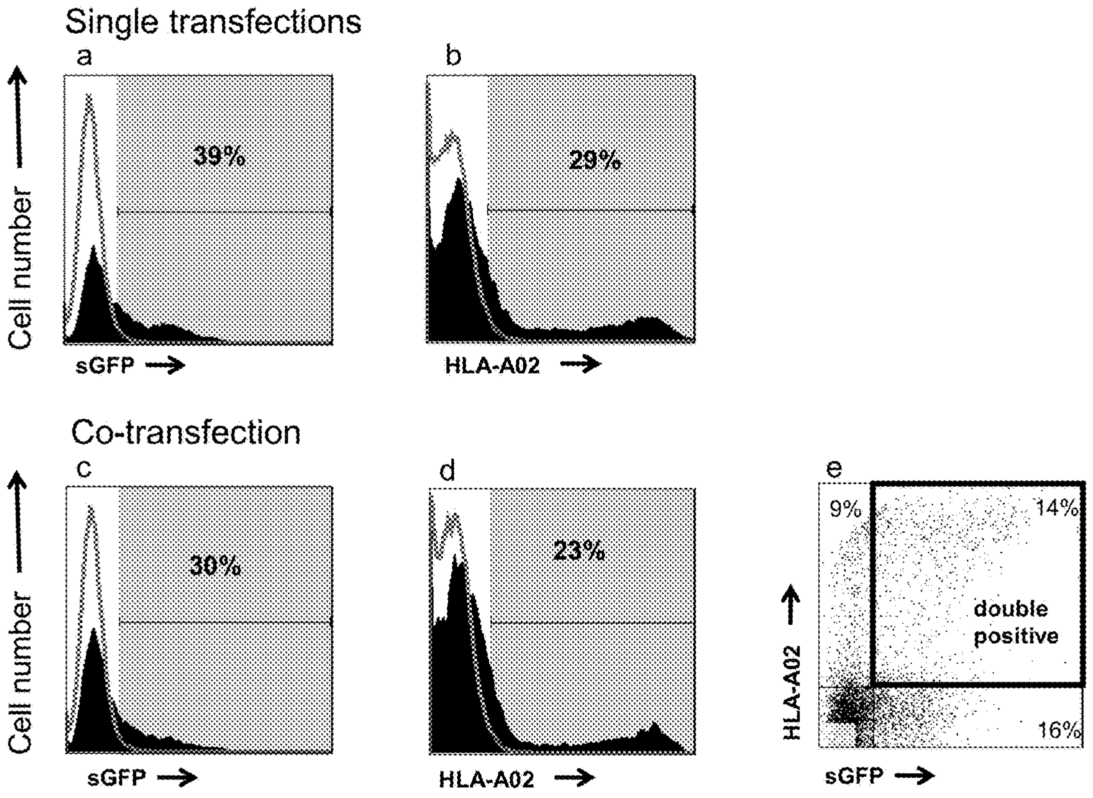

FIG. 4: Transfection of COS-7 cells with pcDNA-sGFP and pRSV-HLA-A2. The transfection yields were measured by the intrinsic sGFP fluorescence and by staining of HLA-A2 with the antibody BB7.2 (Proimmune) (black lines, black areas). All transfections were transient. In the case of sGFP analysis, cells that were not transfected served as negative controls. In the case of HLA-A2 analysis, the isotype control antibody BD-555743 was used. (controls: grey lines, empty areas)

a: single transfection with pcDNA-sGFP; b: single transfection with pRSV-HLA-A2; c: co-transfection with pcDNA-sGFP and pRSV-HLA-A2; sGFP analysis; d: co-transfection with pcDNA-sGFP and pRSV-HLA-A2; HLA-A2 analysis; e: co-transfection with pcDNA-sGFP and pRSV-HLA-A2; analysis of double positive cells FIG. 5: Fluorescence microscopy of co-cultures of 58-JM22-CD8-sGFP cells with COS-7 cells that were co-transfected with HLA-A*0201 and a library encoded by plasmid pcDNArc-A2-269. A positive 58-JM22-CD8-sGFP cell shows green fluorescence upon activation. The frequency of positive cells is about 3 per $10^6$ non-activated cells. The positive cell is indicated by an arrow.

a: Transmitted light. Cos-7 cells (irregular shape) and TCR transfected T hybridoma cells (round shape) are shown; b: sGFP fluorescence (472 nm-520 nm) indicates activated TCR transfected T hybridoma cells; c: PE-channel (545 nm-605 nm), no fluorescence is detected. This provides evidence that the detected sGFP fluorescence is not due to autofluorescence.

FIG. 6: Schematic outline of the protocol that leads to the identification of antigen-mimotopes. Initially an activated, green fluorescent TCR-transfectant is picked together with the subjacent antigen presenting cell that carries the activating plasmid. The inserts of the plasmids are cloned, and transfected into bacteria. To count the numbers of bacterial clones, a fraction of the bacterial clones is plated onto agar plates. Then 30 or more sub-pools of bacteria are created that contain 500 independent bacterial clones. They are transfected into COS-7 cells and tested again. From a positive sub-pool, further sub-pools are generated, which contain less clones per sub-pool. Finally, single bacterial clones are analyzed. Positive clones are sequenced and reveal the antigenic mimotope.

FIG. 7: Amino acid sequences of the parent peptide flu(58-66) and the mimotopes #1 to #4 that were discovered using the combinatorial random peptide library pcDNArc-A2-269. Mimotope #2 was found twice. In this library, the amino acids that code for HLA-A2 anchors at positions 2, 6, and 9 were fixed (highlighted grey). The amino acids at positions 4, 5 and 8, which are known to contact the TCR JM22 (Stewart-Jones et al. 2003), are boxed with dashed lines. The amino acids in the mimic peptides that were found to deviate from the parent peptide are circled.

FIG. 8: Amplification of Vα-/β-chains by the degenerative V Primers. The capacity of the Vα- and Vβ-primer sets to amplify the full TCR Vβ- and Vα-gene repertoire in a single reaction when combined with each other was tested by multiplex RT-PCR with mRNA from peripheral blood T cells. RNA of 500 cells was transcribed and amplified by one step RT-PCR with the same protocol as for single cell PCR involving the set of 9 Vβ and 24 Vα primers. Subsequently, the PCR product was amplified with the individual Vβ or Vα primers in individual PCR reactions. (A) Using the same 9 Vβ primers (Vp1-9) and nested Cβ primer, 0.5 ul aliquots of the multiplex PCR products were amplified by 35 cycles PCR (94° C. 30", 53° C. 30", 68° C. 30") with final extension of 15' at 68° C. All Vp1-9 primers (lanes 1-9) produced PCR signals of the expected size. (B) In parallel, the TCR Vα-repertoire was amplified from the multiplex-PCR product using the 24 different Vα-primers in individual reactions. Vα semi-nested amplification was performed the same way as for Vβ amplification. All Vα primers (upper and lower lanes 1-12) produced PCR signals of the expected size. (C) 2nd semi-nested PCR was performed from the first multiplex PCR reaction using FAM-labelled Cβ in primer and primers for the individual Vβ gene families. PCR products were loaded on POP 6 gel and analysed on a genetic sequencer. All Vβ families show polyclonal distributions and document that the multiplex Vβ primer set can amplify every functional Vβfamily.

FIG. 9: Three-step TCR Vβ-chain amplification from single T cells. After the 1st pre-amplification a 2nd run-off PCR step is performed to introduce a universal primer site. A 3rd semi-nested PCR then amplifies the respective TCR Vβ-gene rearrangement using the universal primer and the Cβ(2) nested primer.

Figure 10:
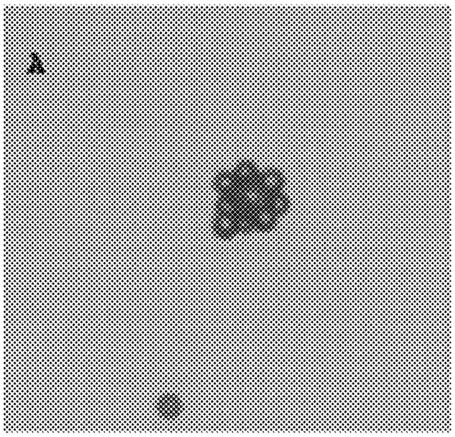

FIG. 10: Isolation of single T cells. A. For single cell TCR-analysis T cells were labelled with monoclonal antibody-coated magnetic beads, aspirated in invert microscopy and transferred into a PCR vial for RT-PCR.

The examples illustrate the invention:

EXAMPLE 1

Materials and Methods

Plasmids and Transfections

Table 6 lists primer sequences employed for plasmid constructions. All constructs were confirmed by full length sequencing of the inserts.

TABLE 6

Linkers and PCR primers.

| Plasmid recovery | NAME | SEQUENCE | SEQ ID NO: |
|---|---|---|---|
| Outer PCR | pcDNA-for-1 | 5'-CAC TGC TTA CTG GCT TAT CG | 84 |
| | pcDNA-rev-1 | 5'-ACT AGA AGG CAC AGT CGA GG | 85 |
| inner PCR dTOPO | pcDNA-for-2-TOPO(Mimo 11) | 5'-CACCCGA CTC ACT ATA GGG AGA CC | 86 |
| | pcDNA-2nd-for-TOPO(Mimo 2, 3) | 5'-CACCTCCGGCGCGCCACCATG | 87 |
| | pcDNA-rev-2(Mimo 1) | 5'-CTG ATC AGC GGG TTT AAA CTC | 88 |
| | pcDNA-rev-3 (Mimo 2, 3) | 5'-TGG TGA TGG TGA TGA TGA CC | 89 |
| inner PCR RE digest | pcDNA-2nd-for | 5'-TCC GGC GCG CCA CCA TG | 90 |
| | pcDNA-2nd-rev-10 | 5'-CTA GAC TCG AGC GGC CGC | 91 |
| JM22 | JM22-Valpha-for | 5'-TGT GTC GAC ATG GTC CTG AAA TTC TCC GTG | 92 |
| | JM22-VJalpha-rev | 5'-TTG GGA TCC CGC TCC TGC ACA GAG GTA GTG GC | 93 |
| | JM22-Jalpha-for | 5'-GAG GGA TCC CAA GGA AAT CTC ATC TTT GGA AAA | 94 |
| | Calpha Pvull-rev | 5'-AGC ACT GTT GCT CTT GAA GTC | 95 |
| | JM22-Vbeta-Kpn-for | 5'-CAT GTA CTG GTA CCG ACA GG | 96 |
| | JM22-VJbeta-Sca-rev | 5'-CCG AAG TAC TGC TCG TAG GAG CTC CTC GAA CTA CTG GCA CA GAGA TAG AAA G | 97 |
| CD8 | hCD8a-Not-for | 5'-ATA AGA ATG CGG CCG CAT GGC CTT ACC AGT GAC CGC | 98 |
| | hCD8a-EcoRI-rev | 5'-GGA ATT CTT AGA CGT ATC ACG CCG AAA G | 99 |
| | hCD8b-Mlu-Mut | 5'-TCG ACG CGT ATG CGA CCG CGG CTG TGG | 100 |
| | hCD8b-Xho-rev | 5'-CCG CTC GAG TTA TTT GTA AAA TTG TTT CAT GAA AC | 101 |

TABLE 6-continued

Linkers and PCR primers.

| Plasmid recovery | NAME | SEQUENCE | SEQ ID NO: |
|---|---|---|---|
| NFAT-sGFP | sGFP-Eco-for | 5'-TC GAA TTC GCC ACC ATG GTG AGC | 102 |
| | sGFP-Xho-rev | 5'-GA CTC GAG AGC TTA GTG ATG GTG ATG | 103 |
| HLA-A*0201 | HLA-A0101-lead | 5'-CTC GTC GAC ATG GCC GTC ATG GCG CCC | 104 |
| | HLA-A0101-end | 5'-TAC GGA TCC TCA CAC TTT ACA AGC TGT GAG | 105 |
| pcDNArc | pcDNArc-MCS-for | 5'-GAT CCG GCG CGC CCC TGC AGG GC | 106 |
| | pcDNArc-MCS-rev | 5'-GGCCGCCCTGCAGGGGCGCGCCG | 107 |
| flu(58-66) | N27-flu-Asc-for | 5'-CGCGCC ACC **ATG GGC ATT CTT GGG TTT GTG TTC ACT CTG TGA** GC | 108 |
| | N27-flu-Not-rev | 5'-GGCCGC TCA CAG AGT GAA CAC AAA CCC AAG AAT GCC CAT GGTGG | 109 |
| random peptide libraries | N27-all-lib-Asc-for | 5'-CAGG GAA GGCGCGCC ACC **ATG NNK NNK NNK NNK NNK NNK NNK NNK NNK TGA** GCGG CCGC TAA ACT AT | 110 |
| | N27-A2-269-lib-Asc-for | 5'-CAGG GAA GGCGCGCC ACC **ATG NNK ATC NNK NNK NNK GTG NNK NNK CTA TGA** GCGG CCGC TAA ACT AT | 111 |
| | N27-Not-rev | 5'-TAG TTT AGC GGC CGC TCA | 112 |

The first column gives the purpose the primers or linkers were used for. The second column lists the names of the primers or linkers. In the third column the sequences are given. The regions coding for peptide flu(58-66) or for the random peptide libraries are highlighted in bold print. The restriction sites or linker-overhangs are boxed. The letters N and K are defined: N = A or T or G or C.; K = G or T. The corresponding SEQ ID Numbers are presented in the fourth column.

Construction of Expression Plasmids pRSVhygro-JM22α and pRSVneo-JM22β and Generation of TCR-transfected Hybridoma Cells (58-JM22 Cells)

RNA was prepared from peripheral blood of a volunteer by the TRIzol-RS reagent (Gibco/Invitrogen), and DNA prepared using Superscript III reverse transcriptase (Gibco/Invitrogen) and oligo(dT) primer. The V-regions of the α- and β-chains of TCR JM22 (Lehner et al., 1995) were amplified by PCR. The N(D)N regions were inserted by mutagenesis. We used the plasmids pRSVneo and pRSVhygro that contained the C-regions as cloning cassette (Seitz 2006). Specifically, we produced two α-chain PCR fragments: The first reached from the leader-region of Vα10 to the J region (primers: JM22-Valpha-for and JM22-VJalpha-rev), and the second reached from the J-region to the PvuII site in the C-region (primers: JM22-Jalpha-for and Calpha-PvuII-rev). The nucleotides coding for Gly and Ser in JM22-VJalpha-rev and JM22-Jalpha-for were substituted by silent mutations to introduce a BamHI site. The PCR product was digested by BamHI, ligated, and used as template for a second PCR with JM22-Valpha-for and Calpha PvuII-rev. The SalI and PvuII digested product was inserted into pRSVhygro that already contained the TCR C-region as a cloning cassette.

For cloning the JM2213-chain we used a Vβ17-Jβ2.7 positive clone as template which we had previously cloned into pRSVneo. We amplified the region between the KpnI site of Vβ17 and the ScaI site in J132.7 with the primers JM22-Vbeta-Kpn-for and JM22-VJbeta-Sca-rev and cloned the PCR product into the above plasmid.

Both plasmids were transfected into the T hybridoma cell line $58\alpha^-\beta^-$, (Blank et al., 1993), selected by G418 and hygromycinB (Sigma), and individual clones were isolated as described for other TCR-chains in Seitz et al. 2006. The resulting TCR transfected cell line is designated 58-JM22.

Construction Plasmid pLPC-hCD8α-IRES2-hCD8β and Generation of 58-JM22-CD8 Cells

The α- and β-chains of human CD8 molecules were amplified from cDNA using the primers: hCD8a-Not-for, hCD8a-EcoRI-rev, hCD8b-MluI for, and hCD8b-Xho-rev. The α-chain was inserted into the NotI and EcoRI sites and the β-chain into the MluI and XhoI sites of pQCXIX (Clontech). The pIRES sequence in pQCXIX (Clontech) was replaced by pIRES2 which was excised from pIRES2-DsRed2 (BD Biosciences). The fragment comprising hCD8α-IRES2-hCD8β was excised by NotI and EcoRV and inserted into the NotI and the blunted ClaI sites of pLPCX (Clontech). The resulting plasmid pLPC-hCD8α-IRES2-hCD8β was transfected into GP+E86 packaging cells (ATCC). 58-JM22 hybridoma cells, which already are transfected with the CD3 ξ-chain under histidinol selection (Blank et al, 1993), were co-cultured with the retrovirus-expressing GP+E86-CD8αβ cells for two days. Transformed cells were selected by 1.0 μg/ml puromycin (Sigma). CD8αβ expression was analyzed by FACS using the anti-CD8α- and anti-CD8β-antibodies antibodies B9.11 and 2ST8-5H7 (Beckman Coulter). The resulting TCR and CD8 transfected cell line is designated 58-JM22-CD8.

Construction of Plasmid pcDNA6-NFAT-sGFP and Generation of 58-JM22-CD8-sGFP Cells The NFAT-response-element-hrGFP-SV40splice/pA sequence was isolated from pNFAT-hrGFP (Stratagene). We first cut with AccI, created blunt ends, and then digested with AatII. The fragment was ligated into pcDNA™6/V5-His C which was digested with PmeI and AatII yielding the plasmid pcDNA-NFAT-hrGFP. sGFP(S65T) (Heim et al., 1995) was amplified using the primers sGFP-Eco-for and sGFP-Xho-rev and ligated into the EcoRI and XhoI sites of pcDNA-NFAT-hrGFP which yielded plasmid pcDNA-NFAT-sGFP. 58-JM22-CD8 cells were transfected and selected by 3 µg/ml blasticidin (Invitrogen) and individual clones were picked and analyzed for GFP expression after stimulation with the anti-CD3 antibody 145-2C11 (BD) and HLA-A2-flu(58-66). The resulting TCR, CD8, and NFAT-sGFP transfected cell line is designated 58-JM22-CD8-sGFP.

Construction of Plasmind pRSV-A2 and pHSE3'-A2

The cDNA of the HLA-A2 heavy chain was amplified by PCR using the primers 5'EX1-A-6 and 3'A-ex8-1 (M. P. Bettinotti et al. (2003) J. Immunol. Meth. 279:143-148) and cDNA from patient PM16488 (Seitz 2006). After re-amplification with primers extended for SalI and BamHI restriction sites (HLA-A0101-lead and HLA-A0101-end), the PCR products were inserted into the SalI and BamHI sites of pRSVneo and pHSE3' (Pircher et al., 1989). These plasmids were used to transfect COS-7 cells as described below.

Construction of Plasmid pcDNA6-flu(1-252)

The full length sequence of matrix protein flu(1-252) was synthesized with the Kozak sequence CCACC directly before the start codon, a stop signal and NheI and XbaI overhangs (GeneArt). The fragment was inserted into the NheI and XbaI sites of pcDNA™6/V5-His A (Invitrogen).

Construction of Plasmid pcDNA6-flu(58-66)

A nucleotide sequence coding for flu(58-66) was inserted into the HindIII and XhoI sites of pcDNA™3.1zeo(+) (Invitrogen) by a double stranded synthetic linker that contained sticky overhangs, the Kozak sequence CCACC directly before the start codon, and a Stop-signal. The forward strand flu(58-66)-COS-for and the reverse strand flu(58-66)-COS-rev were hybridized by incubation at 95° C. for 5 min, cooled slowly and ligated into the HindIII and XhoI sites of pcDNA™3.1zeo(+). From this plasmid the NheI-XbaI Fragment was ligated into the NheI and XbaI sites of pcDNA™6/V5-His A.

Construction of Plasmid pcDNA6rc-spacer

The plasmid pcDNArc-spacer was designed as recipient plasmid for complex libraries. We first introduced the restriction sites for rare cutting enzymes AscI and NotI into the multiple cloning site of pcDNA™ 6/V5-His A (Invitrogen). To this end, we digested pcDNA™/V5-His A with BamHI and NotI and ligated the linker oligonucleotides pcDNArc-MCS-for and pcDNArc-MCS-rev into the BamHI and NotI sites of pcDNA™6/V5-His A, yielding the plasmid pcDNArc ("rc" means "rare cutter").

Because the two restriction sites AscI and NotI are quite close to each other, we then inserted an irrelevant DNA fragment to facilitate later AscI and NotI digestions. Hence, we excised a 2514 bp fragment from plasmid pLNCX2 (Clontech) by AscI and NotI digestion and inserted it into the AscI and NotI digested plasmid pcDNArc. The resulting plasmid "pcDNArc-spacer" was then used as recipient plasmid for libraries and flu(58-66).

Construction of Plasmid pcDNA6rc-flu(58-66)

The nucleotide sequence coding for flu(58-66) was inserted into the AscI and NotI sites of pcDNA6rc. We generated a double stranded synthetic linker with sticky AscI and NotI overhangs, the Kozak sequence CCACC directly before the start codon, and a Stop-signal. The forward strand N27-flu-Asc-for and the reverse strand N27-flu-Not-rev were hybridized by incubation at 95° C. for 5 min, cooled slowly and ligated into digested pcDNA6rc-spacer.

pcDNA6rc-flu(58-66) behaved absolutely identical in all experiments as pcDNA6-flu(58-66).

Construction of Plasmids pcDNArc-N27-all and pcDNArc-N27-A2-269

To generate random peptide libraries, we used the following single strand oligonucleotides: N27-all-lib-Asc-for for a completely randomized 9 amino acid library; and N27-A2-269-lib-Asc-for: for a 9 amino acid library with 3 fixed anchor positions of flu(58-66): isoleucin at position 2, valine at position 6, and leucin at position 9. All oligonucleotides contained the restriction sites AscI and NotI, the Kozak sequence CCACC directly before the start codon, and a stop sequence.

Double strands were generated from these plasmids by annealing the short plasmid N27-Not-rev and a subsequent fill-in reaction. We annealed the library coding plasmids and N27-Not-rev at 5 µM each in 10 mM Tris-HCl, 1.5 mM MgCl2, 50 mM KCl, pH=8.2 by incubation for 5 min at 100° C. and cooling slowly within one hour to room temperature. Then an equal volume of the above buffer was added, containing dNTPs and Taq-polymerase (both Roche) adjusted to final concentrations of 200 µM, and 5 U/100 µl, respectively, and the mixture was gradually heated for 5 min to 60° C., then for 4 min to 63° C., then for 4 min to 65° C., and finally for 1 hour to 68° C. The double strands were then digested with AscI and NotI and inserted into the AscI and NotI sites of pcDNArc-spacer.

Construction of Plasmid pcDNA-sGFP

To measure the efficiency of a transfection method, we cloned sGFP without NFAT response element. We digested pcDNA-NFAT-sGFP with EcoRI and XhoI, isolated the sGFP sequence and ligated it into pcDNA™6/V5-His A (Invitrogen).

Synthetic Peptides

The peptides representing influenza matrix protein amino acids 58 to 66 (flu(58-66): GILGFVFTL) and human cytomegalovirus fragment pp 65 amino acids 184 to 192 (hCMV-pp 65(184-192): NLVPMVATV) were synthesized by Fmoc chemistry and purified by C8 reverse phase HPLC. Their correct sequences were verified by mass spectrometry.

Antigen Detection Assay

Cell Transfections

Transfection and selection of $58\alpha^-\oplus^-$ with JM-22 α- and β-chains and with CD8α-IRES2-β were performed as described for other TCR chains (Seitz et al., 2006). These cells were then transfected with plasmid pcDNA-NFAT-sGFP and stable transfectants were selected by 3 µg/ml Blasticidine.

Two different methods were used to transiently transfect COS-7 cells with the plasmids containing the library: "Fugene"-mediated transfection and electroporation. The "Fugene" method is very effective, and delivers on average 200 individual plasmids into a single COS-7 cell. This method is preferred for transfecting pools of plasmids or single plasmids from individual bacterial clones, i.e. at the late stage of the antigen search. Electroporation, on the other hand, delivers about 3 to 5 plasmids into a single COS-7 cell. Therefore the heterogeneity of library plasmids is lower in a single cell when electroporation is used. This method is therefore preferred at the early stages of antigen search, when libraries of high complexities are used. It is of note that each COS-7 cell amplifies the transfected plasmids to about 5.000 copies in total within 2 to 3 days. Consequently, after electroporation, each individual plasmid-species is amplified to a much greater extent, e.g. electroporation of e.g. 4 different transfected plasmids yields 4 different plasmid-species with 1.250 copies each while with the Fugene method, for example 200 different transfected plasmids yield 200 different plasmid-species with only 25 copies each.

Electroporation Protocol: To transiently transfect COS-7 cells by electroporation, $4 \cdot 10^6$ cells were washed twice in RPMI and resuspended in 0.8 ml hypo-osmolar buffer (Eppendorf). Then 16 μg of DNA (in 10 mM Tris-HCl, pH 8.5) were added. For co-transfection plasmids pRSV-A2 and pcDNA-flu(58-66) or pcDNA-flu(1-152) or pcDNA-A2-269 or pcDNArc were used at equal molar amounts. The electric pulse was applied at room temperature in 0.4 cm electroporation cuevette (Eppendorf) with 1200 V and for 40 ms using a "Multiporator" transfection apparatus (Eppendorf). Immediately after the electric pulse the cells were resuspended in pre-warmed complete media. In some experiments, the cells were washed twice with 20 mM Na-phosphate buffer, pH=7.4, 150 mM NaCl, 10 mM $MgCl_2$. Then they were seeded on dishes ($0.5\text{-}1 \cdot 10^6$ cells per 3.5 cm dish) and incubated under normal cell culture conditions.

Fugene Protocol: Transient transfection of COS-7 cells with FugeneHD transfection reagent (Roche) was performed at a ratio of 2 μg DNA: 7 μl Fugene. Plasmids pRSV-A2 and pcDNA-flu(58-66) or pcDNA-A2-269 were used at equal molar amounts. To remove residual transfection complexes, COS-7 cells were washed 4 times with PBS 24 h after transfection, incubated for one hour with 50 μg/ml herring sperm DNA to replace the plasmids in the transfection complexes, and then and for 2 hours with 0.2 mg/ml DNase and 10 mM $MgCl_2$ to digest remaining DNA.

The transient transfection efficiency of COS-7 cells was determined by FACS analysis using pcDNA6 coding for-sGFP or pRSV-A2. Positive cells were analysed by intrinsic sGFP fluorescence or by staining with the anti-HLA-A2 antibody BB7.2 (Proimmune). Maximum expression was observed between 48 and 72 hours post transfection.

Detection of Cells Presenting an Antigen Recognized by T Cells

To detect COS-7 cells that contained a library-plasmid coding for a peptide that is recognized by the TCR-transfected hybridoma cells, library-transfected COS-7 cells were plated on tissue culture plates at a density of about 40.000 cells/cm$^2$. After incubation for 2 to 3 days at 37° C., the almost confluent cell layer was washed twice with RPMI medium and overlayed with 58-JM22-CD8-sGFP T-hybridoma cells, and incubated for additional an 12 to 18 hours. Then the plates were examined under an inverse fluorescence microscope (AxioVert200M, Zeiss, equipped with a CCD-Camera (CoolSNAP-HQ, Roper Scientific), a fluorescence lamp (HXP 120, Visitron), and the objectives: 5×, NA 0.15; ∞/0, Epiplan-NEOFLUAR; 10×, NA 0.45 Plan Apochromat; 20×, NA 0.4; ∞/0-1.5 Achroplan, Korr Ph2). A Cy3-Filter (excitation/emission: 545(25)/605(70) nm, Zeiss) was used to check for auto fluorescence and a GFP-Filter (excitation/emmision at 472(30)/520(35) nm, Semrock, BrightLine) to detect sGFP expression. Alternatively to manual search, an automated scan system based on a motorized xy-stage (BioPresision2, Visitron, Puchheim, Germany) and automated picture acquisition and analysis (MetaMorph-Software, V7.7) was used. COS-7 cells in contact with activated green 58-JM22-CD8-sGFP hybridoma cells were then picked with a thin capillary (Eppendorf, customTips Type I, inner diameter 15 μm) and a micro manipulator (Mini 25, Luigs & Neumann). Picked cells were flushed into 7 μl of 25% ammonia solution and stored for up to 4 hours on ice to preserve plasmids and to inhibit DNases. Before the PCR-reaction, the tubes were opened for 30 min at room temperature to facilitate evaporation of ammonia.

Amplification of Plasmids Encoding Antigens

PCR amplification of the pcDNA inserts was performed as two rounds of nested PCR. A first PCR reaction was performed in 50 to 100 μl with 1 U Taq polymerase (Roche) (0.2 mM dNTP, 0.5 μM primer). In some experiments a single PCR using inner or outer primers was sufficient. Subsequently, an equivalent to 0.01 μl of the first reaction product were used as template in a nested PCR reaction with iProof polymerase (Biorad) and inner primers. The PCR product was purified with MinElute PCR purification kit (Qiagen) and cloned into plasmid pcDNA3.1D/V5-His-TOPO® (Invitrogen). The ligation product was transfected into DH10B ElectroMax (Invitrogen) bacteria by electroporation.

Additional Screening and Identification of Mimotopes

The enriched mimotopes were subjected to further rounds of antigen screening where pools of independent bacterial clones were used (FIG. 6). A small fraction of the transfected bacteria was grown on agar plates to determine the number of bacteria contained. The major fraction was grown in bulk culture. From this >30 pools of about 500 independent bacterial clones each were grown in suspension culture, plasmids were prepared, and then transfected into fresh COS-7 cells. These were tested again for activation of 58-JM22-CD8-sGFP cells. From positive pools again >30 subpools with 100 bacterial clones each were created, which were tested as above. Then the procedure was repeated with >30 sub-pools of 20 independent bacterial clones, which in addition were grown on agar plates. From these individual bacterial colonies were picked and tested. Plasmids that were positive in this last round of analysis were sequenced.

Amplification of TCR α- and β-chain cDNA from the Single Cell by One Step RT-PCR Protocol Steps 1.1, 1.2. (RT-PCR) mRNA of single cell was transcribed into cDNA by RT reaction for 35 min at 50° C. using a one step RT-PCR kit (QIAGEN) and gene specific Cα- and β-primers (0.6 uM each) (Cprimer=Cαout Primer+Cβout primer, Table 2).

Protocol Step 1.3. ($1^{st}$ Multiplex PCR) Pooled primers for the simultaneous amplification of Vα- and β-chain (Vprimer) were added to the reaction solution. The pool contains 24 Vα-specific and 9 Vβ-specific primers (Vp1-Vp9) (0.075 uM each) (Table 1 and 3), which cover all functional α and β TCR variable region genes. After 15 min at 95° C. for the activation of hot start polymerase, 10 PCR cycles were performed at 94° C. for 30 sec, at 60° C. for 90 sec and at 68° C. for 60 sec. Subsequently 30 PCR cycles were performed at 94° C. for 30 sec, at 53° C. for 90 sec and at 68° C. for 60 sec, followed by a 15 min final extension step at 68° C.

Protocol Step 2.1. (Run Off-PCR) For the amplification of the Vβ-chain a 1 ul aliquot of the pre-amplification product was subjected to 1 cycle of run-off PCR at 94° C. for 5 min, 53° C. for 150 sec and 68° C. for 15 min using primers based on the Vp primers supplemented with a universal primer sequence at the 5' end (Vp+ primer). 10 ul reaction solution contains 1*PCR Buffer, 0.25 U DNA Polymerase (Roche), 0.2 mM dNTP and Primer Pool (0.1 uM each primer).

Protocol Step 2.2. ($2^{Nd}$ Seminested PCR) A "semi-nested" PCR was run using a Cβ specific nested primer (Cβ-in) and a universal primer (UP). PCR consists of a 2 min denaturation step at 94° C., 50 cycles at 94° C. (30 sec), 58° C. (60 sec), 68° C. (60 sec) and a 15 min final extension step at 68° C.

Protocol Step 3 (Vα Amplification). The second nested amplification of the Vα-chain was performed as described in a previous report with a little modification (Seitz et al.

(2006)). Briefly, 1 ul of the pre-amplification probe was added to a PCR solution containing a Cα-nested primer (Cα-in) and the Vα-nested primer pool (0.1 uM each primer). After denaturation (2 min at 94° C.), touch down PCR was run with each 4 cycles at 61° C., 58° C., and 56° C. annealing followed by 40 cycles at 53° C. annealing. Annealing and extension (68° C.) times were 1 min each, and denaturation time 30 sec, followed by a final extension at 68° C. for 15 min. TCR β- and α-chain were directly sequenced using Cβ-/Cα-nested primers and 0.5 ul of the nested PCR product.

EXAMPLE 2

Properties of the Readout System

The T hybridoma cell line $58\alpha^-\beta^-$ was stably transfected with the α- and β-chains of the TCR JM22, the human CD8 α- and β-chains, and a reporter construct where sGFP is controlled by NFAT (termed 58-JM22-CD8-sGFP cells) (FIG. 1). To test whether green fluorescence in these transfectants may be detected after antigen stimulation, COS-7 cells were used as APC that were stably transfected with HLA-A*0201 in plasmid pHSE3' (pHSE3'-A2) and the synthetic peptide flu(58-66) was added. The adherent COS-7 cells formed an almost confluent monolayer. 58-JM22-CD8-sGFP cells were added and sGFP fluorescence was observed after 16 hours under a fluorescence microscope (FIG. 2*a*) and by FACS (FIG. 3*a*). More than 50 percent of 58-JM22-CD8-sGFP cells were found to be activated as evident by their bright sGFP fluorescence. If empty COS-7 cells that have not been transfected with HLA-A2 were used (FIG. 2*b* and FIG. 3*b*), or if flu(58-66) was replaced by the irrelevant peptide hCMV(184-192) (FIG. 2*h* and FIG. 3*h*), not a single positive 58-JM22-CD8-sGFP cell among 250.000 cells was observed. These experiments show that 58-JM22-CD8-sGFP cells may serve as suitable readout cells to specifically detect HLA-peptide complexes.

To avoid the need for generating stable HLA-transfected COS cells for each HLA-allele under question, the protocol was modified so that all transfections into COS cells are transient. In a first step it was tested whether flu(58-66) needs to be added as a synthetic peptide, or whether it may be encoded in a plasmid that is transfected into COS cells that stably express HLA-A*0201. Hence, COS-7 cells that were stably transfected with pHSE3'-A2 were transiently super-transfected with the plasmid pcDNA that coded for expression of flu(58-66) (pcDNA-flu(58-66)) by electroporation (FIG. 2*c* and FIG. 3*c*; see Tab 6 for plasmid insert sequences). pcDNA carries the SV40 origin, which ensures intracellular plasmid-amplification in COS-7 cells (Gluzman, 1981). The yield of fluorescent 58-JM22-CD8-sGFP was 31 percent, which is only slightly lower as compared to the experiment where the synthetic peptide was added directly (FIG. 2*a* and FIG. 3*a*). Of note, this experiment shows directly that peptides encoded by pcDNA can be expressed in the cytosol of COS-7 cells and are efficiently transported into the lumen of the endoplasmic reticulum where they are loaded onto class-I MHC molecules.

Next, both pRSV-A2 and pcDNA-flu(58-66) were transiently co-transfected at a molar ratio of 1:1 into COS cells. 58-JM22-CD8-sGFP cells were added after 56 hours and their fluorescence was observed again 16 hours later (FIG. 2*e* and FIG. 3*e*). The yield of activated 58-JM22-CD8-sGFP was 13%, i.e., it is slightly lower than for stable transfectants (FIGS. 2*a* and 2*d*). It is in the same range as the transfection-rate of 14 percent in a model system, where pRSV-A2 and GFP in pcDNA were co-transfected, which may both be easily quantified by FACS (FIG. 4). sGFP expression in 58-JM22-CD8-sGFP cells was observed 8 hours after starting co-culture with library-transfected COS cells and was stable for more than 16 hours. During that time the 58-JM22-CD8-sGFP cells maintained tight contact with their antigen presenting COS-7 cell. In negative control experiments, where pRSV-A2 and pcDNA without insert (pcDNA-empty) were co-transfected (FIG. 2*f* and FIG. 3*f*) or where pcDNA-flu(58-66) was transfected without pRSV-A2 (FIG. 2*d* and FIG. 3*d*), no activation of 58-JM22-CD8-sGFP cells was observed. Strikingly, no positive cells were identified when pcDNA-flu(58-66) was replaced by pcDNA-flu(1-252), i.e. by a construct that codes for the full length influenza matrix protein sequence (FIG. 2*g* and FIG. 3*g*). This shows that the COS-7 cells were unable to correctly process the full-length flu(1-252) protein. It is of note that the present method circumvents all intracellular protease cleavage requirements for the antigens, because it takes advantage of testing with short peptides.

EXAMPLE 3

Screening of Randomized Peptide Libraries and Identification of Flu(58-66) Mimotopes To identify mimotopes of flu(58-66), random libraries were generated. These libraries consisted of a series of N-nucleotides that were flanked at the 5'-end by a Kozak sequence and a start-codon and at the 3'-end by a stop-codon (Tab 6). The libraries were inserted into the plasmid pcDNArc and co-transfected with pRSV-A2 into COS-7 cells. Since antigens presented by HLA-A*0201 were investigated, three fixed amino acids were introduced, which provide the three HLA-A2-binding anchors in positions 2, 6, and 9 (pcDNA-A2-269) (Rammensee et al., 1999). The HLA-A2*0201 anchor positions isoleucine in position 2, valine in position 6 and the main anchor leucine in position 9 of flu(58-66) were fixed. All other positions were randomized. The library was co-transfected together with pRSV-A2 into COS-7 cells and activation of a small number of 58-JM22-CD8-sGFP cells was observed (FIG. 5*b*). The direct contact of the fluorescent activated 58-JM22-CD8-sGFP cell with an subjacent COS-7 cell is visible (FIG. 5*a*). The frequency of activated 58-JM22-CD8-sGFP cells was found to be about 3 fluorescent cells per million COS-7 cells.

To recover the pcDNA plasmid that codes for the activating peptide mimotope, the activated 58-JM22-CD8-sGFP cells were picked together with the subjacent COS-7 cells with a thin capillary under a fluorescent microscope. Although COS-7 are adherent cells, they can be recovered from the bottom of the tissue culture plate. Under co-culture conditions of 58-JM22-CD8-sGFP cells with COS-7 cells co-transfected with HLA-A2 and pcDNA-A2-2,6,9, both the fluorescent 58-JM22-CD8-sGFP cell and the subjacent COS cell can be picked together. This can be observed under fluorescent or, better, under transmitted light.

From the picked cells, the mimotope coding sequences were amplified by PCR, cloned and co-transfected with pRSV-A2 into fresh COS-7 cells, or transfected into COS-7 cells that previously stably transfected with HLA-A2. Then they were tested again for 58-JM22-CD8-sGFP activation. Although in most cases it was possible to pick single COS-7 cells, many different inserts were initially recovered, presumably because a single COS cell typically contains more than one library-plasmid, and because plasmids in transfection complexes may still be present in the medium outside the cells and are aspirated together with the cells. Independent pools of bacterial clones were therefore analyzed until the population was homogenous and the inserts of the plasmids could be sequenced (FIG. 6). We identified four different mimotopes represented by four peptides (termed "mimo-1" to "mimo-4"; FIG. 7). mimo-2 was identified twice independently. The deduced amino acid sequences thus revealed differ from flu(58-66) in several amino acids in position one, three, and five. Amino acids in positions one and three are known not to interact strongly with both, HLA-A*0201 and JM22 (Stewart-Jones et al., 2003). The amino acid replacement in position five (mimo-2: tryptophan replaces phenylalanine) is conservative. However, it is of interest that this amino acid interacts with several loops in the TCR complementarity determining regions. Using the mimotop sequences for Blast searches under standard conditions, it was possible to unequivocally identify the parent flu(58-66) sequence.

EXAMPLE 4

Analysis αβ-T-cell Receptor Rearrangements in Single T Cells 4.1 Primer Design and PCR Strategy Molecular analysis of the paired αβ-TCR rearrangements of single T cells has to encompass the complete spectrum of ~70 TCR Vβ- and ~50 TCR Vβ-region genes. We focussed on the development of a PCR strategy, which can amplify all different Vβ-gene families of the TCR β-chain repertoire together with a set of 24 TCR Vα-primers recently described for the simultaneous amplification of the TCR Vα repertoire (Seitz, Schneider et al. 2006). The complexity of this approach results from potential interactions between the multitude of primers, which may interfere with specific amplification. Our efforts finally resulted in a PCR protocol, which starts with a multiplex RT-PCR capable of pre-amplifying all TCR Vα- and Vβ genes in a single reaction. Subsequently, the TCR Vα- and Vβ-PCR products are handled separately.

4.2 Preamplification of αβ TCR-rearrangements

To keep the number low, TCR Vβ-primers were designed utilizing sequence homologies of the various Vβ-gene families as identified by sequence alignments. One mismatch with the primary nucleotide sequence was allowed. Primer positions had to consider that direct sequencing could still identify the respective TCR Vβ-gene. To minimize potential interactions, all primers for the Vβ repertoire were adjusted to each other and the 24 Vα-primers by an oligoanalysis software program.

30 different Vβ-gene primers were tested in various combinations together with the 24 Vα-primers. This finally led to a set of nine Vβ primers (Vp1-9, Table 1), which covered all functional Vβ genes. Except Vp1, which is located on the leader segment, all primers are positioned on the Vβ-gene segment. In combination with a Cβ(1)-primer each of them efficiently amplified the corresponding Vβ-gene rearrangements, as shown by agarose gel-electrophoresis and ethidium-bromide staining (FIG. 8, A).

The capacity of the Vα- and Vβ-primer sets to amplify the full TCR Vβ- and Vα-gene repertoire in a single reaction when combined with each other was tested by multiplex RT-PCR with mRNA from peripheral blood T cells. After pre-amplification, the rearrangements of the different TCR Vβ-gene families were amplified from the multiplex-PCR product in 23 different nested PCR reactions using 23 different primers specific for the various TCR Vβ-gene families and a FAM-labelled Cβ(2)-primer essentially as described. The fragment lengths of the PCR products were analysed by spectratyping on a genetic sequencer. Amplification of each TCR Vβ-gene family yielded PCR products of the expected size range with Gaussian-like fragment-lengths distributions of the TCR rearrangements typical of polyclonal T-cell populations (FIG. 8, C).

In parallel, the TCR Vα-repertoire was amplified from the multiplex-PCR product using the 24 different Vα-primers in individual reactions. As shown by agarose-gel electrophoresis and ethidium bromide staining each of them yielded discrete PCR products representative of the amplified TCR Vα-rearrangements (FIG. 8, B). Thus, the multiplex RT-PCR conditions we had established for pre-amplification of the αβ-TCR repertoire were actually capable of amplifying both the full TCR Vβ- and Vα-repertoire in a single reaction.

4.3 Single Cell Analysis

The next step required amplifying the respective TCR Vβ-chain rearrangement from the pre-amplification product of single T cells. Because the multitude of 23 different Vβ-gene subfamilies prohibited a Vβ-specific nested PCR in one sample we introduced a universal primer sequence at the 5' end of the TCR β-chain PCR-products. For this purpose a unique 21-nucleotide sequence was designed lacking primer interactions or homologies with human genes and appended to the 5' end of the nine different Vp (Vp1-9) primers. 1 μl of the pre-amplification product was subjected to a run-off PCR using these elongated primers in a 10-μl PCR volume. This was followed by a third semi-nested PCR, which amplified the respective single cell TCR-Vβ rearrangement independent from the TCR Vβ-gene family using the universal primer together with a nested Cβ(2)-primer. The PCR strategy is shown in FIG. 9.

In parallel, the corresponding TCR Vα-rearrangement was amplified from the pre-amplification multiplex PCR in five different nested PCRs using five Vα-primer pools described by Seitz et al. The amplified TCR α- and β-chain rearrangements were then characterized by direct sequencing.

To test the efficiency of this approach on a single T-cell level, peripheral blood T cells were labelled with CD4- or CD8-monoclonal antibody-coated magnetic beads, and single T cells were aspirated with a 2-μl pipette in invert microscopy and transferred into the pre-amplification vial. When adjusted to the appropriate cell density, this technique easily allows identifying and isolating single rosette-forming T cells from cell suspensions of various origins (FIG. 10).

A total of 96 $CD4^+$ and 96 $CD8^+$ peripheral blood T cells were captured and analysed this way. In 82 $CD4^+$ (85.4%) and 76 (79.2%) $CD8^+$ T cells a TCR Vβ-rearrangement could be amplified and characterized by direct DNA sequencing of the PCR product, showing an efficiency of TCR β-chain amplification of greater than 80%. Among the analyzed rearrangements all functional TCR Vβ-gene families were represented except Vβ16, which is rarely rearranged in general. The prevalence of the other TCR Vβ-gene families reflected the average TCR Vβ-gene usage, with those TCRBV gene families showing a predominance that are generally most often observed in single cell analysis, as well. From each T cell rendering a β-chain rearrangement, a corresponding TCR α-chain could be obtained and confirmed by direct sequencing. Given the fact that manual single-cell aspiration likely has not be successful in every attempt we conclude that our approach allows the molecular characterization of the paired αβ-TCR rearrangements from virtually every single αβ-T cell.

4.4 Analysis of αβ-TCR Rearrangements of Single T Cells in Psoriasis

According to current concepts T-cell mediated autoimmune diseases result from the autoantigen-specific activation and clonal expansion of autoreactive T cells. We tested the capacity of our experimental approach to identify such pathogenic clonal T cells from inflammatory tissue lesions and characterize their paired αβ-TCR rearrangements, which encode the specificity for the putative autoantigens.

We focussed on psoriasis vulgaris, which is a T-cell mediated autoimmune disease of the skin. Former analyses of TCR β-chain repertoires of lesional psoriatic T-cell infiltrates by random amplification, cloning and sequencing of TCR cDNA from lesional biopsies had suggested dominant oligoclonal T-cell expansions, but the precise clonality and subtype of individual T cells has remained elusive.

A pathogenic autoimmune T-cell clone should be identifiable ex vivo in the pathogenic T-cell infiltrate as multiple T cells with identical αβ-TCR rearrangements. Based on this assumption, we established a stepwise protocol to identify lesional psoriatic T-cell clones on a single cell level and verify their presence within the tissue lesions.

Biopsies were taken from chronic psoriatic plaques and divided in two pieces. One half was subjected to the preparation of TCR β-chain cDNA, while the other half was seeded into culture to allow emigration of T cells from the inflammatory infiltrate, which occurs within 24 to 48 hours. T cells were harvested, labelled with CD4- or CD8-specific magnetic beads, and single $CD4^+$ or $CD8^+$ T cells were isolated and subjected to TCR β-chain analysis. TCR α-chain rearrangements of single T cells were only analysed in T-cell clones, i.e. if particular TCR Vβ-chain rearrangements were identified both in multiple T cells and within the second half of the biopsy specimen.

Lesional biopsies from four patients were examined this way. In patient #1, $CD4^+$ T cells and in patient #2, $CD8^+$ T cells were analysed. Two out of 40 $CD4^+$ (#1) or two out of 37 $CD8^+$ T cells (#2), respectively, had identical TCR Vβ- and Vα-rearrangements (Table 7). Using rearrangement-specific primers together with the corresponding Vβ-leader primers and direct sequencing of PCR products, each of the TCR Vβ-rearrangements could also be amplified from the corresponding biopsy sample, corroborating the clonal expansion of the corresponding T cells within the tissue lesion.

TABLE 7

Repetitive TCR β-chain rearrangements of single T cells from explant culture and presence of identical TCR rearrangements in the corresponding biopsy, blood or tonsil specimen;

| Pat. No. | Phenotype | Identical/ total number of T cells | Identical αβ-TCR rearrangements | TCR Vβ-chain rearrangements* TCR Vβ | | N(D)N | Jβ | | TCR β-chain CDR3 also identified in Corresponding skin lesion | PBL | Tonsil |
|---|---|---|---|---|---|---|---|---|---|---|---|
| 1 | CD4 | 2/40 | yes | 7.2 | CASS | PTSL | TDTG | 2.7 | + | ND | NA |
| 2 | CD8 | 2/37 | yes | 12.4 | CAS | TPSRGIS | YGYT | 1.2 | + | ND | NA |
| 3 | CD4 | 2/82 | yes | 18.1 | CASS | TTPGN | SGNT | 1.3 | + | + | + |
| | CD8 | 3/41 | yes | 7.2 | CASSL | SPVAY | SNQP | 1.5 | + | + | + |
| | | 2/41 | yes | 7.6 | CASSL | RPGTGGF | ETQY | 2.5 | + | + | − |
| | | 2/41 | yes | 7.7 | CASSL | NPS | SGNT | 1.3 | + | − | + |

*Deduced amino-acid sequence, one letter code;
NA, not available;
ND, not determined;
+, TCR CDR3 rearrangement identified;
−, TCR CDR3 not identified
In patient #3, $CD4^+$ and $CD8^+$ T cells were analysed. This patient had been tonsillectomized due to constant psoriasis flares in association with a recurrent streptococcal angina, which is the main infectious psoriasis trigger. Blood lymphocytes and fractions of the tonsils were available for analysis, as well. While one particular αβ-TCR rearrangement was found in two of 82 $CD4^+$ T cells (Table 7), three repetitive αβ-TCR rearrangements were identified in two or three of 41 $CD8^+$ T cells, respectively. All of these TCR-rearrangements were also identified within the corresponding second half of the biopsy. Most interestingly, the repetitive TCR Vβ-rearrangements of both $CD4^+$ and $CD8^+$ T cells could also be amplified from the PBL and/or the tonsillar tissue of the patient, indicating a systemic distribution of the corresponding T-cell clones.

4.5 Differential Distribution of $CD8^+$ T Clones in Epidermis and Dermis

While the majority of the T-cell infiltrate is located within the dermal compartment of psoriatic skin lesions, the development of psoriasis is crucially dependent on the accumulation of T cells within the epidermis, the majority of them being $CD8^+$. Thus, the actually pathogenic T cells may represent $CD8^+$ T cells, which have to enter the epidermis to promote psoriatic skin lesions. In the next two patients we therefore analysed the differential clonal distribution of $CD8^+$ T-cell clones within epidermis and dermis. For this purpose dermis and epidermis were dissociated from each other and seeded separately into culture.

Compartment-related analysis of single $CD8^+$ T cells documented that in both patients the representation of $CD8^+$ T-cell clones was stronger in the epidermal than the dermal compartment (Table 8). In patient #4, eight different αβ-TCR rearrangements were found in duplicates or triplicate among 52 epidermal $CD8^+$ T cells, and four repetitive αβ-TCR rearrangements were observed in both epidermal and dermal T cells. In patient #5, three different αβ-TCR rearrangements were selectively present in three, four or seven of 33 epidermal $CD8^+$ T cells, and two epidermal αβ-TCR rearrangements were seen in dermal T cells, as well. In the dermis, only one (patient #4) or two (patient #5) T-cell clones with identical αβ-TCR rearrangements were seen. Thus, epidermal T cells showed a clonal predominance over dermal T cells.

TABLE 8

Differential representation of CD8+ T-cell clones in dermis and epidermis.

| Patient | Clone No. | TCR Vβ-chain rearrangements* Vβ | | N(D)N | J | | Frequency in epidermis Identical/ total | Frequency in dermis Identical/ total |
|---|---|---|---|---|---|---|---|---|
| Patient # 4 | 1 | 4.1 | CASSQ | ENRG | GYAV | 2.7 | 2/52 | 1/36 |
| | 2+ | 6.5 | CASSY | SEGED | EAFF | 1.1 | 3/52 | 1/36 |
| | 3+ | 9.2 | CASS | PRGGE | NTIY | 1.3 | 2/52 | NO |
| | 4 | 11.2 | CASS | STLAGGP | DTQY | 2.3 | 2/52 | NO |
| | 5 | 11.2 | CASS | LGRL | QETQ | 2.5 | 2/52 | NO |
| | 6 | 11.3 | CASS | PAQ | — | — | 2/52 | 1/36 |
| | 7 | 18.1 | CAS | AGTGYF | QPQH | 1.5 | 2/52 | NO |
| | 8 | 19.1 | CAS | TLRSSG | NEKL | 1.4 | 2/52 | NO |
| | 9 | 6.1 | CAS | TELAGD | YNEQ | 2.1 | 1/52 | 1/36 |
| | 10 | 7.9 | CA | SWTGELG | GYTF | 1.2 | NO | 2/36 |
| Patient #5 | 1 | 11.3 | CASS | PRTSGG | YNEQ | 2.1 | 3/33 | NO |
| | 2 | 20.1 | CSAR | DQGQHR | TDTQ | 2.3 | 7/33 | NO |
| | 3 | 20.1 | CSAR | GGLGLMP | GELF | 2.2 | 4/33 | NO |
| | 4 | 4.1 | CASSQ | LTSESY | SYNE | 2.1 | 1/33 | 1/25 |
| | 5 | 6.1 | CAS | GWDRGT | FFGQ | 1.1 | 1/33 | 1/25 |
| | 1 | 3.1 | CASSQ | DLWTGGWG | TDTQ | 2.3 | NO | 2/25 |
| | 2 | 12.3 (4) | CASSL | ILGGD | EQYF | 2.7 | NO | 2/25 |

*deduced amino-acid sequence, one letter code;
+: T-cells in direct contact with APC;
NO, not observed; directly rearranged to Cβ without Jβ gene.

4.6 Generation of TCR Hybridomas

The paired αβ TCR rearrangements of the clonally expanded CD8+ T cells likely carry the antigen-specificity of the lesional psoriatic T-cell response. To use them for the identification of potential psoriatic antigens, recombinant TCR hybridomas were generated with the TCR rearrangements of several lesional CD8+ T-cell clones. For this purpose, the α and β-chain rearrangements of three different CD8+ clones were cloned and stably expressed as recombinant αβ-TCR clones in the mouse $58^{-/-}$ T cell hybridoma cell line together with the human CD8 molecule and a green fluorescent protein under the control of NFAT. Upon activation by CD3 monoclonal antibodies these hybridomas produced ample amounts of interleukin 2 (IL-2), as measured by an IL-2 Elisa, and became green fluorescent in UV-microscopy. Furthermore, they were activated by cells of the keratinocyte cell line, HaCaT, when this cell line was transfected with HLA-Cw6, which is the main risk allele conferring susceptibility to psoriasis.

REFERENCES

Bendle, G. M., et al. (2010). Nature Med 16:565-570

Bettinotti, M. P. et al. (2003) J. Immunol. Meth. 279:143-148.

Bielekova and Martin, J Mol. Med. 2001 October; 79(10): 552-65: Antigen-specific immunomodulation via altered peptide ligands Blank, U., Boitel, B., Mège, D., Ermonval, M., and Acuto, O. (1993). Analysis of tetanus toxin peptide/DR recognition by human T cell receptors reconstituted into a murine T cell hybridoma. Eur. J. Immunol. 23, 3057-3065.

Boon, T., Coulie, P. G., Van den Eynde, B. J., and Van der Bruggen, P. (2006). Human T cell responses against melanoma. Annu. Rev. Immunol. 24, 175-208.

Chen, E. H. et al. (2007) FEBS Letters 581:2181-2193.

Cohen, C. J. et al. (2007) Cancer Res. 67:3898-3903.

Cox, A. L., Skipper, J., Chen, Y., Henderson, R. A., Darrow, T. L., Shabanowitz, J., Engelhard, V. H., Hunt, D. F., and Singluff, C. L. (1994). Identification of a peptide recognized by five melanoma-specific human cytotoxic T cell lines. Science 264, 716-719.

Crawford, F., Huseby, E., White, J., Marrack, P., and Kappler, J. W. (2004). Mimotopes for alloreactive and conventional T cells in a peptide-MHC display library. PLoS Biology 2, 523-533.

Crawford, F., Jordan, K. R., Stadinski, B., Wang, Y. B., Huseby, E., Marrack, P., Slansky, J. E., and Kappler, J. W. (2006). Use of baculovirus MHC/peptide display libraries to characterize T-cell receptor ligands. Immunol. Rev. 210, 156-170.

Dalakas, M. C. (2006). Sporadic inclusion body myositis—diagnosis, pathogenesis and therapeutic strategies. Nature Clinical Practice Neurology 2, 437-447.

Durocher, Y. et al. (2002) Nucl. Acid Res. 30:e9.

Fiering, S., Northrop, J. P., Nolan, G. P., Mattila, P. S., Crabtree, G. R., and Herzenberg, L. A. (1990). Single cell assay of a transcription factor reveals a threshold in transcription activated by signals emanating from the T-cell antigen receptor. Genes Dev. 4, 1823-1834.

Fissolo, N., Haag, S., De Graaf, K. L., Drews, O., Stevanovic, S., Rammensee, H. G., and Weissert, R. (2009). Naturally presented peptides on major histocompatibility complex I and II molecules eluted from central nervous system of multiple sclerosis patients. Mol. Cell. Proteomics 8, 2090-2101.

Fontoura et al. Int Rev Immunol. 2005 September-December; 24(5-6):415-46: Antigen-specific therapies in multiple sclerosis: going beyond proteins and peptides.

Friese, M. A. and Fugger, L. (2009). Pathogenic CD8+ T cells in multiple sclerosis. Ann. Neurol. 66, 132-141.

Gluzman, Y. (1981). SV40-transformed simian cells support the replication of early SV40 mutants. Cell 23, 175-182.

Gotch, F., Rothbard, J., Howland, K., Townsend, A., and McMichael, A. (1987). Cytotoxic lymphocytes-T recognize a fragment of influenza-virus matrix protein in association with HLA-A2. Nature 326, 881.

Heim, R., Cubitt, A. B., and Tsien, R. Y. (1995). Improved green fluorescence. Nature 373, 663-664.

Ishizuka, J., Stewart-Jones, G. B. E., Van der Merwe, A., Bell, J. I., McMichael, A. J., and Jones, E. Y. (2008). The structural dynamics and energetics of an immunodominant T cell receptor are programmed by its Vb domain. Immunity 28, 171-182.

Karttunen, J. and Shastri, N. (1991). Measurements of ligand induced activation in single viable T cells using lacZ reporter gene. Proc. Natl. Acad. Sci. USA 88, 3972-3976.

Katakura, Y. et al. (1998) Meth. Cell Biol. 57:69-91.

Kuball, J. et al. (2007) Blood 109:2331-2338.

Lehner, P. J., Wang, E. C. Y., Moss, P. A. H., Williams, S., Platt, K., Friedman, S. M., Bell, J. I., and Borysiewicz, L. K. (1995). Human HLA-A0201-restricted cytotoxic T lymphocyte recognition of influenza A is dominated by T cells bearing the Vb17 gene segment. J. Exp. Med. 181, 79-91.

Marsh, S. G. et al. (2010) Tissue Antigens 75:291-455

Martinon, F., Mayor, A., and Tschopp, J. (2009). The inflammasomes: Guardians of the body. Annu. Rev. Immunol. 27, 229-265.

Murphy, K. et al. "Janeway's Immunobiology" 2008, 7th Edition, Garland Science, New York, ISBN 978-0-8153-4123-9

Murray, G. I. (2007) Acta Histochemica 109:171-176.

Nino-Vasquez, J. J., Allicotti, G., Borras, E., Wilson, D. B., Valmori, D., Simon, R., Martin, R., and Pinilla, C. (2005). A powerful combination: the use of positional scanning libraries and biometrical analysis to identify cross-reactive T cell epitopes. Mol. Immunol. 40, 1063-1074.

Ozaki, S. et al. (1988) J. Immunol. 141:71-78.

Pannetier, C. et al. 1995 Immunol. Today 16:176-181.

Pircher, H, Mak, T. W., Ballhausen, W., Rüedi, E., Hengartner, H., Zinkernagel, R. M., Bürki, K. (1989). T cell tolerance to MIs$^a$ encoded antigens in T cell receptor Vb8.1 chain transgenic mice. EMBO J. 8, 719-727.

Rammensee, H. -G., Bachmann, J Emmerich, N. P. N., Bachor, O. A., and Stevanovic, S. (1999). SYFPEITHI: Database for MHC ligands and peptide motifs. IG 50, 213-219.

Robinson J, et al. (2003) Nucleic Acids Research, 31:311-314.

Rudolph, M. G., Stanfield, R. L., and Wilson, I. A. (2006). How TCRs bind MHC, and coreceptotrs. Annu. Rev. Immunol. 24, 419-466.

Seitz, S., Schneider, C. K., Malotka, J., Nong, X., Engel, A. G., Wekerle, H., Hohlfeld, R., and Dornmair, K. (2006). Reconstitution of paired T cell receptor a- and b-chains from microdissected single cells of human inflammatory tissues. Proc. Natl. Acad. Sci. USA 103, 12057-12062.

Shaner, N. C. et al. Nat. Methods. (2005) 2:905-909.

Shirahata, S. et al. (1998) Meth Cell Biol. 52:111-145.

Smith, E. S., Mandokhot, A., Evans, E. E., Mueller, L., Borrello, M. A., Sahasrabudhe, D. M., and Zauderer, M. (2001). Lethality-based selection of recombinant genes in mammalian cells: Application to identifying tumor antigens. Nature Med. 7, 967-972.

Smith-Garvin, J. E., Koretzky, G. A., and Jordan, M. S. (2009). T cell activation. Annu. Rev. Immunol. 27, 591-619.

Stewart-Jones, G. B. E., McMichael, A. J., Bell, J. I., Stuart, D. I., and Jones, E. Y. (2003). A structural basis for immunodominant human T cell receptor recognition. Nature Immunol. 4, 657-663.

Stone, J. D. et al. (2009) Immunology 126:165-176

Suter-Crazzolara, C. et al. Meth. Cell Biol. (1995) 50:425-438.

Tung, J W et al (2007) Clin Lab Med. 27:453-468

Van der Bruggen, P., Traversari, C., Chomez, P., Lurquin, C., De Plaen, E., Van den Eynde, B., Knuth, A., and Boon, T. (1991). A gene encoding an antigen recognized by cytolytic T lymphocytes on a human melanoma. Science 254, 1643-1647.

van Loenen, M. M., et al. (2010). Proc. Natl. Acad. Sci. U.S. A 107, 10972-10977.

Voss, R. H. et al. (2008) J. Immunol. 180:391-401.

Walter, U. and Santamaria, P. (2005). CD8$^+$ T cells in autoimmunity. Curr. Opin. Immunol. 17, 624-631.

Wang, Y. B., Rubtsov, A., Heiser, R., White, J., Crawford, F., Marrack, P., and Kappler, J. W. (2005). Using a baculovirus display library to identify MHC class I mimotopes. Proc. Natl. Acad. Sci. USA 102, 2476-2481.

Weinhold, M. et al. (2007) J. Immunol. 179:5534-5542.

Wong, F. S., Karttunen, J., Dumont, C., Wen, L., Visintin, I., Pilip, I. M., Shastri, N., Pamer, E. G., and Janeway, C. A. (1999). Identification of an MHC class I-restricted autoantigen in type I diabetes by screening an organ-specific cDNA library. Nature Med. 5, 1026-1031.

Wucherpfennig, K. W., Allen, P. M., Celada, F., Cohen, I. R., De Boer, R., Garcia, K. C., Goldstein, B., Greenspan, R., Hafler, D., Hodgkin, P., Huseby, E. S., Krakauer, D. C., Nemazee, D., Perelson, A. S., Pinilla, C., Strong, R. K., and Sercarz, E. E. (2007). Polyspecificity of T cell and B cell receptor recognition. Semin. Immunol. 19, 216-224.

The invention claimed is:

1. A method of identifying a target antigen that binds to a T cell receptor complex comprising (a) contacting (aa) cells expressing (i) a functional T cell receptor complex comprising predefined matching T cell receptor α and β chains and a CD8αβ co-receptor; and (ii) a read-out system for T cell receptor complex activation, wherein the readout system comprises a green fluorescent protein (GFP) or a variant thereof; with (ab) antigen-presenting cells carrying (iii) peptide libraries, wherein the peptide libraries comprise a plurality of vectors comprising randomised nucleic acid sequences encoding peptides of 4-20 amino acids, wherein the peptides are potential target antigens of T cells and can be presented by MHC molecules; and (iv) MHC class I molecules recognised by the predefined matching T cell receptor and co-receptor of (i);

(b) assessing T cell receptor complex activation using said read-out system;

(c) isolating antigen-presenting cells that are in contact with the cells in which the read-out system indicates the predefined matching T cell receptor activation; and (d) identifying the target antigen or the nucleic acid molecule encoding said target antigen.

2. The method of claim 1, wherein the identification of the target antigen in (d) comprises sequencing of the nucleic acid molecule encoding said target antigen.

3. The method of claim 1, wherein the identification of the target antigen in (d) comprises the identification of at least one mimotope of the antigen.

4. The method of claim 1, wherein the antigen-presenting cells are cells capable of amplifying the peptide libraries.

5. The method of claim 1, wherein the read-out system comprises the activation of the reporter protein.

6. The method of claim 5, wherein the reporter protein is selected from the group consisting of fluorescent compounds, bioluminescent compounds and chemiluminescent compounds.

* * * * *

SEQUENCE LISTING

```
<160> NUMBER OF SEQ ID NOS: 112

<210> SEQ ID NO 1
<211> LENGTH: 20
<212> TYPE: DNA
<213> ORGANISM: Artificial sequence
<220> FEATURE:
<223> OTHER INFORMATION: /note="Description of artificial sequence:
      primer Vp1"
<220> FEATURE:
<221> NAME/KEY: variation
<222> LOCATION: 2
<223> OTHER INFORMATION: /replace="g"
<220> FEATURE:
<221> NAME/KEY: variation
<222> LOCATION: 3
<223> OTHER INFORMATION: /replace="t"

<400> SEQUENCE: 1
```

tcctttgtct cctgggagca 20

<210> SEQ ID NO 2
<211> LENGTH: 20
<212> TYPE: DNA
<213> ORGANISM: Artificial sequence
<220> FEATURE:
<223> OTHER INFORMATION: /note="Description of artificial sequence:
primer Vp2"

<400> SEQUENCE: 2
cctgaagtcg cccagactcc 20

<210> SEQ ID NO 3
<211> LENGTH: 22
<212> TYPE: DNA
<213> ORGANISM: Artificial sequence
<220> FEATURE:
<223> OTHER INFORMATION: /note="Description of artificial sequence:
primer Vp3"
<220> FEATURE:
<221> NAME/KEY: variation
<222> LOCATION: 6
<223> OTHER INFORMATION: /replace="g"
<220> FEATURE:
<221> NAME/KEY: variation
<222> LOCATION: 19
<223> OTHER INFORMATION: /replace="t"

<400> SEQUENCE: 3
gtcatccaga acccaagaca cc 22

<210> SEQ ID NO 4
<211> LENGTH: 24
<212> TYPE: DNA
<213> ORGANISM: Artificial sequence
<220> FEATURE:
<223> OTHER INFORMATION: /note="Description of artificial sequence:
primer Vp4"
<220> FEATURE:
<221> NAME/KEY: variation
<222> LOCATION: 3
<223> OTHER INFORMATION: /replace="t"
<220> FEATURE:
<221> NAME/KEY: variation
<222> LOCATION: 11
<223> OTHER INFORMATION: /replace="c"
<220> FEATURE:
<221> NAME/KEY: variation
<222> LOCATION: 14
<223> OTHER INFORMATION: /replace="c"

<400> SEQUENCE: 4
ggatatctgt aagagtggaa cctc 24

<210> SEQ ID NO 5
<211> LENGTH: 22
<212> TYPE: DNA
<213> ORGANISM: Artificial sequence
<220> FEATURE:
<223> OTHER INFORMATION: /note="Description of artificial sequence:
primer Vp5
<220> FEATURE:
<221> NAME/KEY: variation
<222> LOCATION: 21
<223> OTHER INFORMATION: /replace="c"

<400> SEQUENCE: 5
atgtactggt atcgacaaga tc 22

<210> SEQ ID NO 6
<211> LENGTH: 23
<212> TYPE: DNA
<213> ORGANISM: Artificial sequence
<220> FEATURE:
<223> OTHER INFORMATION: /note="Description of artificial sequence: primer Vp6"

<400> SEQUENCE: 6
cactgtggaa ggaacatcaa acc 23

<210> SEQ ID NO 7
<211> LENGTH: 21
<212> TYPE: DNA
<213> ORGANISM: Artificial sequence
<220> FEATURE:
<223> OTHER INFORMATION: /note="Description of artificial sequence: primer Vp7"
<220> FEATURE:
<221> NAME/KEY: variation
<222> LOCATION: 11
<223> OTHER INFORMATION: /replace="g"

<400> SEQUENCE: 7
tctccactct caagatccag c 21

<210> SEQ ID NO 8
<211> LENGTH: 26
<212> TYPE: DNA
<213> ORGANISM: Artificial sequence
<220> FEATURE:
<223> OTHER INFORMATION: /note="Description of artificial sequence: primer Vp8"
<220> FEATURE:
<221> NAME/KEY: variation
<222> LOCATION: 4
<223> OTHER INFORMATION: /replace="g"
<220> FEATURE:
<221> NAME/KEY: variation
<222> LOCATION: 10
<223> OTHER INFORMATION: /replace="g"
<220> FEATURE:
<221> NAME/KEY: variation
<222> LOCATION: 13
<223> OTHER INFORMATION: /replace="t"

<400> SEQUENCE: 8
cagaatgtaa atctcaggtg tgatcc 26

<210> SEQ ID NO 9
<211> LENGTH: 23
<212> TYPE: DNA
<213> ORGANISM: Artificial sequence
<220> FEATURE:
<223> OTHER INFORMATION: /note="Description of artificial sequence: primer Vp9"
<220> FEATURE:
<221> NAME/KEY: variation
<222> LOCATION: 7
<223> OTHER INFORMATION: /replace="t"
<220> FEATURE:
<221> NAME/KEY: variation
<222> LOCATION: 12
<223> OTHER INFORMATION: /replace="g"
<220> FEATURE:
<221> NAME/KEY: variation
<222> LOCATION: 14
<223> OTHER INFORMATION: /replace="t"

<400> SEQUENCE: 9
ccagacacca aaacacctgg tca 23

<210> SEQ ID NO 10
<211> LENGTH: 20
<212> TYPE: DNA
<213> ORGANISM: Artificial sequence
<220> FEATURE:
<223> OTHER INFORMATION: /note="Description of artificial sequence:
primer C alpha out"

<400> SEQUENCE: 10
gcagacagac ttgtcactgg 20

<210> SEQ ID NO 11
<211> LENGTH: 21
<212> TYPE: DNA
<213> ORGANISM: Artificial sequence
<220> FEATURE:
<223> OTHER INFORMATION: /note="Description of artificial sequence:
primer C beta out"

<400> SEQUENCE: 11
tggtcgggga agaagcctgt g 21

<210> SEQ ID NO 12
<211> LENGTH: 20
<212> TYPE: DNA
<213> ORGANISM: Artificial sequence
<220> FEATURE:
<223> OTHER INFORMATION: /note="Description of artificial sequence:
primer C alpha in"

<400> SEQUENCE: 12
agtctctcag ctggtacacg 20

<210> SEQ ID NO 13
<211> LENGTH: 22
<212> TYPE: DNA
<213> ORGANISM: Artificial sequence
<220> FEATURE:
<223> OTHER INFORMATION: /note="Description of artificial sequence:
primer UP"

<400> SEQUENCE: 13
acagcacgac ttccaagact ca 22

<210> SEQ ID NO 14
<211> LENGTH: 20
<212> TYPE: DNA
<213> ORGANISM: Artificial sequence
<220> FEATURE:
<223> OTHER INFORMATION: /note="Description of artificial sequence:
primer C beta in"

<400> SEQUENCE: 14
tctgatggct caaacacagc 20

<210> SEQ ID NO 15
<211> LENGTH: 19
<212> TYPE: DNA
<213> ORGANISM: Artificial sequence
<220> FEATURE:
<223> OTHER INFORMATION: /note="Description of artificial sequence:
primer V alpha-1(14)-for-out"
<220> FEATURE:
<221> NAME/KEY: variation
<222> LOCATION: 3
<223> OTHER INFORMATION: /replace="g"

<400> SEQUENCE: 15
agcagcctca ctggagttg 19

<210> SEQ ID NO 16
<211> LENGTH: 20
<212> TYPE: DNA
<213> ORGANISM: Artificial sequence
<220> FEATURE:
<223> OTHER INFORMATION: /note="Description of artificial sequence: primer V alpha-1(235)-for-out"

<400> SEQUENCE: 16
ctgaggtgca actactcatc 20

<210> SEQ ID NO 17
<211> LENGTH: 19
<212> TYPE: DNA
<213> ORGANISM: Artificial sequence
<220> FEATURE:
<223> OTHER INFORMATION: /note="Description of artificial sequence: primer V alpha-2-for-out"
<220> FEATURE:
<221> NAME/KEY: variation
<222> LOCATION: 3
<223> OTHER INFORMATION: /replace="g"

<400> SEQUENCE: 17
caatgttcca gagggagcc 19

<210> SEQ ID NO 18
<211> LENGTH: 21
<212> TYPE: DNA
<213> ORGANISM: Artificial sequence
<220> FEATURE:
<223> OTHER INFORMATION: /note="Description of artificial sequence: primer V alpha-3,25-for-out"
<220> FEATURE:
<221> NAME/KEY: variation
<222> LOCATION: 4
<223> OTHER INFORMATION: /replace="g"
<220> FEATURE:
<221> NAME/KEY: variation
<222> LOCATION: 8
<223> OTHER INFORMATION: /replace="t"
<220> FEATURE:
<221> NAME/KEY: variation
<222> LOCATION: 10
<223> OTHER INFORMATION: /replace="t"

<400> SEQUENCE: 18
gaaaatgcca ccatgaactg c 21

<210> SEQ ID NO 19
<211> LENGTH: 19
<212> TYPE: DNA
<213> ORGANISM: Artificial sequence
<220> FEATURE:
<223> OTHER INFORMATION: /note="Description of artificial sequence: primer V alpha-4,20-for-out"
<220> FEATURE:
<221> NAME/KEY: variation
<222> LOCATION: 1
<223> OTHER INFORMATION: /replace="t"

<400> SEQUENCE: 19
atgctaagac cacccagcc 19

<210> SEQ ID NO 20
<211> LENGTH: 21

```
<212> TYPE: DNA
<213> ORGANISM: Artificial sequence
<220> FEATURE:
<223> OTHER INFORMATION: /note="Description of artificial sequence:
      primer V alpha-5-for-out"

<400> SEQUENCE: 20

agatagaaca gaattccgag g                                              21


<210> SEQ ID NO 21
<211> LENGTH: 21
<212> TYPE: DNA
<213> ORGANISM: Artificial sequence
<220> FEATURE:
<223> OTHER INFORMATION: /note="Description of artificial sequence:
      primer V alpha-6,14-for-out"
<220> FEATURE:
<221> NAME/KEY: variation
<222> LOCATION: 1
<223> OTHER INFORMATION: /replace="g"
<220> FEATURE:
<221> NAME/KEY: variation
<222> LOCATION: 2
<223> OTHER INFORMATION: /replace="t"

<400> SEQUENCE: 21

actgcacata tgacaccagt g                                              21


<210> SEQ ID NO 22
<211> LENGTH: 19
<212> TYPE: DNA
<213> ORGANISM: Artificial sequence
<220> FEATURE:
<223> OTHER INFORMATION: /note="Description of artificial sequence:
      primer V alpha-7-for-out"

<400> SEQUENCE: 22

cacgtaccag acatctggg                                                 19


<210> SEQ ID NO 23
<211> LENGTH: 18
<212> TYPE: DNA
<213> ORGANISM: Artificial sequence
<220> FEATURE:
<223> OTHER INFORMATION: /note="Description of artificial sequence:
      primer V alpha-8,21-for-out"
<220> FEATURE:
<221> NAME/KEY: variation
<222> LOCATION: 7
<223> OTHER INFORMATION: /replace="t"
<220> FEATURE:
<221> NAME/KEY: variation
<222> LOCATION: 16
<223> OTHER INFORMATION: /replace="g"

<400> SEQUENCE: 23

cctgagcgtc caggaagg                                                  18


<210> SEQ ID NO 24
<211> LENGTH: 21
<212> TYPE: DNA
<213> ORGANISM: Artificial sequence
<220> FEATURE:
<223> OTHER INFORMATION: /note="Description of artificial sequence:
      primer V alpha-9-for-out"

<400> SEQUENCE: 24

gtgcaactat tcctattctg g                                              21
```

<210> SEQ ID NO 25
<211> LENGTH: 19
<212> TYPE: DNA
<213> ORGANISM: Artificial sequence
<220> FEATURE:
<223> OTHER INFORMATION: /note="Description of artificial sequence:
primer V alpha-10,24-for-out"
<220> FEATURE:
<221> NAME/KEY: variation
<222> LOCATION: 2
<223> OTHER INFORMATION: /replace="g"
<220> FEATURE:
<221> NAME/KEY: variation
<222> LOCATION: 13
<223> OTHER INFORMATION: /replace="t"

<400> SEQUENCE: 25
actggagcag agccctcag 19

<210> SEQ ID NO 26
<211> LENGTH: 19
<212> TYPE: DNA
<213> ORGANISM: Artificial sequence
<220> FEATURE:
<223> OTHER INFORMATION: /note="Description of artificial sequence:
primer V alpha-11-for-out"

<400> SEQUENCE: 26
tcttcagagg gagctgtgg 19

<210> SEQ ID NO 27
<211> LENGTH: 19
<212> TYPE: DNA
<213> ORGANISM: Artificial sequence
<220> FEATURE:
<223> OTHER INFORMATION: /note="Description of artificial sequence:
primer V alpha-12-for-out"

<400> SEQUENCE: 27
ggtggagaag gaggatgtg 19

<210> SEQ ID NO 28
<211> LENGTH: 19
<212> TYPE: DNA
<213> ORGANISM: Artificial sequence
<220> FEATURE:
<223> OTHER INFORMATION: /note="Description of artificial sequence:
primer V alpha-13,19,26-for-out"
<220> FEATURE:
<221> NAME/KEY: variation
<222> LOCATION: 1
<223> OTHER INFORMATION: /replace="g"
<220> FEATURE:
<221> NAME/KEY: variation
<222> LOCATION: 4
<223> OTHER INFORMATION: /replace="g"

<400> SEQUENCE: 28
caactggagc agagtcctc 19

<210> SEQ ID NO 29
<211> LENGTH: 18
<212> TYPE: DNA
<213> ORGANISM: Artificial sequence
<220> FEATURE:
<223> OTHER INFORMATION: /note="Description of artificial sequence:
primer V alpha-15-for-out"

<400> SEQUENCE: 29
cctgagtgtc cgagaggg 18

<210> SEQ ID NO 30
<211> LENGTH: 21
<212> TYPE: DNA
<213> ORGANISM: Artificial sequence
<220> FEATURE:
<223> OTHER INFORMATION: /note="Description of artificial sequence: primer V alpha-16-for-out"

<400> SEQUENCE: 30
atgcacctat tcagtctctg g 21

<210> SEQ ID NO 31
<211> LENGTH: 20
<212> TYPE: DNA
<213> ORGANISM: Artificial sequence
<220> FEATURE:
<223> OTHER INFORMATION: /note="Description of artificial sequence: primer V alpha-17-for-out"

<400> SEQUENCE: 31
tgatagtcca gaaaggaggg 20

<210> SEQ ID NO 32
<211> LENGTH: 20
<212> TYPE: DNA
<213> ORGANISM: Artificial sequence
<220> FEATURE:
<223> OTHER INFORMATION: /note="Description of artificial sequence: primer V alpha-18-for-out"

<400> SEQUENCE: 32
gtcactgcat gttcaggagg 20

<210> SEQ ID NO 33
<211> LENGTH: 20
<212> TYPE: DNA
<213> ORGANISM: Artificial sequence
<220> FEATURE:
<223> OTHER INFORMATION: /note="Description of artificial sequence: primer V alpha-22,31-for-out"
<220> FEATURE:
<221> NAME/KEY: variation
<222> LOCATION: 5
<223> OTHER INFORMATION: /replace="t"

<400> SEQUENCE: 33
ccctaccctt ttctggtatg 20

<210> SEQ ID NO 34
<211> LENGTH: 19
<212> TYPE: DNA
<213> ORGANISM: Artificial sequence
<220> FEATURE:
<223> OTHER INFORMATION: /note="Description of artificial sequence: primer V alpha-23,30-for-out"
<220> FEATURE:
<221> NAME/KEY: variation
<222> LOCATION: 5
<223> OTHER INFORMATION: /replace="g"
<220> FEATURE:
<221> NAME/KEY: variation
<222> LOCATION: 8
<223> OTHER INFORMATION: /replace="t"

<400> SEQUENCE: 34
ggcaagaccc tgggaaagg 19

<210> SEQ ID NO 35
<211> LENGTH: 19
<212> TYPE: DNA
<213> ORGANISM: Artificial sequence
<220> FEATURE:
<223> OTHER INFORMATION: /note="Description of artificial sequence:
primer V alpha-27-for-out"

<400> SEQUENCE: 35
ctgttcctga gcatgcagg 19

<210> SEQ ID NO 36
<211> LENGTH: 20
<212> TYPE: DNA
<213> ORGANISM: Artificial sequence
<220> FEATURE:
<223> OTHER INFORMATION: /note="Description of artificial sequence:
primer V alpha-28-for-out"

<400> SEQUENCE: 36
agacaaggtg gtacaaagcc 20

<210> SEQ ID NO 37
<211> LENGTH: 19
<212> TYPE: DNA
<213> ORGANISM: Artificial sequence
<220> FEATURE:
<223> OTHER INFORMATION: /note="Description of artificial sequence:
primer V alpha-29-for-out"

<400> SEQUENCE: 37
caaccagtgc agagtcctc 19

<210> SEQ ID NO 38
<211> LENGTH: 20
<212> TYPE: DNA
<213> ORGANISM: Artificial sequence
<220> FEATURE:
<223> OTHER INFORMATION: /note="Description of artificial sequence:
primer V alpha-32-for-out"

<400> SEQUENCE: 38
gcatgtacaa gaaggagagg 20

<210> SEQ ID NO 39
<211> LENGTH: 41
<212> TYPE: DNA
<213> ORGANISM: Artificial sequence
<220> FEATURE:
<223> OTHER INFORMATION: /note="Description of artificial sequence:
primer Vp1+"
<220> FEATURE:
<221> NAME/KEY: variation
<222> LOCATION: 24
<223> OTHER INFORMATION: /replace="t"

<400> SEQUENCE: 39
acagcacgac ttccaagact cacctttgtc tcctgggagc a 41

<210> SEQ ID NO 40
<211> LENGTH: 42
<212> TYPE: DNA
<213> ORGANISM: Artificial sequence
<220> FEATURE:
<223> OTHER INFORMATION: /note="Description of artificial sequence:
primer Vp2+"

<400> SEQUENCE: 40

-continued acagcacgac ttccaagact cacctgatgt cgcccagact cc 42

<210> SEQ ID NO 41
<211> LENGTH: 44
<212> TYPE: DNA
<213> ORGANISM: Artificial sequence
<220> FEATURE:
<223> OTHER INFORMATION: /note="Description of artificial sequence: primer Vp3+"
<220> FEATURE:
<221> NAME/KEY: variation
<222> LOCATION: 28
<223> OTHER INFORMATION: /replace="g"
<220> FEATURE:
<221> NAME/KEY: variation
<222> LOCATION: 41
<223> OTHER INFORMATION: /replace="t"

<400> SEQUENCE: 41
acagcacgac ttccaagact cagtcatcca gaacccaaga cacc 44

<210> SEQ ID NO 42
<211> LENGTH: 46
<212> TYPE: DNA
<213> ORGANISM: Artificial sequence
<220> FEATURE:
<223> OTHER INFORMATION: /note="Description of artificial sequence: primer Vp4+"
<220> FEATURE:
<221> NAME/KEY: variation
<222> LOCATION: 25
<223> OTHER INFORMATION: /replace="t"
<220> FEATURE:
<221> NAME/KEY: variation
<222> LOCATION: 33
<223> OTHER INFORMATION: /replace="c"
<220> FEATURE:
<221> NAME/KEY: variation
<222> LOCATION: 36
<223> OTHER INFORMATION: /replace="c"

<400> SEQUENCE: 42
acagcacgac ttccaagact caggatatct gtaagagtgg aacctc 46

<210> SEQ ID NO 43
<211> LENGTH: 44
<212> TYPE: DNA
<213> ORGANISM: Artificial sequence
<220> FEATURE:
<223> OTHER INFORMATION: /note="Description of artificial sequence: primer Vp5+"
<220> FEATURE:
<221> NAME/KEY: variation
<222> LOCATION: 43
<223> OTHER INFORMATION: /replace="t"

<400> SEQUENCE: 43
acagcacgac ttccaagact caatgtactg gtatcgacaa gacc 44

<210> SEQ ID NO 44
<211> LENGTH: 45
<212> TYPE: DNA
<213> ORGANISM: Artificial sequence
<220> FEATURE:
<223> OTHER INFORMATION: /note="Description of artificial sequence: primer Vp6+"

<400> SEQUENCE: 44
acagcacgac ttccaagact cacactgtgg aaggaacatc aaacc 45

<210> SEQ ID NO 45
<211> LENGTH: 43
<212> TYPE: DNA
<213> ORGANISM: Artificial sequence
<220> FEATURE:
<223> OTHER INFORMATION: /note="Description of artificial sequence: primer Vp7+"
<220> FEATURE:
<221> NAME/KEY: variation
<222> LOCATION: 33
<223> OTHER INFORMATION: /replace="g"

<400> SEQUENCE: 45
acagcacgac ttccaagact catctccact ctcaagatcc agc 43

<210> SEQ ID NO 46
<211> LENGTH: 48
<212> TYPE: DNA
<213> ORGANISM: Artificial sequence
<220> FEATURE:
<223> OTHER INFORMATION: /note="Description of artificial sequence: primer Vp8+"
<220> FEATURE:
<221> NAME/KEY: variation
<222> LOCATION: 26
<223> OTHER INFORMATION: /replace="g"
<220> FEATURE:
<221> NAME/KEY: variation
<222> LOCATION: 32
<223> OTHER INFORMATION: /replace="g"
<220> FEATURE:
<221> NAME/KEY: variation
<222> LOCATION: 35
<223> OTHER INFORMATION: /replace="t"

<400> SEQUENCE: 46
acagcacgac ttccaagact cacagaatgt aaatctcagg tgtgatcc 48

<210> SEQ ID NO 47
<211> LENGTH: 45
<212> TYPE: DNA
<213> ORGANISM: Artificial sequence
<220> FEATURE:
<223> OTHER INFORMATION: /note="Description of artificial sequence: primer Vp9+"
<220> FEATURE:
<221> NAME/KEY: variation
<222> LOCATION: 29
<223> OTHER INFORMATION: /replace="t"
<220> FEATURE:
<221> NAME/KEY: variation
<222> LOCATION: 34
<223> OTHER INFORMATION: /replace="g"
<220> FEATURE:
<221> NAME/KEY: variation
<222> LOCATION: 36
<223> OTHER INFORMATION: /replace="t"

<400> SEQUENCE: 47
acagcacgac ttccaagact catcagacac caaaacacct ggtca 45

<210> SEQ ID NO 48
<211> LENGTH: 21
<212> TYPE: DNA
<213> ORGANISM: Artificial sequence
<220> FEATURE:
<223> OTHER INFORMATION: /note="Description of artificial sequence: primer V alpha-4/1-for-in"

<400> SEQUENCE: 48
acagaagaca gaaagtccag c 21

<210> SEQ ID NO 49
<211> LENGTH: 20
<212> TYPE: DNA
<213> ORGANISM: Artificial sequence
<220> FEATURE:
<223> OTHER INFORMATION: /note="Description of artificial sequence: primer V alpha-4/2-for-in"

<400> SEQUENCE: 49
gtccagtacc ttgatcctgc 20

<210> SEQ ID NO 50
<211> LENGTH: 21
<212> TYPE: DNA
<213> ORGANISM: Artificial sequence
<220> FEATURE:
<223> OTHER INFORMATION: /note="Description of artificial sequence: primer V alpha-6-for-in"

<400> SEQUENCE: 50
gcaaaatgca acagaaggtc g 21

<210> SEQ ID NO 51
<211> LENGTH: 20
<212> TYPE: DNA
<213> ORGANISM: Artificial sequence
<220> FEATURE:
<223> OTHER INFORMATION: /note="Description of artificial sequence: primer V alpha-8/1-for-in"

<400> SEQUENCE: 51
cagtgcctca aactacttcc 20

<210> SEQ ID NO 52
<211> LENGTH: 21
<212> TYPE: DNA
<213> ORGANISM: Artificial sequence
<220> FEATURE:
<223> OTHER INFORMATION: /note="Description of artificial sequence: primer V alpha-8/2-for-in"

<400> SEQUENCE: 52
gcctcagact acttcatttg g 21

<210> SEQ ID NO 53
<211> LENGTH: 21
<212> TYPE: DNA
<213> ORGANISM: Artificial sequence
<220> FEATURE:
<223> OTHER INFORMATION: /note="Description of artificial sequence: primer V alpha-14-for-in"

<400> SEQUENCE: 53
acagaatgca acggagaatc g 21

<210> SEQ ID NO 54
<211> LENGTH: 20
<212> TYPE: DNA
<213> ORGANISM: Artificial sequence
<220> FEATURE:
<223> OTHER INFORMATION: /note="Description of artificial sequence: primer V alpha-24-for-in"

<400> SEQUENCE: 54
ccttcagcaa cttaaggtgg 20

-continued

<210> SEQ ID NO 55
<211> LENGTH: 19
<212> TYPE: DNA
<213> ORGANISM: Artificial sequence
<220> FEATURE:
<223> OTHER INFORMATION: /note="Description of artificial sequence: primer V alpha-28-for-in"

<400> SEQUENCE: 55
tctctggttg tccacgagg 19

<210> SEQ ID NO 56
<211> LENGTH: 20
<212> TYPE: DNA
<213> ORGANISM: Artificial sequence
<220> FEATURE:
<223> OTHER INFORMATION: /note="Description of artificial sequence: primer V alpha-2/1-for-in"

<400> SEQUENCE: 56
tggaaggttt acagcacagc 20

<210> SEQ ID NO 57
<211> LENGTH: 20
<212> TYPE: DNA
<213> ORGANISM: Artificial sequence
<220> FEATURE:
<223> OTHER INFORMATION: /note="Description of artificial sequence: primer V alpha-2/2-for-in"

<400> SEQUENCE: 57
tggaaggttt acagcacagg 20

<210> SEQ ID NO 58
<211> LENGTH: 21
<212> TYPE: DNA
<213> ORGANISM: Artificial sequence
<220> FEATURE:
<223> OTHER INFORMATION: /note="Description of artificial sequence: primer V alpha-5-for-in"

<400> SEQUENCE: 58
cagcatactt acagtggtac c 21

<210> SEQ ID NO 59
<211> LENGTH: 20
<212> TYPE: DNA
<213> ORGANISM: Artificial sequence
<220> FEATURE:
<223> OTHER INFORMATION: /note="Description of artificial sequence: primer V alpha-10-for-in"

<400> SEQUENCE: 59
tcactgtgta ctgcaactcc 20

<210> SEQ ID NO 60
<211> LENGTH: 20
<212> TYPE: DNA
<213> ORGANISM: Artificial sequence
<220> FEATURE:
<223> OTHER INFORMATION: /note="Description of artificial sequence: primer V alpha-12-for-in"

<400> SEQUENCE: 60
tacaagcaac caccaagtgg 20

<210> SEQ ID NO 61

```
<211> LENGTH: 20
<212> TYPE: DNA
<213> ORGANISM: Artificial sequence
<220> FEATURE:
<223> OTHER INFORMATION: /note="Description of artificial sequence:
      primer V alpha-22-for-in"

<400> SEQUENCE: 61

aggctgatga caagggaagc                                                20


<210> SEQ ID NO 62
<211> LENGTH: 20
<212> TYPE: DNA
<213> ORGANISM: Artificial sequence
<220> FEATURE:
<223> OTHER INFORMATION: /note="Description of artificial sequence:
      primer V alpha-31-for-in"

<400> SEQUENCE: 62

gtggaatacc ccagcaaacc                                                20


<210> SEQ ID NO 63
<211> LENGTH: 20
<212> TYPE: DNA
<213> ORGANISM: Artificial sequence
<220> FEATURE:
<223> OTHER INFORMATION: /note="Description of artificial sequence:
      primer V alpha-7-for-in"

<400> SEQUENCE: 63

ctccagatga aagactctgc                                                20


<210> SEQ ID NO 64
<211> LENGTH: 19
<212> TYPE: DNA
<213> ORGANISM: Artificial sequence
<220> FEATURE:
<223> OTHER INFORMATION: /note="Description of artificial sequence:
      primer V alpha-13-for-in"

<400> SEQUENCE: 64

ttaagcgcca cgactgtcg                                                 19


<210> SEQ ID NO 65
<211> LENGTH: 21
<212> TYPE: DNA
<213> ORGANISM: Artificial sequence
<220> FEATURE:
<223> OTHER INFORMATION: /note="Description of artificial sequence:
      primer V alpha-17-for-in"

<400> SEQUENCE: 65

ctgtgcttat gagaacactg c                                              21


<210> SEQ ID NO 66
<211> LENGTH: 20
<212> TYPE: DNA
<213> ORGANISM: Artificial sequence
<220> FEATURE:
<223> OTHER INFORMATION: /note="Description of artificial sequence:
      primer V alpha-18-for-in"

<400> SEQUENCE: 66

ccttacactg gtacagatgg                                                20


<210> SEQ ID NO 67
<211> LENGTH: 20
```

```
<212> TYPE: DNA
<213> ORGANISM: Artificial sequence
<220> FEATURE:
<223> OTHER INFORMATION: /note="Description of artificial sequence:
      primer V alpha-21-for-in"

<400> SEQUENCE: 67

tgctgaaggt cctacattcc                                                  20


<210> SEQ ID NO 68
<211> LENGTH: 20
<212> TYPE: DNA
<213> ORGANISM: Artificial sequence
<220> FEATURE:
<223> OTHER INFORMATION: /note="Description of artificial sequence:
      primer V alpha-23-for-in"

<400> SEQUENCE: 68

gtggaagact taatgcctcg                                                  20


<210> SEQ ID NO 69
<211> LENGTH: 20
<212> TYPE: DNA
<213> ORGANISM: Artificial sequence
<220> FEATURE:
<223> OTHER INFORMATION: /note="Description of artificial sequence:
      primer V alpha-32-for-in"

<400> SEQUENCE: 69

tcaccacgta ctgcaattcc                                                  20


<210> SEQ ID NO 70
<211> LENGTH: 20
<212> TYPE: DNA
<213> ORGANISM: Artificial sequence
<220> FEATURE:
<223> OTHER INFORMATION: /note="Description of artificial sequence:
      primer V alpha-3-for-in"

<400> SEQUENCE: 70

ttcaggtaga ggccttgtcc                                                  20


<210> SEQ ID NO 71
<211> LENGTH: 20
<212> TYPE: DNA
<213> ORGANISM: Artificial sequence
<220> FEATURE:
<223> OTHER INFORMATION: /note="Description of artificial sequence:
      primer V alpha-11-for-in"

<400> SEQUENCE: 71

agggacgata caacatgacc                                                  20


<210> SEQ ID NO 72
<211> LENGTH: 20
<212> TYPE: DNA
<213> ORGANISM: Artificial sequence
<220> FEATURE:
<223> OTHER INFORMATION: /note="Description of artificial sequence:
      primer V alpha-15-for-in"

<400> SEQUENCE: 72

cctccaccta cttatactgg                                                  20


<210> SEQ ID NO 73
<211> LENGTH: 19
<212> TYPE: DNA
```

<213> ORGANISM: Artificial sequence
<220> FEATURE:
<223> OTHER INFORMATION: /note="Description of artificial sequence: primer V alpha-19-for-in"

<400> SEQUENCE: 73
cctgcacatc acagcctcc 19

<210> SEQ ID NO 74
<211> LENGTH: 20
<212> TYPE: DNA
<213> ORGANISM: Artificial sequence
<220> FEATURE:
<223> OTHER INFORMATION: /note="Description of artificial sequence: primer V alpha-25-for-in"

<400> SEQUENCE: 74
agactgactg ctcagtttgg 20

<210> SEQ ID NO 75
<211> LENGTH: 19
<212> TYPE: DNA
<213> ORGANISM: Artificial sequence
<220> FEATURE:
<223> OTHER INFORMATION: /note="Description of artificial sequence: primer V alpha-26-for-in"

<400> SEQUENCE: 75
cctgcatatc acagcctcc 19

<210> SEQ ID NO 76
<211> LENGTH: 19
<212> TYPE: DNA
<213> ORGANISM: Artificial sequence
<220> FEATURE:
<223> OTHER INFORMATION: /note="Description of artificial sequence: primer V alpha-29-for-in"

<400> SEQUENCE: 76
actgcagttc ctccaaggc 19

<210> SEQ ID NO 77
<211> LENGTH: 21
<212> TYPE: DNA
<213> ORGANISM: Artificial sequence
<220> FEATURE:
<223> OTHER INFORMATION: /note="Description of artificial sequence: primer V alpha-1/235-for-in"

<400> SEQUENCE: 77
aaggcatcaa cggttttgag g 21

<210> SEQ ID NO 78
<211> LENGTH: 19
<212> TYPE: DNA
<213> ORGANISM: Artificial sequence
<220> FEATURE:
<223> OTHER INFORMATION: /note="Description of artificial sequence: primer V alpha-1/14-for-in"

<400> SEQUENCE: 78
ctgaggaaac cctctgtgc 19

<210> SEQ ID NO 79
<211> LENGTH: 21
<212> TYPE: DNA
<213> ORGANISM: Artificial sequence
<220> FEATURE:
<223> OTHER INFORMATION: /note="Description of artificial sequence: primer V alpha-9-for-in"

<400> SEQUENCE: 79
atctttccac ctgaagaaac c 21

<210> SEQ ID NO 80
<211> LENGTH: 20
<212> TYPE: DNA
<213> ORGANISM: Artificial sequence
<220> FEATURE:
<223> OTHER INFORMATION: /note="Description of artificial sequence: primer V alpha-16-for-in"

<400> SEQUENCE: 80
tccttccacc tgaagaaacc 20

<210> SEQ ID NO 81
<211> LENGTH: 20
<212> TYPE: DNA
<213> ORGANISM: Artificial sequence
<220> FEATURE:
<223> OTHER INFORMATION: /note="Description of artificial sequence: primer V alpha-20-for-in"

<400> SEQUENCE: 81
acgtggtacc aacagtttcc 20

<210> SEQ ID NO 82
<211> LENGTH: 21
<212> TYPE: DNA
<213> ORGANISM: Artificial sequence
<220> FEATURE:
<223> OTHER INFORMATION: /note="Description of artificial sequence: primer V alpha-27-for-in"

<400> SEQUENCE: 82
acttcagaca gactgtattg g 21

<210> SEQ ID NO 83
<211> LENGTH: 20
<212> TYPE: DNA
<213> ORGANISM: Artificial sequence
<220> FEATURE:
<223> OTHER INFORMATION: /note="Description of artificial sequence: primer V alpha-30-for-in"

<400> SEQUENCE: 83
ctcttcaccc tgtattcagc 20

<210> SEQ ID NO 84
<211> LENGTH: 20
<212> TYPE: DNA
<213> ORGANISM: Artificial sequence
<220> FEATURE:
<223> OTHER INFORMATION: /note="Description of artificial sequence: primer pcDNA-for-1"

<400> SEQUENCE: 84
cactgcttac tggcttatcg 20

<210> SEQ ID NO 85
<211> LENGTH: 20
<212> TYPE: DNA
<213> ORGANISM: Artificial sequence
<220> FEATURE:

```
<223> OTHER INFORMATION: /note="Description of artificial sequence:
      primer pcDNA-rev-1"

<400> SEQUENCE: 85

actagaaggc acagtcgagg                                                    20

<210> SEQ ID NO 86
<211> LENGTH: 24
<212> TYPE: DNA
<213> ORGANISM: Artificial sequence
<220> FEATURE:
<223> OTHER INFORMATION: /note="Description of artificial sequence:
      primer pcDNA-for-2-TOPO(Mimo 1)"

<400> SEQUENCE: 86

cacccgactc actataggga gacc                                               24

<210> SEQ ID NO 87
<211> LENGTH: 21
<212> TYPE: DNA
<213> ORGANISM: Artificial sequence
<220> FEATURE:
<223> OTHER INFORMATION: /note="Description of artificial sequence:
      primer pcDNA-2nd-for-TOPO(Mimo 2,3)"

<400> SEQUENCE: 87

cacctccggc gcgccaccat g                                                  21

<210> SEQ ID NO 88
<211> LENGTH: 21
<212> TYPE: DNA
<213> ORGANISM: Artificial sequence
<220> FEATURE:
<223> OTHER INFORMATION: /note="Description of artificial sequence:
      primer pcDNA-rev-2(Mimo 1)"

<400> SEQUENCE: 88

ctgatcagcg ggtttaaact c                                                  21

<210> SEQ ID NO 89
<211> LENGTH: 20
<212> TYPE: DNA
<213> ORGANISM: Artificial sequence
<220> FEATURE:
<223> OTHER INFORMATION: /note="Description of artificial sequence:
      primer pcDNA-rev-3(Mimo 2, 3)"

<400> SEQUENCE: 89

tggtgatggt gatgatgacc                                                    20

<210> SEQ ID NO 90
<211> LENGTH: 17
<212> TYPE: DNA
<213> ORGANISM: Artificial sequence
<220> FEATURE:
<223> OTHER INFORMATION: /note="Description of artificial sequence:
      primer pcDNA-2nd-for"

<400> SEQUENCE: 90

tccggcgcgc caccatg                                                       17

<210> SEQ ID NO 91
<211> LENGTH: 18
<212> TYPE: DNA
<213> ORGANISM: Artificial sequence
<220> FEATURE:
<223> OTHER INFORMATION: /note="Description of artificial sequence:
```

primer pcDNA-2nd-rev-10"

<400> SEQUENCE: 91
ctagactcga gcggccgc 18

<210> SEQ ID NO 92
<211> LENGTH: 30
<212> TYPE: DNA
<213> ORGANISM: Artificial sequence
<220> FEATURE:
<223> OTHER INFORMATION: /note="Description of artificial sequence: primer JM22-Valpha-for"

<400> SEQUENCE: 92
tgtgtcgaca tggtcctgaa attctccgtg 30

<210> SEQ ID NO 93
<211> LENGTH: 32
<212> TYPE: DNA
<213> ORGANISM: Artificial sequence
<220> FEATURE:
<223> OTHER INFORMATION: /note="Description of artificial sequence: primer JM22-VJalpha-rev"

<400> SEQUENCE: 93
ttgggatccc gctcctgcac agaggtagtg gc 32

<210> SEQ ID NO 94
<211> LENGTH: 33
<212> TYPE: DNA
<213> ORGANISM: Artificial sequence
<220> FEATURE:
<223> OTHER INFORMATION: /note="Description of artificial sequence: primer JM22-Jalpha-for"

<400> SEQUENCE: 94
gagggatccc aaggaaatct catctttgga aaa 33

<210> SEQ ID NO 95
<211> LENGTH: 21
<212> TYPE: DNA
<213> ORGANISM: Artificial sequence
<220> FEATURE:
<223> OTHER INFORMATION: /note="Description of artificial sequence: primer Calpha PvuII-rev"

<400> SEQUENCE: 95
agcactgttg ctcttgaagt c 21

<210> SEQ ID NO 96
<211> LENGTH: 20
<212> TYPE: DNA
<213> ORGANISM: Artificial sequence
<220> FEATURE:
<223> OTHER INFORMATION: /note="Description of artificial sequence: primer JM22-Vbeta-Kpn-for"

<400> SEQUENCE: 96
catgtactgg taccgacagg 20

<210> SEQ ID NO 97
<211> LENGTH: 52
<212> TYPE: DNA
<213> ORGANISM: Artificial sequence
<220> FEATURE:
<223> OTHER INFORMATION: /note="Description of artificial sequence: primer JM22-VJbeta-Sca-rev"

<400> SEQUENCE: 97
ccgaagtact gctcgtagga gctcctcgaa ctactggcac agagatagaa ag 52

<210> SEQ ID NO 98
<211> LENGTH: 36
<212> TYPE: DNA
<213> ORGANISM: Artificial sequence
<220> FEATURE:
<223> OTHER INFORMATION: /note="Description of artificial sequence: primer hCD8a-Not-for"

<400> SEQUENCE: 98
ataagaatgc ggccgcatgg ccttaccagt gaccgc 36

<210> SEQ ID NO 99
<211> LENGTH: 28
<212> TYPE: DNA
<213> ORGANISM: Artificial sequence
<220> FEATURE:
<223> OTHER INFORMATION: /note="Description of artificial sequence: primer hCD8a-EcoRI-rev"

<400> SEQUENCE: 99
ggaattctta gacgtatcac gccgaaag 28

<210> SEQ ID NO 100
<211> LENGTH: 27
<212> TYPE: DNA
<213> ORGANISM: Artificial sequence
<220> FEATURE:
<223> OTHER INFORMATION: /note="Description of artificial sequence: primer hCD8b-Mlu-Mut"

<400> SEQUENCE: 100
tcgacgcgta tgcgaccgcg gctgtgg 27

<210> SEQ ID NO 101
<211> LENGTH: 35
<212> TYPE: DNA
<213> ORGANISM: Artificial sequence
<220> FEATURE:
<223> OTHER INFORMATION: /note="Description of artificial sequence: primer hCD8b-Xho-rev"

<400> SEQUENCE: 101
ccgctcgagt tatttgtaaa attgtttcat gaaac 35

<210> SEQ ID NO 102
<211> LENGTH: 23
<212> TYPE: DNA
<213> ORGANISM: Artificial sequence
<220> FEATURE:
<223> OTHER INFORMATION: /note="Description of artificial sequence: primer sGFP-Eco-for"

<400> SEQUENCE: 102
tcgaattcgc caccatggtg agc 23

<210> SEQ ID NO 103
<211> LENGTH: 26
<212> TYPE: DNA
<213> ORGANISM: Artificial sequence
<220> FEATURE:
<223> OTHER INFORMATION: /note="Description of artificial sequence: primer sGFP-Xho-rev"

<400> SEQUENCE: 103
gactcgagag cttagtgatg gtgatg 26

<210> SEQ ID NO 104
<211> LENGTH: 27
<212> TYPE: DNA
<213> ORGANISM: Artificial sequence
<220> FEATURE:
<223> OTHER INFORMATION: /note="Description of artificial sequence: primerHLA-A0101-lead"

<400> SEQUENCE: 104
ctcgtcgaca tggccgtcat ggcgccc 27

<210> SEQ ID NO 105
<211> LENGTH: 30
<212> TYPE: DNA
<213> ORGANISM: Artificial sequence
<220> FEATURE:
<223> OTHER INFORMATION: /note="Description of artificial sequence: primer HLA-A0101-end"

<400> SEQUENCE: 105
tacggatcct cacactttac aagctgtgag 30

<210> SEQ ID NO 106
<211> LENGTH: 23
<212> TYPE: DNA
<213> ORGANISM: Artificial sequence
<220> FEATURE:
<223> OTHER INFORMATION: /note="Description of artificial sequence: primer pcDNArc-MCS-for"

<400> SEQUENCE: 106
gatccggcgc gcccctgcag ggc 23

<210> SEQ ID NO 107
<211> LENGTH: 23
<212> TYPE: DNA
<213> ORGANISM: Artificial sequence
<220> FEATURE:
<223> OTHER INFORMATION: /note="Description of artificial sequence: primer pcDNArc-MCS-rev"

<400> SEQUENCE: 107
ggccgccctg caggggcgcg ccg 23

<210> SEQ ID NO 108
<211> LENGTH: 44
<212> TYPE: DNA
<213> ORGANISM: Artificial sequence
<220> FEATURE:
<223> OTHER INFORMATION: /note="Description of artificial sequence: primer N27-flu-Asc-for"

<400> SEQUENCE: 108
cgcgccacca tgggcattct tgggtttgtg ttcactctgt gagc 44

<210> SEQ ID NO 109
<211> LENGTH: 44
<212> TYPE: DNA
<213> ORGANISM: Artificial sequence
<220> FEATURE:
<223> OTHER INFORMATION: /note="Description of artificial sequence: primer N27-flu-Not-rev"

<400> SEQUENCE: 109
ggccgctcac agagtgaaca caaacccaag aatgcccatg gtgg 44

<210> SEQ ID NO 110
<211> LENGTH: 67
<212> TYPE: DNA
<213> ORGANISM: Artificial sequence
<220> FEATURE:
<223> OTHER INFORMATION: /note="Description of artificial sequence: primer N27-all-lib-Asc-for"
<220> FEATURE:
<221> NAME/KEY: variation
<222> LOCATION: 22
<223> OTHER INFORMATION: /replace="t"
<220> FEATURE:
<221> NAME/KEY: variation
<222> LOCATION: 23
<223> OTHER INFORMATION: /replace="t"
<220> FEATURE:
<221> NAME/KEY: variation
<222> LOCATION: 24
<223> OTHER INFORMATION: /replace="t"
<220> FEATURE:
<221> NAME/KEY: variation
<222> LOCATION: 25
<223> OTHER INFORMATION: /replace="t"
<220> FEATURE:
<221> NAME/KEY: variation
<222> LOCATION: 26
<223> OTHER INFORMATION: /replace="t"
<220> FEATURE:
<221> NAME/KEY: variation
<222> LOCATION: 27
<223> OTHER INFORMATION: /replace="t"
<220> FEATURE:
<221> NAME/KEY: variation
<222> LOCATION: 28
<223> OTHER INFORMATION: /replace="t"
<220> FEATURE:
<221> NAME/KEY: variation
<222> LOCATION: 29
<223> OTHER INFORMATION: /replace="t"
<220> FEATURE:
<221> NAME/KEY: variation
<222> LOCATION: 30
<223> OTHER INFORMATION: /replace="t"
<220> FEATURE:
<221> NAME/KEY: variation
<222> LOCATION: 31
<223> OTHER INFORMATION: /replace="t"
<220> FEATURE:
<221> NAME/KEY: variation
<222> LOCATION: 32
<223> OTHER INFORMATION: /replace="t"
<220> FEATURE:
<221> NAME/KEY: variation
<222> LOCATION: 33
<223> OTHER INFORMATION: /replace="t"
<220> FEATURE:
<221> NAME/KEY: variation
<222> LOCATION: 34
<223> OTHER INFORMATION: /replace="t"
<220> FEATURE:
<221> NAME/KEY: variation
<222> LOCATION: 35
<223> OTHER INFORMATION: /replace="t"
<220> FEATURE:
<221> NAME/KEY: variation
<222> LOCATION: 36
<223> OTHER INFORMATION: /replace="t"
<220> FEATURE:
<221> NAME/KEY: variation
<222> LOCATION: 37
<223> OTHER INFORMATION: /replace="t"
<220> FEATURE:
<221> NAME/KEY: variation
<222> LOCATION: 38
<223> OTHER INFORMATION: /replace="t"

<220> FEATURE:
<221> NAME/KEY: variation
<222> LOCATION: 39
<223> OTHER INFORMATION: /replace="t"
<220> FEATURE:
<221> NAME/KEY: variation
<222> LOCATION: 40
<223> OTHER INFORMATION: /replace="t"
<220> FEATURE:
<221> NAME/KEY: variation
<222> LOCATION: 41
<223> OTHER INFORMATION: /replace="t"
<220> FEATURE:
<221> NAME/KEY: variation
<222> LOCATION: 42
<223> OTHER INFORMATION: /replace="t"
<220> FEATURE:
<221> NAME/KEY: variation
<222> LOCATION: 43
<223> OTHER INFORMATION: /replace="t"
<220> FEATURE:
<221> NAME/KEY: variation
<222> LOCATION: 44
<223> OTHER INFORMATION: /replace="t"
<220> FEATURE:
<221> NAME/KEY: variation
<222> LOCATION: 45
<223> OTHER INFORMATION: /replace="t"
<220> FEATURE:
<221> NAME/KEY: variation
<222> LOCATION: 46
<223> OTHER INFORMATION: /replace="t"
<220> FEATURE:
<221> NAME/KEY: variation
<222> LOCATION: 47
<223> OTHER INFORMATION: /replace="t"
<220> FEATURE:
<221> NAME/KEY: variation
<222> LOCATION: 48
<223> OTHER INFORMATION: /replace="t"

<400> SEQUENCE: 110
cagggaaggc gcgccaccat gaagaagaag aagaagaaga agaagaagtg agcggccgct 60
aaactat 67

<210> SEQ ID NO 111
<211> LENGTH: 67
<212> TYPE: DNA
<213> ORGANISM: Artificial sequence
<220> FEATURE:
<223> OTHER INFORMATION: /note="Description of artificial sequence:
primer N27-A2-269-lib-Asc-for"
<220> FEATURE:
<221> NAME/KEY: variation
<222> LOCATION: 22
<223> OTHER INFORMATION: /replace="t"
<220> FEATURE:
<221> NAME/KEY: variation
<222> LOCATION: 23
<223> OTHER INFORMATION: /replace="t"
<220> FEATURE:
<221> NAME/KEY: variation
<222> LOCATION: 24
<223> OTHER INFORMATION: /replace="t"
<220> FEATURE:
<221> NAME/KEY: variation
<222> LOCATION: 28
<223> OTHER INFORMATION: /replace="t"
<220> FEATURE:
<221> NAME/KEY: variation
<222> LOCATION: 29
<223> OTHER INFORMATION: /replace="t"
<220> FEATURE:
<221> NAME/KEY: variation
<222> LOCATION: 30
<223> OTHER INFORMATION: /replace="t"

-continued

```
<220> FEATURE:
<221> NAME/KEY: variation
<222> LOCATION: 31
<223> OTHER INFORMATION: /replace="t"
<220> FEATURE:
<221> NAME/KEY: variation
<222> LOCATION: 32
<223> OTHER INFORMATION: /replace="t"
<220> FEATURE:
<221> NAME/KEY: variation
<222> LOCATION: 33
<223> OTHER INFORMATION: /replace="t"
<220> FEATURE:
<221> NAME/KEY: variation
<222> LOCATION: 34
<223> OTHER INFORMATION: /replace="t"
<220> FEATURE:
<221> NAME/KEY: variation
<222> LOCATION: 35
<223> OTHER INFORMATION: /replace="t"
<220> FEATURE:
<221> NAME/KEY: variation
<222> LOCATION: 36
<223> OTHER INFORMATION: /replace="t"
<220> FEATURE:
<221> NAME/KEY: variation
<222> LOCATION: 40
<223> OTHER INFORMATION: /replace="t"
<220> FEATURE:
<221> NAME/KEY: variation
<222> LOCATION: 41
<223> OTHER INFORMATION: /replace="t"
<220> FEATURE:
<221> NAME/KEY: variation
<222> LOCATION: 42
<223> OTHER INFORMATION: /replace="t"
<220> FEATURE:
<221> NAME/KEY: variation
<222> LOCATION: 43
<223> OTHER INFORMATION: /replace="t"
<220> FEATURE:
<221> NAME/KEY: variation
<222> LOCATION: 44
<223> OTHER INFORMATION: /replace="t"
<220> FEATURE:
<221> NAME/KEY: variation
<222> LOCATION: 45
<223> OTHER INFORMATION: /replace="t"

<400> SEQUENCE: 111

cagggaaggc gcgccaccat gaagatcaag aagaaggtga agaagctatg agcggccgct     60

aaactat                                                               67


<210> SEQ ID NO 112
<211> LENGTH: 18
<212> TYPE: DNA
<213> ORGANISM: Artificial sequence
<220> FEATURE:
<223> OTHER INFORMATION: /note="Description of artificial sequence:
      primer N27-Not-rev"

<400> SEQUENCE: 112

tagtttagcg gccgctca                                                   18
```